United States Patent
Chen et al.

(10) Patent No.: US 12,065,642 B2
(45) Date of Patent: *Aug. 20, 2024

(54) USING NUCLEOSOME INTERACTING PROTEIN DOMAINS TO ENHANCE TARGETED GENOME MODIFICATION

(71) Applicant: Sigma-Aldrich Co. LLC, St. Louis, MO (US)

(72) Inventors: Fuqiang Chen, St. Louis, MO (US); Xiao Ding, St. Louis, MO (US); Yongmei Feng, St. Louis, MO (US); Gregory Davis, Webster Groves, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 1030 days.

This patent is subject to a terminal disclaimer.

(21) Appl. No.: 16/793,272

(22) Filed: Feb. 18, 2020

(65) Prior Publication Data

US 2021/0024916 A1  Jan. 28, 2021

Related U.S. Application Data

(63) Continuation of application No. 16/031,819, filed on Jul. 10, 2018, now Pat. No. 10,604,752.

(60) Provisional application No. 62/531,222, filed on Jul. 11, 2017.

(51) Int. Cl.
| | |
|---|---|
| *C12N 9/22* | (2006.01) |
| *C12N 15/10* | (2006.01) |
| *C12N 15/113* | (2010.01) |
| *C12N 15/85* | (2006.01) |
| *C12N 15/90* | (2006.01) |
| *C12Q 1/6897* | (2018.01) |
| *A61K 48/00* | (2006.01) |

(52) U.S. Cl.
CPC ........... *C12N 15/102* (2013.01); *C12N 9/22* (2013.01); *C12N 15/113* (2013.01); *C12N 15/85* (2013.01); *C12N 15/907* (2013.01); *C12Q 1/6897* (2013.01); *A61K 48/005* (2013.01); *C07K 2319/09* (2013.01); *C07K 2319/10* (2013.01); *C07K 2319/80* (2013.01); *C07K 2319/81* (2013.01); *C12N 2310/20* (2017.05); *C12N 2800/80* (2013.01)

(58) Field of Classification Search
CPC ... C07K 2319/80; C12N 2310/20; C12N 9/22
See application file for complete search history.

(56) References Cited

U.S. PATENT DOCUMENTS

| | | | |
|---|---|---|---|
| 2005/0003403 A1* | 1/2005 | Rossi | A61P 29/00 530/391.1 |
| 2013/0274129 A1 | 10/2013 | Katzen et al. | |
| 2014/0273233 A1 | 9/2014 | Chen et al. | |
| 2016/0010076 A1 | 1/2016 | Joung et al. | |
| 2016/0177278 A1* | 6/2016 | Wolfe | C12N 9/22 435/199 |
| 2016/0237455 A1 | 8/2016 | Glucksmann et al. | |
| 2017/0058271 A1 | 3/2017 | Joung et al. | |
| 2019/0017042 A1 | 1/2019 | Chen et al. | |
| 2020/0208135 A1 | 7/2020 | Chen et al. | |

FOREIGN PATENT DOCUMENTS

| | | | |
|---|---|---|---|
| CN | 105188767 A | 12/2015 | |
| CN | 105247066 A | 1/2016 | |
| EP | 3428274 A1 | 1/2019 | |
| WO | 03/046141 A2 | 6/2003 | |
| WO | 2014/089290 A1 | 6/2014 | |
| WO | 2016/049251 A1 | 3/2016 | |
| WO | WO-2016036754 A1 * | 3/2016 | ........... C12N 15/102 |
| WO | 2016/057961 A1 | 4/2016 | |
| WO | 2016/103233 A2 | 6/2016 | |
| WO | 2016/205554 A1 | 12/2016 | |
| WO | 2016/210271 A1 | 12/2016 | |
| WO | 2017/031483 A1 | 2/2017 | |
| WO | 2019/014230 A1 | 1/2019 | |

OTHER PUBLICATIONS

Reeves, R. High mobility group (HMG) proteins: Modulators of chromatin structure and DNA repair in mammalian cells. DNA Repair, vol. 36, pp. 122-136, 2015. (Year: 2015).*
Postnikov et al. Functional interplay between histone H1 and HMG proteins in chromatin. Biochmica et Biophysica Acta, vol. 1859, 462-467, Oct. 8, 2015. (Year: 2015).*
Stros, M. HMGB proteins: Interactions with DNA and chromatin. Biochimica et al.Biophysica Acta, vol. 1799, pp. 101-113, 2010. (Year: 2010).*
Burstein, et al., "Major Bacterial Lineages are Essentially devoid of CRISPR-Cas Viral Defense Systems", Nature Communications, vol. 7, Article 10613, Feb. 3, 2016, 8 pages.
Burstein, et al., "New CRISPR-Cas systems from uncultivated microbes", Nature, vol. 542, Feb. 9, 2017, pp. 237-241.
Bustin, "Chromatin unfolding and activation by HMGN(*) chromosomal proteins", Trends in Biochemical Sciences, vol. 26, No. 7, Aug. 2001, pp. 431-437.
Chen, et al., "Targeted activation of diverse CRISPR-Cas systems for mammalian genome editing via proximal CRISPR targeting", Nature Communications, vol. 8, No. 14958, Apr. 7, 2017, pp. 1-12.
Chung, et al., "Human Embryonic Stem Cell Lines Generated without Embryo Destruction", Cell Stem Cell, vol. 2, Issue 2, Feb. 7, 2008, pp. 113-117.
Cong, et al., "Multiplex Genome Engineering Using CRISPR/Cas Systems", Science, vol. 339, Feb. 15, 2013, pp. 819-823.

(Continued)

*Primary Examiner* — Jennifer Dunston
(74) *Attorney, Agent, or Firm* — Sigma-Aldrich Co. LLC

(57) ABSTRACT

Compositions and methods for using nucleosome interacting protein domains to increase accessibility of programmable DNA modification proteins to target chromosomal sequences, thereby increasing efficiency of targeted genome/epigenetic modification in eukaryotic cells.

20 Claims, 1 Drawing Sheet
Specification includes a Sequence Listing.

(56) References Cited

OTHER PUBLICATIONS

Crasto, et al., "LINKER: a program to generate linker sequences for fusion proteins", Protein Engineering, vol. 13, No. 5, 2000, pp. 309-312.
Ding, et al., "Recent advances in genome editing using CRISPR/Cas9", Frontiers in Plant Science, vol. 7, Article 703, May 24, 2016, pp. 1-12.
Doi, et al., "Insertion of foreign random sequences of 120 amino acid residues into an active enzyme", FEBS Letters, vol. 402, 1997, pp. 177-180.
Fonfara, et al., "Phylogeny of Cas9 Determines Functional Exchangeability of dual-RNA and Cas9 among Orthologous type II CRISPR-Cas Systems", Nucleic Acids Research, vol. 42, No. 4, 2014, pp. 2577-2590.
Fonfara, et al., "The CRISPR-associated DNA-cleaving Enzyme Cpf1 also Processes Precursor CRISPR RNA", Nature, vol. 532, Apr. 2016, pp. 517-521.
Gen Bank, "CRISPR-associated protein, Csn1 family [Streptococcus pyogenes], 1279 amino acids", Gen Bank Accession No. BAQ51233, Jun. 2015, 1 page.
Gen Bank, "type II Crispr RNA-guided endonuclease Cas9 [Streptococcus pyogenes], 1367 amino acids", Gen Bank Accession No. WP_063631341.1, May 2016, 1 page.
Gen Bank, "type II Crispr RNA-guided endonuclease Cas9 [Streptococcus pyogenes], 1368 amino acids", Gen Bank Accession No. WP_038434062.1, Oct. 2015, 1 page.
Hinz, et al., "Nucleosomes Inhibit Cas9 Endonuclease Activity in Vitro", Biochemistry 2015, vol. 54, Nov. 18, 2015, pp. 7063-7066.
Horlbeck, et al., "Nucleosomes impede Cas9 access to DNA in vivo and in vitro", eLife, vol. 5, Mar. 17, 2016, 21 pages.
Isaac, et al., "Nucleosome breathing and remodeling constrain CRISPR-Cas9 function", eLife, vol. 5, Apr. 28, 2016, 14 pages.
Izzo, et al., "The Histone H 1 Family: Specific Members, Specific Functions?", Biological Chemistry, vol. 389, Apr. 2008, pp. 333-343.
Karvelis, et al., "Methods for Decoding Cas9 Protospacer Adjacent Motif (PAM) Sequences: A Brief Overview", Methods, vol. 121-122, 2017, pp. 3-8.
Konermann, et al., "Genome-scale transcriptional activation by an engineered CRISPR-Cas9 complex", Nature, vol. 517, No. 7536, Jan. 29, 2015, pp. 583-588.
Lombardo, et al., "Gene editing in human stem cells using zinc finger nucleases and integrase-defective lentiviral vector delivery", Nature Biotechnology, vol. 25, No. 11, Dec. 2007, pp. 1-9.
Zalatan, et al., "Engineering Complex Synthetic Transcriptional Programs with CRISPR RNA Scaffolds", Cell, vol. 160, Issue 1, Jan. 15, 2015, pp. 339-350.
Moehle, et al., "Targeted gene addition into a specified location in the human genome using designed zinc finger nucleases", PNAS, vol. 104, No. 9, Feb. 27, 2007, pp. 3055-3060.
Murray, et al., "Taxonomic Note: Implementation of the Provisional Status Candidatus for Incompletely Described Procaryotes", International Journal of Systematic Bacteriology, vol. 45, No. 1, Jan. 1995, pp. 186-187.
International Search Report and Written Opinion received for PCT Application No. PCT/US2018/041454, mailed on Sep. 27, 2018, 10 pages.
Ran, et al., "In vivo genome editing using Staphylococcus aureus Cas9", Nature, vol. 520, 2015, pp. 186-191.
Safari, et al., "CRISPR Cpf1 proteins: structure, function and implications for genome editing", 2019, pp. 1-21.
Sanjana, et al., "A transcription activator-like effector toolbox for genome engineering", Nature Protocol, vol. 7, No. 1, Jan. 2012, pp. 171-192.
Santiago, et al., "Targeted gene knockout in mammalian cells by using engineered zinc-finger nucleases", PNAS, vol. 105, No. 15, May 2008, pp. 5809-5814.

Smith, et al., "Quantitative CRISPR interference screens in yeast identify chemical-genetic interactions and new rules for guide RNA design", Genome Biology, vol. 17, Mar. 8, 2017, 16 pages.
Talbert, et al., "A unified phylogeny-based nomenclature for histone variants", Epigenetics & Chromatin, vol. 5, No. 7, May 31, 2012, pp. 1-19.
Thomas, et al., "H1 and HMGB1: Modulators of chromatin structure", Biochemical Society Transactions, vol. 40, No. 2, Apr. 2012, pp. 341-346.
Urnov, et al., "Highly efficient endogenous human gene correction using designed zinc-finger nucleases", Nature, vol. 435, Apr. 3, 2005, pp. 646-651.
Yoshioka, et al., "Efficient Generation of Human iPSCs by a Synthetic Self-Replicative RNA", Cell Stem Cell, vol. 13, Issue 2, Aug. 1, 2013, pp. 246-254.
Office Action received for Chinese Patent Application No. 201880046339.1 mailing date Feb. 22, 2023, 29 Pages (18 Pages of English translation & 11 Pages of Official copy).
O'Geen et al., "dCas9-based epigenome editing suggests acquisition of histone methylation is not sufficient for target gene repression", Nucleic acids research, vol. 45, No. 17, Jul. 4, 2017, pp. 9901-9916.
Office Action received for Australian Patent Application No. 2021245148 mailing date Jun. 19, 2023, 3 Pages.
Office Action received for Korean Patent Application No. 10-2020-7002645 mailed on Feb. 21, 2022, 10 pages (5 pages of official Copy & 5 pages of English Translation).
Office Action received for Japanese Patent Application No. 2021-201415 mailed on Jan. 17, 2023, 4 Pages (1 Page of English translation & 3 Pages of official copy).
Office Action received for Israel Patent Application No. 271197, mailed on Sep. 21, 2022, 4 Pages.
First Examination Report received for Indian Application No. 202037002227 mailed on Apr. 19, 2022, 8 Pages.
Extended European Search Report received for Patent Application No. 21193940.0 mailed on Mar. 24, 2022, 9 pages.
Office Action received for Japanese Patent Application No. 2021-201415 mailing date Jul. 11, 2023, 5 Pages (1 Page of English translation and 4 pages of official copy).
Office Action received for Korean Patent Application No. 10-2020-7002645, mailed on Sep. 22, 2022, 8 Pages (3 Pages of English Translation & 5 Pages of Official copy).
"NCBI Taxonomy Browser Entry for Acaryochloris", https://www.ncbi.nlm.nih.gov/Taxonomy/Browser/wwwtax.cgi, Oct. 18, 2019, p. 1.
"NCBI Taxonomy Browser Entry for Acetohalobium", https://www.ncbi.nlm.nih.gov/Taxonomy/Browser/wwwtax.cgi, Oct. 18, 2019, 1 page.
"NCBI Taxonomy Browser Entry for Acidaminococcus", https://www.ncbi.nlm.nih.gov/Taxonomy/Browser/wwwtax.cgi, Oct. 18, 2019, 1 page.
"NCBI Taxonomy Browser Entry for Acidithiobacillus", https://www.ncbi.nlm.nih.gov/Taxonomy/Browser/wwwtax.cgi, Oct. 18, 2019, 1 page.
"NCBI Taxonomy Browser Entry for Alicyclobacillus", https://www.ncbi.nlm.nih.gov/Taxonomy/Browser/wwwtax.cgi, Oct. 18, 2019, 1 page.
"NCBI Taxonomy Browser Entry for Allochromatium", https://www.ncbi.nlm.nih.gov/Taxonomy/Browser/wwwtax.cgi, Oct. 18, 2019, 1 page.
"NCBI Taxonomy Browser Entry for Ammonifex", https://www.ncbi.nlm.nih.gov/Taxonomy/Browser/wwwtax.cgi, Oct. 18, 2019, 1 page.
"NCBI Taxonomy Browser Entry for Anabaena", https://www.ncbi.nlm.nih.gov/Taxonomy/Browser/wwwtax.cgi, Oct. 18, 2019, 2 pages.
"NCBI Taxonomy Browser Entry for Arthrospira", https://www.ncbi.nlm.nih.gov/Taxonomy/Browser/wwwtax.cgi, Oct. 18, 2019, 1 page.
"NCBI Taxonomy Browser Entry for Bacillus", https://www.ncbi.nlm.nih.gov/Taxonomy/Browser/wwwtax.cgi, Oct. 18, 2019, 7 pages.
"NCBI Taxonomy Browser Entry for Burkholderiales", https://www.ncbi.nlm.nih.gov/Taxonomy/Browser/wwwtax.cgi, Oct. 18, 2019, 1 page.

(56) References Cited

OTHER PUBLICATIONS

"NCBI Taxonomy Browser Entry for Caldicellulosiruptor", https://www.ncbi.nlm.nih.gov/Taxonomy/Browser/wwwtax.cgi, Oct. 18, 2019, 2 pages.
"NCBI Taxonomy Browser Entry for Campylobacter", https://www.ncbi.nlm.nih.gov/Taxonomy/Browser/wwwtax.cgi, Oct. 18, 2019, 2 pages.
"NCBI Taxonomy Browser Entry for Clostridium", https://www.ncbi.nlm.nih.gov/Taxonomy/Browser/wwwtax.cgi, Oct. 18, 2019, 4 pages.
"NCBI Taxonomy Browser Entry for Crocosphaera", https://www.ncbi.nlm.nih.gov/Taxonomy/Browser/wwwtax.cgi, Oct. 18, 2019, 1 page.
"NCBI Taxonomy Browser Entry for Cyanothece", https://www.ncbi.nlm.nih.gov/Taxonomy/Browser/wwwtax.cgi, Oct. 18, 2019, 1 page.
"NCBI Taxonomy Browser Entry for Exiguobacterium", https://www.ncbi.nlm.nih.gov/Taxonomy/Browser/wwwtax.cgi, Oct. 18, 2019, 1 page.
"NCBI Taxonomy Browser Entry for Finegoldia", https://www.ncbi.nlm.nih.gov/Taxonomy/Browser/wwwtax.cgi, Oct. 18, 2019, 1 page.
"NCBI Taxonomy Browser Entry for Francisella", https://www.ncbi.nlm.nih.gov/Taxonomy/Browser/wwwtax.cgi, Oct. 18, 2019, 1 page.
"NCBI Taxonomy Browser Entry for Ktedonobacter", https://www.ncbi.nlm.nih.gov/Taxonomy/Browser/wwwtax.cgi, Oct. 18, 2019, 1 page.
"NCBI Taxonomy Browser Entry for Lachnospiraceae", https://www.ncbi.nlm.nih.gov/Taxonomy/Browser/wwwtax.cgi, Oct. 18, 2019, 2 pages.
"NCBI Taxonomy Browser Entry for Lactobacillus", https://www.ncbi.nlm.nih.gov/Taxonomy/Browser/wwwtax.cgi, Oct. 18, 2019, pp. 115-515.
"NCBI Taxonomy Browser Entry for Lyngbya", https://www.ncbi.nlm.nih.gov/Taxonomy/Browser/wwwtax.cgi, Oct. 18, 2019, 1 page.
"NCBI Taxonomy Browser Entry for Marinobacter", https://www.ncbi.nlm.nih.gov/Taxonomy/Browser/wwwtax.cgi, Oct. 18, 2019, 2 pages.
"NCBI Taxonomy Browser Entry for Methanolobium", https://www.ncbi.nlm.nih.gov/Taxonomy/Browser/wwwtax.cgi, Oct. 18, 2019, 1 page.
"NCBI Taxonomy Browser Entry for Microcoleus", https://www.ncbi.nlm.nih.gov/Taxonomy/Browser/wwwtax.cgi, Oct. 18, 2019, 1 page.
"NCBI Taxonomy Browser Entry for Microcystis", https://www.ncbi.nlm.nih.gov/Taxonomy/Browser/wwwtax.cgi, Oct. 18, 2019, 2 pages.
"NCBI Taxonomy Browser Entry for Microscilla", https://www.ncbi.nlm.nih.gov/Taxonomy/Browser/wwwtax.cgi, Oct. 18, 2019, 1 page.
"NCBI Taxonomy Browser Entry for Natranaerobius", https://www.ncbi.nlm.nih.gov/Taxonomy/Browser/wwwtax.cgi, Oct. 18, 2019, 1 page.
"NCBI Taxonomy Browser Entry for Neisseria", https://www.ncbi.nlm.nih.gov/Taxonomy/Browser/wwwtax.cgi, Oct. 18, 2019, 2 pages.
"NCBI Taxonomy Browser Entry for Nitrosococcus", https://www.ncbi.nlm.nih.gov/Taxonomy/Browser/wwwtax.cgi, Oct. 18, 2019, 1 page.
"NCBI Taxonomy Browser Entry for Nocardiopsis", https://www.ncbi.nlm.nih.gov/Taxonomy/Browser/wwwtax.cgi, Oct. 18, 2019, 2 pages.
"NCBI Taxonomy Browser Entry for Nodularia", https://www.ncbi.nlm.nih.gov/Taxonomy/Browser/wwwtax.cgi, Oct. 18, 2019, 2 pages.
"NCBI Taxonomy Browser Entry for Nostoc", https://www.ncbi.nlm.nih.gov/Taxonomy/Browser/wwwtax.cgi, Oct. 18, 2019, 2 pages.
"NCBI Taxonomy Browser Entry for Oscillatoria", https://www.ncbi.nlm.nih.gov/Taxonomy/Browser/wwwtax.cgi, Oct. 18, 2019, 2 pages.
"NCBI Taxonomy Browser Entry for Pelotomaculum", https://www.ncbi.nlm.nih.gov/Taxonomy/Browser/wwwtax.cgi, Oct. 18, 2019, 1 page.
"NCBI Taxonomy Browser Entry for Petrotoga", https://www.ncbi.nlm.nih.gov/Taxonomy/Browser/wwwtax.cgi, Oct. 18, 2019, 1 page.
"NCBI Taxonomy Browser Entry for Polaromonas", https://www.ncbi.nlm.nih.gov/Taxonomy/Browser/wwwtax.cgi, Oct. 18, 2019, 1 page.
"NCBI Taxonomy Browser Entry for Pseudoalteromonas", https://www.ncbi.nlm.nih.gov/Taxonomy/Browser/ wwwtax.cgi, Oct. 18, 2019, 2 pages.
"NCBI Taxonomy Browser Entry for *Staphylococcus*", https://www.ncbi.nlm.nih.gov/Taxonomy/Browser/wwwtax.cgi, Oct. 18, 2019, 2 pages.
"NCBI Taxonomy Browser Entry for *Streptococcus*", https://www.ncbi.nlm.nih.gov/Taxonomy/Browser/wwwtax.cgi, Oct. 18, 2019, 3 pages.
"NCBI Taxonomy Browser Entry for Streptomyces", https://www.ncbi.nlm.nih.gov/Taxonomy/Browser/wwwtax.cgi, Oct. 18, 2019, 20 pages.
"NCBI Taxonomy Browser Entry for Streptosporangium", https://www.ncbi.nlm.nih.gov/Taxonomy/Browser/wwwtax.cgi, Oct. 18, 2019, 2 pages.
"NCBI Taxonomy Browser Entry for Synechoccus", https://www.ncbi.nlm.nih.gov/Taxonomy/Browser/wwwtax.cgi, Oct. 18, 2019, 1 page.
"NCBI Taxonomy Browser Entry for Thermosipho", https://www.ncbi.nlm.nih.gov/Taxonomy/Browser/wwwtax.cgi, Oct. 18, 2019, 1 page.
"NCBI Taxonomy Browser Entry for Verrucomicrobia", https://www.ncbi.nlm.nih.gov/Taxonomy/Browser/wwwtax.cgi, Oct. 18, 2019, 28 pages.
"NCBI Taxonomy Browser Entry for Verrucomicrobia", Taxonomy ID: 74201, https://www.ncbi.nlm.nih.gov/Taxonomy/ Browser/wwwtax.cgi, Oct. 18, 2019, 1 page.
Taxonomic category not covered by the Rules of the Bacteriological Code, printed from http://www.bacterio.net/-candidatus.html, Oct. 21, 2019, 48 pages.
Search Report received for United Kingdom Patent Application No. 1811358.9, mailed on Feb. 20, 2019, 1 page.
Extended European Search Report received for European Application No. 18182999.5, mailed on Nov. 23, 2018, 3 pages.
Non Final Office Action Received for U.S. Appl. No. 16/793,253, mailing date Nov. 7, 2023, 20 Pages.
Hilton, I. B et al., "Epigenome editing by a CRISPR/Cas9-based acetyltransferase activates genes from promoters and enhancers", Nature Biotechnology, vol. 33, No. 5, Apr. 6, 2015, pp. 510-517.
Ito, K. et al., "Histone acetylation and histone deacetylation", Molecular biotechnology, vol. 20, 2002, pp. 99-106.
Lechner, M. S. et al., "The mammalian heterochromatin protein 1 binds diverse nuclear proteins through a common motif that targets the chromoshadow domain", Biochemical and biophysical research communications, vol. 331, No. 4, Apr. 12, 2005, pp. 929-937.
Makarova, K. S. et al., "An updated evolutionary classification of CRISPR-Cas systems", Nature Reviews Microbiology, vol. 13, No. 11, Nov. 28, 2015, pp. 722-736.
Mishima, Y. et al., "Hinge and chromoshadow of HP1a participate in recognition of K9 methylated histone H3 in nucleosomes", Journal of molecular biology, vol. 425, No. 1, Nov. 6, 2012, pp. 54-70.
Shmakov, S et al., "Diversity and evolution of class 2 CRISPR-Cas systems", Nat Rev Microbiology, vol. 15, No. 3, Mar. 2017, pp. 169-182.
Shmakov, S. et al., "Discovery and functional characterization of diverse class 2 CRISPR-Cas systems.", Molecular cell, vol. 60, No. 3, Nov. 5, 2015, pp. 385-397.
Examination report received for Australian Patent Application No. 2022200851 mailing date Oct. 26, 2023, 3 Pages.
Office Action received for Chinese Patent Application No. 201880046339.1 mailing date Nov. 15, 2023, 15 Pages (10 Pages of English translation & 5 Pages of official copy).

(56) References Cited

OTHER PUBLICATIONS

Office Action received for Japanese Patent Application No. 2021-201415 mailing date Dec. 5, 2023, 4 Pages (1 Page of English Translation and 3 Pages of Official copy).
Final Office Action Received for U.S. Appl. No. 16/793,253 mailing date Apr. 3, 2024, 20 Pages.
Ding, X et al., "Improving CRISPR-Cas9 genome editing efficiency by fusion with chromatin-modulating peptides", The CRISPR journal, vol. 2, No. 1, 2019, pp. 51-63.

* cited by examiner

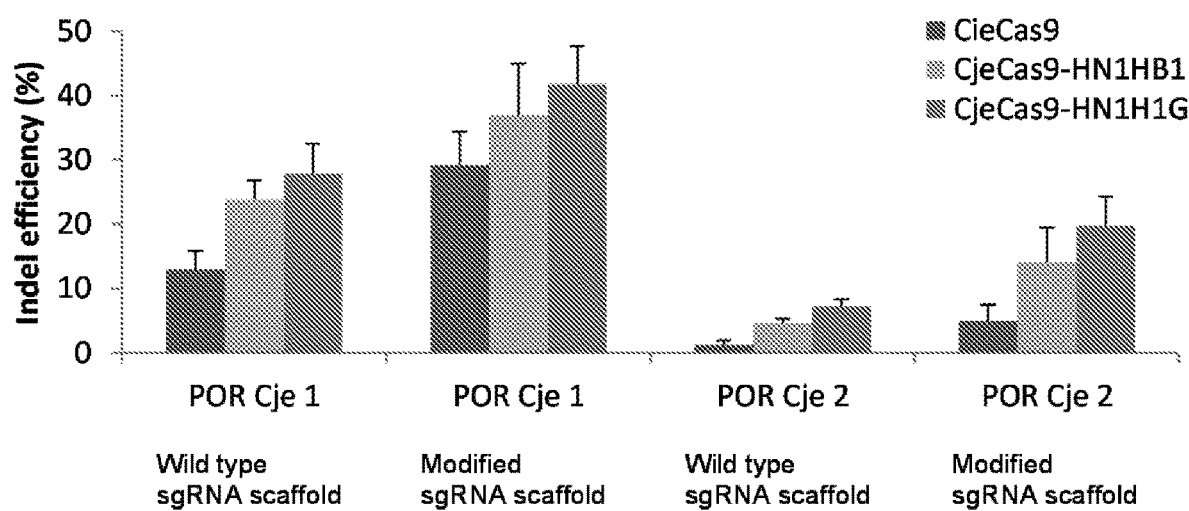

USING NUCLEOSOME INTERACTING PROTEIN DOMAINS TO ENHANCE TARGETED GENOME MODIFICATION

CROSS-REFERENCE TO RELATED APPLICATIONS

This application is a continuation application of U.S. application Ser. No. 16/031,819, filed Jul. 10, 2018, which claims priority to U.S. Provisional Application Ser. No. 62/531,222, filed Jul. 11, 2017, the disclosure of each of which is hereby incorporated by reference in its entirety.

SEQUENCE LISTING

This application contains a Sequence Listing that has been submitted in ASCII format via EFS-Web and is hereby incorporated by reference in its entirety. The ASCII copy, created on Jul. 6, 2018, is named 599979_SequenceListing_ST25.txt, and is 264 kilobytes in size.

FIELD

The present disclosure relates to compositions and methods for increasing the efficiency of targeted genome modification, targeted transcriptional regulation, or targeted epigenetic modification.

BACKGROUND

Programmable endonucleases have increasingly become an important tool for targeted genome engineering or modification in eukaryotes. Recently, RNA-guided clustered regularly interspersed short palindromic repeats (CRISPR) systems have emerged as a new generation of genome modification tools. These new programmable endonucleases provide unprecedented simplicity and versatility as compared to previous generations of nucleases such as zinc finger nucleases (ZFNs) and transcription activator-like effector nucleases (TALENs). However, chromatin barriers in eukaryotic cells can hinder target access and cleavage by the prokaryote-derived CRISPR systems (Hinz et al., Biochemistry, 2015, 54:7063-66; Horlbeck et al., eLife, 2016, 5:e12677).

In fact, no or low editing activity on certain mammalian genomic sites has been observed when using *Streptococcus pyogenes* Cas9 (SpCas9), which is considered the most active CRISPR nuclease to date. Moreover, many of the CRISPR nucleases that have been characterized thus far exhibit no activity in mammalian cells, even though they are active in bacteria or on purified DNA substrates. Therefore, there is a need to improve the ability of CRISPR nuclease systems and other programmable DNA modification proteins to overcome chromatin hindrance to increase the efficiency of targeted genome or epigenetic modification in eukaryotes.

SUMMARY

Among the various aspects of the present disclosure is the provision of fusion proteins, wherein each fusion protein comprises a CRISPR protein linked to at least one nucleosome interacting protein domain.

In general, the CRISPR protein can be a type II CRISPR/Cas9 protein or a type V CRISPR/Cpf1 protein. In certain embodiments, the CRISPR protein can be *Streptococcus pyogenes* Cas9 (SpCas9), *Streptococcus thermophilus* Cas9 (StCas9), *Streptococcus pasteurianus* Cas9 (SpaCas9), *Campylobacter jejuni* Cas9 (CjCas9), *Staphylococcus aureus* Cas9 (SaCas9), *Francisella novicida* Cas9 (FnCas9), *Neisseria cinerea* Cas9 (NcCas9), *Neisseria meningitis* Cas9 (NmCas9), *Francisella novicida* Cpf1 (FnCpf1), *Acidaminococcus* sp. Cpf1 (AsCpf1), or *Lachnospiraceae* bacterium ND2006 Cpf1 (LbCpf1).

In some embodiments, the CRISPR protein has nuclease or nickase activity. For example, the CRISPR protein can be a type II CRISPR/Cas9 nuclease or nickase, or a type V CRISPR/Cpf1 nuclease or nickase. In other embodiments, the CRISPR protein has non-nuclease activity. In such iterations, the CRISPR protein can be a type II CRISPR/Cas9 protein modified to lack all nuclease activity and linked to a non-nuclease domain, or a type V CRISPR/Cpf1 protein modified to lack all nuclease activity and linked to a non-nuclease domain, wherein the non-nuclease domain can have cytosine deaminase activity, histone acetyltransferase activity, transcriptional activation activity, or transcriptional repressor activity.

The at least one nucleosome interacting protein domain of the fusion protein can be a high mobility group (HMG) box (HMGB) DNA binding domain, a HMG nucleosome-binding (HMGN) protein, a central globular domain from a histone H1 variant, a DNA binding domain from a chromatin remodeling complex protein, or a combination thereof. In certain embodiments, the at least one nucleosome interacting protein domain of the fusion protein can be HMGB1 box A domain, HMGN1 protein, HMGN2 protein, HMGN3a protein, HMGN3b protein, histone H1 central globular domain, imitation switch (ISWI) protein DNA binding domain, chromodomain-helicase-DNA protein 1 (CHD1) DNA binding domain, or a combination thereof.

The at least one nucleosome interacting protein domain can be linked to the CRISPR protein directly via a chemical bond, indirectly via a linker, or a combination thereof. The at least one nucleosome interacting protein domain can be linked to the N-terminus, C-terminus, and/or an internal location of the CRISPR protein. In some embodiments, the fusion protein comprises at least two nucleosome interacting protein domains linked to the CRISPR protein.

The fusion proteins disclosed herein can further comprise at least one nuclear localization signal, at least one cell-penetrating domain, at least one marker domain, or a combination thereof.

In certain embodiments, the fusion protein can have an amino acid sequence having at least about 90% sequence identity with SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, or SEQ ID NO:79.

In other embodiments, the fusion protein can have an amino acid sequence as set forth in SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, or SEQ ID NO:79.

Another aspect of the present disclosure encompasses protein-RNA complexes comprising at least one of the CRISPR-containing fusion proteins disclosed herein and at least one guide RNA.

A further aspect of the present disclosure provides nucleic acids encoding any of the fusion proteins disclosed herein.

The nucleic acids can be codon optimized for translation in a eukaryotic cell. In some embodiments, the nucleic acids can be part of a vector such as, for example, a viral vector, a plasmid vector, or a self-replicating RNA.

Still another aspect of the present disclosure provides methods for increasing efficiency of targeted genome or epigenetic modification in a eukaryotic cell. The methods involve introducing into a eukaryotic cell (a) at least one fusion protein or nucleic acid encoding at least one fusion protein, each fusion protein comprising a CRISPR protein linked to at least one nucleosome interacting protein domain, wherein the CRISPR protein (i) has nuclease or nickase activity or (ii) is modified to lack all nuclease activity and is linked to a non-nuclease domain; and (b) at least one guide RNA or nucleic acid encoding at least one guide RNA; wherein the CRISPR protein of the at least one fusion protein is targeted to a target chromosomal sequence and the at least one nucleosome interacting protein domain of the at least one fusion protein alters nucleosomal or chromatin structure such that the at least one fusion protein has increased access to the target chromosomal sequence, thereby increasing efficiency of targeted genome or epigenetic modification.

In general, the CRISPR protein of the fusion protein used in the methods disclosed herein can be a type II CRISPR/Cas9 protein or a type V CRISPR/Cpf1 protein. In embodiments in which the CRISPR protein has nuclease or nickase activity, the CRISPR protein can be a type II CRISPR/Cas9 nuclease or nickase, or a type V CRISPR/Cpf1 nuclease or nickase. In embodiments in which the CRISPR protein has non-nuclease activity, the CRISPR protein can be a type II CRISPR/Cas9 protein modified to lack all nuclease activity and linked to a non-nuclease domain, or a type V CRISPR/Cpf1 protein modified to lack all nuclease activity and linked to a non-nuclease domain, wherein the non-nuclease domain can have cytosine deaminase activity, histone acetyltransferase activity, transcriptional activation activity, or transcriptional repressor activity.

The at least one nucleosome interacting protein domain of the fusion protein used in the methods can be a high mobility group (HMG) box (HMGB) DNA binding domain, a HMG nucleosome-binding (HMGN) protein, a central globular domain from a histone H1 variant, a DNA binding domain from a chromatin remodeling complex protein, or a combination thereof. In certain embodiments, the at least one nucleosome interacting protein domain of the fusion protein can be HMGB1 box A domain, HMGN1 protein, HMGN2 protein, HMGN3a protein, HMGN3b protein, histone H1 central globular domain, imitation switch (ISWI) protein DNA binding domain, chromodomain-helicase-DNA protein 1 (CHD1) DNA binding domain, or a combination thereof.

The at least one nucleosome interacting protein domain of the fusion protein used in the method can be linked to the CRISPR protein directly via a chemical bond, indirectly via a linker, or a combination thereof. The at least one nucleosome interacting protein domain can be linked to the N-terminus, C-terminus, and/or an internal location of the CRISPR protein. In some embodiments, the fusion protein used in the method comprises at least two nucleosome interacting protein domains linked to the CRISPR protein.

The fusion proteins used in the methods disclosed herein can further comprise at least one nuclear localization signal, at least one cell-penetrating domain, at least one marker domain, or a combination thereof.

In embodiments in which the method comprises introducing nucleic acid encoding the at least one fusion protein, the nucleic acid can be codon optimized for translation in the eukaryotic cell. In some embodiments, the nucleic acids can be part of a vector such as, for example, a viral vector, a plasmid vector, or a self-replicating RNA.

In certain embodiments, the method can further comprise introducing into the eukaryotic cell at least one donor polynucleotide, the donor polynucleotide comprising at least one donor sequence.

The eukaryotic cells used in the methods disclosed herein can be mammalian cells. In some embodiments, the cells can be human cell. The cells can be in vitro or in vivo.

Other aspects and features of the disclosure are detailed below.

BRIEF DESCRIPTION OF THE DRAWINGS

FIG. 1 presents the cleavage efficiency (as the percent of indels) of wild-type CjCas9 (CjeCas9), a fusion protein comprising CjCas9 linked to HMGN1 and HMGB1 box A (CjeCas9-HN1HB1), and a fusion protein comprising CjCas9 linked to HMGN1 and Histone H1 central globular domain (CjeCas9-HN1H1G) in the presence of wild-type sgRNA scaffold or modified sgRNA scaffold.

DETAILED DESCRIPTION

The present disclosure provides compositions and methods for increasing the accessibility of chromosomal DNA to programmable DNA modification proteins including CRISPR systems. In particular, the present disclosure provides fusion proteins comprising at least one nucleosome interacting protein domain linked to a programmable DNA modification protein. The nucleosome interacting protein domains alter or remodel nucleosomal and/or chromatin structure such that the programmable DNA modification protein has increased access to targeted chromosomal sequences, thereby increasing the efficiency of targeted genome modification, targeted transcriptional regulation, or targeted epigenetic modification.

(I) Fusion Proteins

One aspect of the present disclosure provides fusion proteins, wherein each fusion protein comprises at least one nucleosome interacting protein domain linked to a programmable DNA modification protein. The programmable DNA modification protein can have nuclease activity (see section (I)(b)(i), below) or non-nuclease activity (see section (I)(b)(ii), below). Nucleosome interacting protein domains are described below in section (I)(a) and linkages between the domains are described below in section (I)(c).

(a) Nucleosome Interacting Protein Domains

Nucleosome interacting protein domains refer to chromosomal proteins or fragments thereof that interact with nucleosome and/or chromosomal proteins to facilitate nucleosome rearrangement and/or chromatin remodeling. In some embodiments, the nucleosome interacting protein domain can be derived from high mobility group (HMG) box (HMGB) proteins. In other embodiments, the nucleosome interacting protein domain can be HMG nucleosome-binding (HMGN) proteins or fragments thereof. In further embodiments, the nucleosome interacting protein domain can be derived from linker histone H1 variants. In still other embodiments, the nucleosome interacting protein domain can be derived from chromatin remodeling complex proteins.

(i) HMGB Proteins

In some embodiments, the at least one nucleosome interacting protein domain can be derived from an HMGB protein. HMGB proteins interact with nucleosomes and other chromosomal proteins to regulate chromatin structure and function. Suitable HMGB proteins include mammalian HMGB1, mammalian HMGB2, and mammalian HMGB3. For example, the nucleosome interacting protein domain can be derived from a human HMGB1 (RefSeqGene, U51677), human HMGB2 (RefSeqGene, M83665), or human HMGB3 (RefSeqGene, NM_005342). In other embodiments, the nucleosome interacting protein domain can be derived from an HMGB protein or HMGB-like protein from other vertebrates, invertebrates (e.g., *Drosophila* DSP1), plants, yeast, or other single cell eukaryotes.

In specific embodiments, the at least one nucleosome interacting protein domain can be a fragment of an HMGB protein. In particular, the fragment of the HMGB protein is a DNA-binding domain. HMGB proteins typically contain two DNA-binding domains, which are called box A and box B. In some embodiments, the nucleosome interacting domain can be a box A domain or a box B domain from a HMGB protein. In specific embodiments, the nucleosome interacting domain can be a HMGB1 box A domain, a HMGB2 box A domain, or a HMGB3 box A domain.

(ii) HMGN Proteins

In other embodiments, the at least one nucleosome interacting protein domain can be a HMGN protein or fragment thereof. HMGN proteins are chromosomal proteins that modulate the structure and function of chromatin. Suitable mammalian HMGN proteins include HMGN1, HMGN2, HMGN3, HMGN3, HMGN4, and HMGN5. In various embodiments, the nucleosome interacting protein domain can be human HMGN1 (RefSeqGene, M21339), human HMGN2 (RefSeqGene, X13546), human HMGN3a or human HMGN3b (RefSeqGene, L40357), human HMGN4 (RefSeqGene, NM_030763), human HMGN5 (RefSeqGene, NM_016710), a fragment thereof, or a derivative thereof. In other embodiments, the nucleosome interacting protein domain can be a non-human HMGN protein, fragment, or derivative thereof. HMGN proteins are relatively small proteins. As such, the entire HMGN protein can be linked to the programmable DNA modification protein. In some embodiments, however, a fragment (e.g., the centrally-located nucleosome-binding domain) of a HMGN protein can be linked to the programmable DNA modification protein.

(iii) Histone H1 Variants

In still other embodiments, the at least one nucleosome interacting protein domain can be derived from a linker histone H1 variant. For example, the nucleosome interacting protein domain can be a central globular domain from a histone H1 variant. Histone H1 variants bind to the linker DNA between nucleosomes and the central globular domain (of about 80 amino acids) binds to the linker DNA at the nucleosome entry and exit sites close to the nucleosome dyad. Histone H1 variants comprise a large family of related proteins with distinct specificity for tissues, developmental stages, and organisms in which they are expressed. For example, human and mouse contain 11 histone H1 variants, chicken has six variants (which are called histone H5), frog has five variants, nematode has eight variants, fruit fly species have from one to three variants, and tobacco has six variants. In some embodiments, the histone H1 variant can be a human variant as shown below.

| Protein name* | Gene Symbol | UniProtKB Accession |
| --- | --- | --- |
| Histone H1.0 | H1F0 | P07305 |
| Histone H1.1 | HIST1H1A | Q02539 |
| Histone H1.2 | HIST1H1C | P16403 |
| Histone H1.3 | HIST1H1D | P16402 |
| Histone H1.4 | HIST1H1E | P10412 |
| Histone H1.5 | HIST1H1B | P16401 |
| Histone H1.6 (testis specific) | HIST1H1T | P22492 |
| Histone H1.7 (testis specific) | H1FNT | Q75WM6 |
| Histone H1.8 (oocyte specific) | H1FOO | Q8IZA3 |
| Histone H1.9 (testis specific) | HILS1 | P60008 |
| Histone H1.10 | H1FX | Q92522 |

*Talbert et al., Epigenetics & Chromatin, 2012, 5: 7.

(iv) Chromatin Remodeling Complex Proteins

In further embodiments, the at least one nucleosome interacting protein domain can be derived from a chromatin remodeling complex protein. For example, the nucleosome interacting protein domain can be DNA binding domain from a chromatin remodeling complex protein. Chromatin remodeling complexes are multi-subunit enzyme complexes with the capacity to remodel the structure of chromatin. These remodeling complexes use the energy of ATP hydrolysis to move, destabilize, eject, or restructure nucleosomes.

Examples of chromatin remodeling complexes include SWI/SNF (SWItch/Sucrose Non-Fermentable), ISWI (Imitation SWItch), CHD (Chromodomain-Helicase-DNA binding), Mi-2/NuRD (Nucleosome Remodeling and Deacetylase), INO80, SWR1, and RSC complexes. In various embodiments, the nucleosome interacting protein domain can be derived from an ATPase, a helicase, and/or a DNA binding protein in the chromatin remodeling complex. In some embodiments, the nucleosome interacting protein domain can be derived from the ATPase ISWI from the ISWI complex, the DNA-binding protein CHD1 from the CHD complex, the ATP-dependent helicase SMARCA4 or the ATPase Snf2 from the SWI/SNF complex, ATPase Mi-2α or ATPase Mi2-β of the Mi-1/NuRD complex, the RuvB-like AAA ATPase 1 or the RuvB-like AAA ATPase 2 from the INO80 complex, the ATPase Swr1 from the SWR1 complex, or the ATPase Rsc1 or ATPase Rcs2 from the RSC complex. In specific embodiments, the nucleosome interacting protein domain can be a DNA binding domain from ISWI protein or a DNA binding domain from CHD1 protein.

(b) Programmable DNA Modification Proteins

A programmable DNA modification protein is a protein targeted to bind a specific target sequence in chromosomal DNA, where it modifies the DNA or a protein associated with the DNA at or near the targeted sequence. Thus, a programmable DNA modification protein comprises a programmable DNA binding domain and a catalytically active modification domain.

The DNA binding domain of the programmable DNA modification protein is programmable, meaning that it can be designed or engineered to recognize and bind different DNA sequences. In some embodiments, for example, DNA binding is mediated by interactions between the DNA modification protein and the target DNA. Thus, the DNA binding domain can be programmed to bind a DNA sequence of interest by protein engineering. In other embodiments, for example, DNA binding is mediated by a guide RNA that interacts with the DNA modification protein and the target DNA. In such instances, the programmable DNA binding protein can be targeted to a DNA sequence of interest by designing the appropriate guide RNA.

A variety of modification domains can be included in the programmable DNA modification protein. In some embodiments, the modification domain has nuclease activity and can cleave one or both strands of a double-stranded DNA sequence. The DNA break can then be repaired by a cellular DNA repair process such as non-homologous end-joining (NHEJ) or homology-directed repair (HDR), such that the DNA sequence can be modified by a deletion, insertion, and/or substitution of at least one base pair. Examples of programmable DNA modification proteins having nuclease activity include, without limit, CRISPR nucleases (or nickases), zinc finger nucleases, transcription activator-like effector nucleases, meganucleases, and a programmable DNA binding domain linked to a nuclease domain. Programmable DNA modification proteins having nuclease activity are detailed below in section (I)(b)(i).

In other embodiments, the modification domain of the programmable DNA modification protein has non-nuclease activity (e.g., epigenetic modification activity or transcriptional regulation activity) such that the programmable DNA modification protein modifies the structure and/or activity of the DNA and/or protein(s) associated with the DNA. Thus, the programmable DNA modification protein can comprise a programmable DNA binding domain linked to a non-nuclease domain. Such proteins are detailed below in section (I)(b)(ii).

The programmable DNA modification proteins can comprise wild-type or naturally-occurring DNA binding and/or modification domains, modified versions of naturally-occurring DNA binding and/or modification domains, synthetic or artificial DNA binding and/or modification domains, and combinations thereof.

(i) Programmable DNA Modification Proteins with Nuclease Activity

Examples of programmable DNA modification proteins having nuclease activity include, without limit, CRISPR nucleases, zinc finger nucleases, transcription activator-like effector nucleases, meganucleases, and programmable DNA binding domains linked to nuclease domains.

CRISPR Nucleases. The CRISPR nuclease can be derived from a type I, type II (i.e., Cas9), type III, type V (i.e., Cpf1), or type VI (i.e., Cas13) CRISPR protein, which are present in various bacteria and archaea. In further embodiments, the CRISPR nuclease can be derived from an archaeal CRISPR system, a CRISPR/CasX system, or a CRISPR/CasY system (Burstein et al., Nature, 2017, 542(7640):237-241). In various embodiments, the CRISPR nuclease can be from *Streptococcus* sp. (e.g., *S. pyogenes, S. thermophilus, S. pasteurianus*), *Campylobacter* sp. (e.g., *Campylobacter jejuni*), *Francisella* sp. (e.g., *Francisella novicida*), *Acaryochloris* sp., *Acetohalobium* sp., *Acidaminococcus* sp., *Acidithiobacillus* sp., *Alicyclobacillus* sp., *Allochromatium* sp., *Ammonifex* sp., *Anabaena* sp., *Arthrospira* sp., *Bacillus* sp., *Burkholderiales* sp., *Caldicellulosiruptor* sp., *Candidatus* sp., *Clostridium* sp., *Crocosphaera* sp., *Cyanothece* sp., *Exiguobacterium* sp., *Finegoldia* sp., *Ktedonobacter* sp., *Lachnospiraceae* sp., *Lactobacillus* sp., *Lyngbya* sp., *Marinobacter* sp., *Methanohalobium* sp., *Microscilla* sp., *Microcoleus* sp., *Microcystis* sp., *Natranaerobius* sp., *Neisseria* sp., *Nitrosococcus* sp., *Nocardiopsis* sp., *Nodularia* sp., *Nostoc* sp., *Oscillatoria* sp., *Polaromonas* sp., *Pelotomaculum* sp., *Pseudoalteromonas* sp., *Petrotoga* sp., *Prevotella* sp., *Staphylococcus* sp., *Streptomyces* sp., *Streptosporangium* sp., *Synechococcus* sp., *Thermosipho* sp., or *Verrucomicrobia* sp.

The CRISPR nuclease can be a wild type or naturally-occurring protein. Alternatively, the CRISPR nuclease can be engineered to have improved specificity, altered PAM specificity, decreased off-target effects, increased stability, and the like.

In some embodiments, the CRISPR nuclease can be a type II CRISPR/Cas 9 protein. For example, the CRISPR nuclease can be *Streptococcus pyogenes* Cas9 (SpCas9), *Streptococcus thermophilus* Cas9 (StCas9), *Streptococcus pasteurianus* Cas9 (SpaCas9), *Campylobacter jejuni* Cas9 (CjCas9), *Staphylococcus aureus* Cas9 (SaCas9), *Francisella novicida* Cas9 (FnCas9), *Neisseria cinerea* Cas9 (NcCas9), or *Neisseria meningitis* Cas9 (NmCas9). In other embodiments, the CRISPR nuclease can be a type V CRISPR/Cpf1 protein, e.g., *Francisella novicida* Cpf1 (FnCpf1), *Acidaminococcus* sp. Cpf1 (AsCpf1), or *Lachnospiraceae* bacterium ND2006 Cpf1 (LbCpf1). In further embodiments, the CRISPR nuclease can be a type VI CRISPR/Cas13 protein, e.g., *Leptotrichia wadei* Cas13a (LwaCas13a) or *Leptotrichia shahii* Cas13a (LshCas13a).

In general, the CRISPR nuclease comprises at least one nuclease domain having endonuclease activity. For example, a Cas9 nuclease comprises a HNH domain, which cleaves the guide RNA complementary strand, and a RuvC domain, which cleaves the non-complementary strand, a Cpf1 protein comprises a RuvC domain and a NUC domain, and a Cas13a nuclease comprises two HNEPN domains. In some embodiments, both nuclease domains are active and the CRISPR nuclease has double-stranded cleavage activity (i.e., cleaves both strands of a double-stranded nucleic acid sequence). In other embodiments, one of the nuclease domains is inactivated by one or more mutations and/or deletions, and the CRISPR variant is a nickase that cleaves one strand of a double-stranded nucleic acid sequence. For example, one or more mutations in the RuvC domain of Cas9 protein (e.g., D10A, D8A, E762A, and/or D986A) results in an HNH nickase that nicks the guide RNA complementary strand; and one or more mutations in the HNH domain of Cas9 protein (e.g., H840A, H559A, N854A, N856A, and/or N863A) results in a RuvC nickase that nicks the guide RNA non-complementary strand. Comparable mutations can convert Cpf1 and Cas13a nucleases to nickases.

Zinc Finger Nucleases. In still other embodiments, the programmable DNA modification protein having nuclease activity can be a pair of zinc finger nucleases (ZFN). A ZFN comprises a DNA binding zinc finger region and a nuclease domain. The zinc finger region can comprise from about two to seven zinc fingers, for example, about four to six zinc fingers, wherein each zinc finger binds three consecutive base pairs. The zinc finger region can be engineered to recognize and bind to any DNA sequence. Zinc finger design tools or algorithms are available on the internet or from commercial sources. The zinc fingers can be linked together using suitable linker sequences.

A ZFN also comprises a nuclease domain, which can be obtained from any endonuclease or exonuclease. Non-limiting examples of endonucleases from which a nuclease domain can be derived include, but are not limited to, restriction endonucleases and homing endonucleases. In some embodiments, the nuclease domain can be derived from a type II-S restriction endonuclease. Type II-S endonucleases cleave DNA at sites that are typically several base pairs away from the recognition/binding site and, as such, have separable binding and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI. In some embodiments, the nuclease domain can be a FokI nuclease domain or a derivative thereof. The type II-S nuclease domain can be modified to facilitate dimerization of two different nuclease domains. For example, the cleavage domain of FokI can be modified by mutating certain amino acid residues. By way of non-limiting example, amino acid residues at positions 446, 447, 479, 483, 484, 486, 487, 490, 491, 496, 498, 499, 500, 531, 534, 537, and 538 of FokI nuclease domains are targets for modification. In specific embodiments, the FokI nuclease domain can comprise a first FokI half-domain comprising Q486E, I499L, and/or N496D mutations, and a second FokI half-domain comprising E490K, I538K, and/or H537R mutations. In some embodiments, the ZFN has double-stranded cleavage activity. In other embodiments, the ZFN has nickase activity (i.e., one of the nuclease domains has been inactivated).

Transcription Activator-like Effector Nucleases. In alternate embodiments, the programmable DNA modification protein having nuclease activity can be a transcription activator-like effector nuclease (TALEN). TALENs comprise a DNA binding domain composed of highly conserved repeats derived from transcription activator-like effectors (TALEs) that is linked to a nuclease domain. TALEs are proteins secreted by plant pathogen *Xanthomonas* to alter transcription of genes in host plant cells. TALE repeat arrays can be engineered via modular protein design to target any DNA sequence of interest. The nuclease domain of TALENs can be any nuclease domain as described above in the subsection describing ZFNs. In specific embodiments, the nuclease domain is derived from FokI (Sanjana et al., 2012, Nat Protoc, 7(1):171-192). The TALEN can have double-stranded cleavage activity or nickase activity.

Meganucleases or Rare-Cutting Endonucleases. In still other embodiments, the programmable DNA modification protein having nuclease activity can be a meganuclease or derivative thereof. Meganucleases are endodeoxyribonucleases characterized by long recognition sequences, i.e., the recognition sequence generally ranges from about 12 base pairs to about 45 base pairs. As a consequence of this requirement, the recognition sequence generally occurs only once in any given genome. Among meganucleases, the family of homing endonucleases named LAGLIDADG has become a valuable tool for the study of genomes and genome engineering. In some embodiments, the meganuclease can be I-SceI, I-TevI, or variants thereof. A meganuclease can be targeted to a specific chromosomal sequence by modifying its recognition sequence using techniques well known to those skilled in the art. In alternate embodiments, the programmable DNA modification protein having nuclease activity can be a rare-cutting endonuclease or derivative thereof. Rare-cutting endonucleases are site-specific endonucleases whose recognition sequence occurs rarely in a genome, preferably only once in a genome. The rare-cutting endonuclease may recognize a 7-nucleotide sequence, an 8-nucleotide sequence, or longer recognition sequence. Non-limiting examples of rare-cutting endonucleases include NotI, AscI, PacI, AsiSI, SbfI, and FseI.

Programmable DNA Binding Domains Linked to Nuclease Domains. In yet additional embodiments, the programmable DNA modification protein having nuclease activity can be a chimeric protein comprising a programmable DNA binding domain linked to a nuclease domain. The nuclease domain can be any of those described above in the subsection describing ZFNs (e.g., the nuclease domain can be a FokI nuclease domain), a nuclease domain derived from a CRISPR nuclease (e.g., RuvC or HNH nuclease domains of Cas9), or a nuclease domain derived from a meganuclease or rare-cutting endonuclease.

The programmable DNA binding domain of the chimeric protein can be any programmable DNA binding protein such as, e.g., a zinc finger protein or a transcription activator-like effector. Alternatively, the programmable DNA binding domain can be a catalytically inactive (dead) CRISPR protein that was modified by deletion or mutation to lack all nuclease activity. For example, the catalytically inactive CRISPR protein can be a catalytically inactive (dead) Cas9 (dCas9) in which the RuvC domain comprises a D10A, D8A, E762A, and/or D986A mutation and the HNH domain comprises a H840A, H559A, N854A, N865A, and/or N863A mutation. Alternatively, the catalytically inactive CRISPR protein can be a catalytically inactive (dead) Cpf1 protein comprising comparable mutations in the nuclease domains. In still other embodiments, the programmable DNA binding domain can be a catalytically inactive meganuclease in which nuclease activity was eliminated by mutation and/or deletion, e.g., the catalytically inactive meganuclease can comprise a C-terminal truncation.

(ii) Programmable DNA Modification Proteins with Non-Nuclease Activity

In alternate embodiments, the programmable DNA modification protein can be a chimeric protein comprising a programmable DNA binding domain linked to a non-nuclease domain. The programmable DNA binding domain can be a zinc finger protein, a transcription activator-like effector, a catalytically inactive (dead) CRISPR protein, or a catalytically inactive (dead) meganuclease. For example, the catalytically inactive CRISPR protein can be a catalytically inactive (dead) Cas9 (dCas9) in which the RuvC domain comprises a D10A, DBA, E762A, and/or D986A mutation and the HNH domain comprises a H840A, H559A, N854A, N865A, and/or N863A mutation. Alternatively, the catalytically inactive CRISPR protein can be a catalytically inactive (dead) Cpf1 protein comprising comparable mutations in the nuclease domains.

In some embodiments, the non-nuclease domain of the chimeric protein can be an epigenetic modification domain, which alters DNA or chromatin structure (and may or may not alter DNA sequence). Non-limiting examples of suitable epigenetic modification domains include those with DNA methyltransferase activity (e.g., cytosine methyltransferase), DNA demethylase activity, DNA deamination (e.g., cytosine deaminase, adenosine deaminase, guanine deaminase), DNA amination, DNA oxidation activity, DNA helicase activity, histone acetyltransferase (HAT) activity (e.g., HAT domain derived from E1A binding protein p300), histone deacetylase activity, histone methyltransferase activity, histone demethylase activity, histone kinase activity, histone phosphatase activity, histone ubiquitin ligase activity, histone deubiquitinating activity, histone adenylation activity, histone deadenylation activity, histone SUMOylating activity, histone deSUMOylating activity, histone ribosylation activity, histone deribosylation activity, histone myristoylation activity, histone demyristoylation activity, histone citrullination activity, histone alkylation activity, histone dealkylation activity, or histone oxidation activity. In specific embodiments, the epigenetic modification domain can comprise cytidine deaminase activity, histone acetyltransferase activity, or DNA methyltransferase activity.

In other embodiments, the non-nuclease modification domain of the chimeric protein can be a transcriptional activation domain or transcriptional repressor domain. Suitable transcriptional activation domains include, without limit, herpes simplex virus VP16 domain, VP64 (which is a tetrameric derivative of VP16), VP160, NFκB p65 activation domains, p53 activation domains 1 and 2, CREB (cAMP response element binding protein) activation domains, E2A activation domains, activation domain from human heat-shock factor 1 (HSF1), or NFAT (nuclear factor of activated T-cells) activation domains. Non-limiting examples of suitable transcriptional repressor domains include inducible cAMP early repressor (ICER) domains, Kruppel-associated box (KRAB) repressor domains, YY1 glycine rich repressor domains, Sp1-like repressors, E(spl) repressors, IκB repressor, or methyl-CpG binding protein 2 (MeCP2) repressor. Transcriptional activation or transcriptional repressor domains can be genetically fused to the DNA binding protein or bound via noncovalent protein-protein, protein-RNA, or protein-DNA interactions.

In particular embodiments, the non-nuclease domain of the chimeric protein can comprise cytidine deaminase activity, histone acetyltransferase activity, transcriptional activation activity, or transcriptional repressor activity.

In some embodiments, the chimeric protein having non-nuclease activity can further comprise at least one detectable label. The detectable label can be a fluorophore (e.g., FAM, TMR, Cy3, Cy5, Texas Red, Oregon Green, Alexa Fluors, Halo tags, or suitable fluorescent dye), a detection tag (e.g., biotin, digoxigenin, and the like), quantum dots, or gold particles.

(c) Linkages

The fusion proteins disclosed herein comprise at least one nucleosome interacting protein domain linked to a programmable DNA modification protein. The linkage between the at least one nucleosome interacting protein domain and the programmable DNA modification protein can be direct via a chemical bond, or the linkage can be indirect via a linker.

In some embodiments, the at least one nucleosome interacting protein domain can be linked directly to the programmable DNA modification protein by a covalent bond (e.g., peptide bond, ester bond, and the like). Alternatively, the chemical bond can be non-covalent (e.g., ionic, electrostatic, hydrogen, hydrophobic, Van der interactions, or π-effects).

In other embodiments, the at least one nucleosome interacting protein domain can be linked to the programmable DNA modification protein by a linker. A linker is a chemical group that connects one or more other chemical groups via at least one covalent bond. Suitable linkers include amino acids, peptides, nucleotides, nucleic acids, organic linker molecules (e.g., maleimide derivatives, N-ethoxybenzylimidazole, biphenyl-3,4',5-tricarboxylic acid, p-aminobenzyloxycarbonyl, and the like), disulfide linkers, and polymer linkers (e.g., PEG). The linker can include one or more spacing groups including, but not limited to alkylene, alkenylene, alkynylene, alkyl, alkenyl, alkynyl, alkoxy, aryl, heteroaryl, aralkyl, aralkenyl, aralkynyl and the like. The linker can be neutral, or carry a positive or negative charge. Additionally, the linker can be cleavable such that the linker's covalent bond that connects the linker to another chemical group can be broken or cleaved under certain conditions, including pH, temperature, salt concentration, light, a catalyst, or an enzyme.

In still other embodiments, the at least one nucleosome interacting protein domain can be linked to the programmable DNA modification protein by peptide linkers. The peptide linker can be a flexible amino acid linker (e.g., comprising small, non-polar or polar amino acids). Non-limiting examples of flexible linkers include LEGGGS (SEQ ID NO:1), TGSG (SEQ ID NO:2), GGSGGGSG (SEQ ID NO:3), (GGGGS)$_{1-4}$ (SEQ ID NO:4), and (Gly)$_{6-8}$ (SEQ ID NO:5). Alternatively, the peptide linker can be a rigid amino acid linker. Such linkers include (EAAAK)$_{1-4}$ (SEQ ID NO:6), A(EAAAK)$_{2-5}$A (SEQ ID NO:7), PAPAP (SEQ ID NO:8), and (AP)$_{6-8}$ (SEQ ID NO:9). Examples of suitable linkers are well known in the art and programs to design linkers are readily available (Crasto et al., Protein Eng., 2000, 13(5):309-312).

The at least one nucleosome interacting protein domain can be linked to N-terminus, the C-terminus, and/or an internal location of the programmable DNA modification protein. In some embodiments, at least one nucleosome interacting protein domain can be linked to N-terminus of the programmable DNA modification protein. In other embodiments, the at least one nucleosome interacting protein domain can be linked to C-terminus of the programmable DNA modification protein. In still other embodiments, at least one nucleosome interacting protein domain can be linked to N-terminus and at least one nucleosome interacting protein domain can be linked to C-terminus of the programmable DNA modification protein.

In some embodiments, the fusion protein can comprise one nucleosome interacting protein domain. In other embodiments, the fusion protein can comprise two nucleosome interacting protein domains. In still other embodiments, the fusion protein can comprise three nucleosome interacting protein domains. In additional embodiments, the fusion protein can comprise four, five, or more than five nucleosome interacting protein domains. The one or more nucleosome interacting protein domains can be the same or they can be different.

In embodiments in which the fusion protein comprises two or more nucleosome interacting protein domains, the two or more nucleosome interacting domains can be linked to either end, both ends, and/or an internal location of the programmable DNA modification protein. The two or more nucleosome interacting protein domains can be the same or they can be different. For example, the complex can comprise at least two HMG DNA-binding domains, at least two HMGN proteins, at least one HMG DNA-binding domain and at least one HMGN protein, at least one HMG DNA-binding domain or HMGN protein and at least one central domain from a histone H1 variant, at least one HMG DNA-binding domain or HMGN protein and at least one domain from a chromatin remodeling complex protein, at least one HMG DNA-binding domain or HMGN protein, at least one histone H1 variant central domain, and at least one domain from a chromatin remodeling complex protein, and the like.

(d) Optional Nuclear Localization Signal, Cell-Penetrating Domain, and/or Marker Domain The fusion proteins disclosed herein can further comprise at least one nuclear localization signal, cell-penetrating domain, and/or marker domain.

Non-limiting examples of nuclear localization signals include

PKKKRKV, (SEQ ID NO: 10)

PKKKRRV, (SEQ ID NO: 11)

KRPAATKKAGQAKKKK, (SEQ ID NO: 12)

YGRKKRRQRRR, (SEQ ID NO: 13)

RKKRRQRRR, (SEQ ID NO: 14)

PAAKRVKLD, (SEQ ID NO: 15)

RQRRNELKRSP, (SEQ ID NO: 16)

VSRKRPRP, (SEQ ID NO: 17)

PPKKARED, (SEQ ID NO: 18)

PQPKKKPL, (SEQ ID NO: 19)

SALIKKKKKMAP, (SEQ ID NO: 20)

PKQKKRK, (SEQ ID NO: 21)

RKLKKKIKKL, (SEQ ID NO: 22)

REKKKFLKRR, (SEQ ID NO: 23)

KRKGDEVDGVDEVAKKKSKK, (SEQ ID NO: 24)

RKCLQAGMNLEARKTKK, (SEQ ID NO: 25)

NQSSNFGPMKGGNFGGRSSGPYGGGGQYFAKPRNQGGY, (SEQ ID NO: 26) and

RMRIZFKNKGKDTAELRRRRVEVSVELRKAKKDEQILKRRNV. (SEQ ID NO: 27)

Examples of suitable cell-penetrating domains include, without limit,

GRKKRRQRRRPPQPKKKRKV, (SEQ ID NO: 28)

PLSSIFSRIGDPPKKKRKV, (SEQ ID NO: 29)

GALFLGWLGAAGSTMGAPKKKRKV, (SEQ ID NO: 30)

GALFLGFLGAAGSTMGAWSQPKKKRKV, (SEQ ID NO: 31)

KETWWETWWTEWSQPKKKRKV, (SEQ ID NO: 32)

YARAAARQARA, (SEQ ID NO: 33)

THRLPRRRRRR, (SEQ ID NO: 34)

GGRRARRRRRR, (SEQ ID NO: 35)

RRQRRTSKLMKR, (SEQ ID NO: 36)

GWTLNSAGYLLGKINLKALAALAKKIL, (SEQ ID NO: 37)

KALAWEAKLAKALAKALAKHLAKALAKALKCEA, (SEQ ID NO: 38) and

RQIKIWFQNRRMKWKK. (SEQ ID NO: 39)

Marker domains include fluorescent proteins and purification or epitope tags. Suitable fluorescent proteins include, without limit, green fluorescent proteins (e.g., GFP, eGFP, GFP-2, tagGFP, turboGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., BFP, EBFP, EBFP2, Azurite, mKalama1, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (e.g., mOrange, mKO, Kusabira-Orange, Monomeric Kusabira-Orange, mTangerine, tdTomato). Non-limiting examples of suitable purification or epitope tags include 6× His, FLAG®, HA, GST, Myc, and the like.

The at least one nuclear localization signal, cell-penetrating domain, and/or marker domain can be located at the N-terminus, the C-terminus, and/or in an internal location of the fusion protein.

(e) Specific Fusion Proteins

In general, the at least one nucleosome interacting protein domain of the fusion protein is chosen from HMGB1 box A domain, HMGN1 protein, HMGN2 protein, HMGN3a protein, HMGN3b protein, histone H1 central globular domain, imitation switch (ISWI) protein DNA binding domain, chromodomain-helicase-DNA protein 1 (CHD1) DNA binding domain, or combinations thereof.

In specific embodiments, the programmable DNA modification protein of the fusion protein is a CRISPR protein. For example, the CRISPR protein can be *Streptococcus pyogenes* Cas9 (SpCas9), *Streptococcus thermophilus* Cas9 (StCas9), *Streptococcus pasteurianus* Cas9 (SpaCas9), *Campylobacter jejuni* Cas9 (CjCas9), *Staphylococcus aureus* Cas9 (SaCas9), *Francisella novicida* Cas9 (FnCas9), *Neisseria cinerea* Cas9 (NcCas9), *Neisseria meningitis* Cas9 (NmCas9), *Francisella novicida* Cpf1 (FnCpf1), *Acidaminococcus* sp. Cpf1 (AsCpf1), or *Lachnospiraceae* bacterium ND2006 Cpf1 (LbCpf1).

In some embodiments, the fusion protein has an amino acid sequence having at least about 80% sequence identity with any of SEQ ID NOS:61-79. In general, any amino acid substitution is conservative, i.e., limited to exchanges within members of group 1: glycine, alanine, valine, leucine, and Isoleucine; group 2: serine, cysteine, threonine, and methionine; group 3: proline; group 4: phenylalanine, tyrosine, and tryptophan; and group 5: aspartate, glutamate, asparagine, and glutamine. In various embodiments, the amino acid sequence of the fusion protein has at least about 81%, 82%, 83%, 84%, 85%, 86%, 87%, 88%, 89%, 90%, 91%, 92%, 93%, 94%, 95%, 96%, 97%, 98, or 99% sequence identity with any of SEQ ID NOS:61-79. In some embodiments, the fusion protein has an amino acid sequence as set forth in SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, or SEQ ID NO:79.

(II) Complexes

Another aspect of the present disclosure encompasses complexes comprising at least one CRISPR system (i.e., CRISPR protein and guide RNA) and at least one nucleosome interacting protein domain. In some embodiments, the at least one nucleosome interacting protein domain can be linked to the CRISPR protein of the CRISPR system (i.e., the complex comprises a CRISPR fusion protein as described in section (I) above). In other embodiments, the at least one nucleosome interacting protein domain can be linked to the guide RNA of the CRISPR system. The linkage can be direct or indirect, essentially as described above in section (I)(c). For example, a nucleosome interacting protein domain can be linked to an RNA aptamer binding protein, and the guide RNA can comprise aptamer sequences, such that binding of the RNA aptamer binding protein to the RNA aptamer sequence links the nucleosome interacting protein domain to the guide RNA.

Nucleosome interacting protein domains are described above in section (I)(a), and CRISPR proteins are detailed above in section (I)(b). The CRISPR protein can have nuclease or nickase activity (e.g., can be a type II CRISPR/Cas9, type V CRISPR/Cpf1, or type VI CRISPR/Cas13). For example, a complex can comprise a CRISPR nuclease, or a complex can comprise two CRISPR nickases. Alternatively, the CRISPR protein can be modified to lack all nuclease activity and linked to non-nuclease domains (e.g., domains having cytosine deaminase activity, histone acetyltransferase activity, transcriptional activation activity, or transcriptional repressor activity). In some embodiments, the non-nuclease domain also can be linked to an RNA aptamer binding protein.

A guide RNA comprises (i) a CRISPR RNA (crRNA) that contains a guide sequence at the 5' end that hybridizes with a target sequence and (ii) a transacting crRNA (tracrRNA) sequence that interacts with the CRISPR protein. The crRNA guide sequence of each guide RNA is different (i.e., is sequence specific). The tracrRNA sequence is generally the same in guide RNAs designed to complex with a CRISPR protein from a particular bacterial species.

The crRNA guide sequence is designed to hybridize with a target sequence (i.e., protospacer) that is bordered by a protospacer adjacent motif (PAM) in a double-stranded sequence. PAM sequences for Cas9 proteins include 5'-NGG, 5'-NGGNG, 5'-NNAGAAW, and 5'-ACAY, and PAM sequences for Cpf1 include 5'-TTN (wherein N is defined as any nucleotide, W is defined as either A or T, and Y is defined as either C or T). In general, the complementarity between the crRNA guide sequence and the target sequence is at least 80%, at least 85%, at least 90%, at least 95%, or at least 99%. In specific embodiments, the complementarity is complete (i.e., 100%). In various embodiments, the length of the crRNA guide sequence can range from about 15 nucleotides to about 25 nucleotides. For example, the crRNA guide sequence can be about 15, 16, 17, 18, 19, 20, 21, 22, 23, 24, or 25 nucleotides in length. In specific embodiments, the crRNA can be about 19, 20, 21, or 22 nucleotides in length.

The crRNA and tracrRNA comprise repeat sequences that form one or more one-stem loop structures, which can interact with the CRISPR protein. The length of each loop and stem can vary. For example, the one or more loops can range from about 3 to about 10 nucleotides in length, and the one or more stems can range from about 6 to about 20 base pairs in length. The one or more stems can comprise one or more bulges of 1 to about 10 nucleotides.

The crRNA can range in length from about 25 nucleotides to about 100 nucleotides. In various embodiments, the crRNA can range in length from about 25 to about 50 nucleotides, from about 50 to about 75 nucleotides, or from about 75 to about 100 nucleotides. The tracrRNA can range in length from about 50 nucleotides to about 300 nucleotides. In various embodiments, the tracrRNA can range in length from about 50 to about 90 nucleotides, from about 90 to about 110 nucleotides, from about 110 to about 130 nucleotides, from about 130 to about 150 nucleotides, from about 150 to about 170 nucleotides, from about 170 to about 200 nucleotides, from about 200 to about 250 nucleotides, or from about 250 to about 300 nucleotides.

The tracrRNA sequence in the guide RNA generally is based upon the coding sequence of wild type tracrRNA in the bacterial species of interest. In some embodiments, the wild-type tracrRNA sequence (or the crRNA constant repeat region and the corresponding 5' region of the tracrRNA that forms a duplex structure with the crRNA constant repeat region) can be modified to facilitate secondary structure formation, increase secondary structure stability, facilitate expression in eukaryotic cells, increase editing efficiency, and so forth. For example, one or more nucleotide changes can be introduced into the constant guide RNA sequence (see Example 8, below).

The guide RNA can be a single molecule (i.e., a single guide RNA or sgRNA), wherein the crRNA sequence is linked to the tracrRNA sequence. Alternatively, the guide RNA can be two separate molecules. A first molecule comprising the crRNA guide sequence at the 5' end and additional sequence at 3' end that is capable of base pairing with the 5' end of a second molecule, wherein the second molecule comprises 5' sequence that is capable of base pairing with the 3' end of the first molecule, as well as additional tracrRNA sequence. In some embodiments, the guide RNA of type V CRISPR/Cpf1 systems can comprise only crRNA.

In some embodiments, the one or more stem-loop regions of the guide RNA can be modified to comprise one or more aptamer sequences (Konermann et al., Nature, 2015, 517 (7536):583-588; Zalatan et al., Cell, 2015, 160(1-2):339-50). Examples of suitable RNA aptamer protein domains include MS2 coat protein (MCP), PP7 bacteriophage coat protein (PCP), Mu bacteriophage Com protein, lambda bacteriophage N22 protein, stem-loop binding protein (SLBP), Fragile X mental retardation syndrome-related protein 1 (FXR1), proteins derived from bacteriophage such as AP205, BZ13, f1, f2, fd, fr, ID2, JP34/GA, JP501, JP34, JP500, KU1, M11, M12, MX1, NL95, PP7, φCb5, φCb8r, φCb12r, φCb23r, Qβ, R17, SP-β, TW18, TW19, and VK, fragments thereof, or derivatives thereof. The length of the additional aptamer sequence can range from about 20 nucleotides to about 200 nucleotides.

The guide RNA can comprise standard ribonucleotides, modified ribonucleotides (e.g., pseudouridine), ribonucleotide isomers, and/or ribonucleotide analogs. In some embodiments, the guide RNA can further comprise at least one detectable label. The detectable label can be a fluorophore (e.g., FAM, TMR, Cy3, Cy5, Texas Red, Oregon Green, Alexa Fluors, Halo tags, or suitable fluorescent dye), a detection tag (e.g., biotin, digoxigenin, and the like), quantum dots, or gold particles. Those skilled in the art are familiar with gRNA design and construction, e.g., gRNA design tools are available on the internet or from commercial sources.

The guide RNA can be synthesized chemically, synthesized enzymatically, or a combination thereof. For example, the guide RNA can be synthesized using standard phosphoramidite-based solid-phase synthesis methods. Alternatively, the guide RNA can be synthesized in vitro by operably linking DNA encoding the guide RNA to a promoter control sequence that is recognized by a phage RNA polymerase. Examples of suitable phage promoter sequences include T7, T3, SP6 promoter sequences, or variations thereof. In embodiments in which the guide RNA comprises two separate molecules (i.e., crRNA and tracrRNA), the crRNA can be chemically synthesized and the tracrRNA can be enzymatically synthesized.

(III) Nucleic Acids

A further aspect of the present disclosure provides nucleic acids encoding the fusion proteins described above in section (I) and the CRISPR complexes described in section (II). The CRISPR complexes can be encoded by single nucleic acids or multiple nucleic acids. The nucleic acids can be DNA or RNA, linear or circular, single-stranded or double-stranded. The RNA or DNA can be codon optimized for efficient translation into protein in the eukaryotic cell of interest. Codon optimization programs are available as freeware or from commercial sources.

In some embodiments, the nucleic acid encoding the fusion protein or the protein components of the CRISPR complex can be RNA. The RNA can be enzymatically synthesized in vitro. For this, DNA encoding the protein of interest can be operably linked to a promoter sequence that is recognized by a phage RNA polymerase for in vitro RNA synthesis. For example, the promoter sequence can be a T7, T3, or SP6 promoter sequence or a variation of a T7, T3, or SP6 promoter sequence. The DNA encoding the protein can be part of a vector, as detailed below. In such embodiments, the in vitro-transcribed RNA can be purified, capped, and/or polyadenylated. In other embodiments, the RNA encoding the fusion protein or protein component of the complex can be part of a self-replicating RNA (Yoshioka et al., Cell Stem Cell, 2013, 13:246-254). The self-replicating RNA can be derived from a noninfectious, self-replicating Venezuelan equine encephalitis (VEE) virus RNA replicon, which is a positive-sense, single-stranded RNA that is capable of self-replicating for a limited number of cell divisions, and which can be modified to code proteins of interest (Yoshioka et al., Cell Stem Cell, 2013, 13:246-254).

In other embodiments, the nucleic acid encoding the fusion protein or the CRISPR protein and guide RNA can be DNA. The DNA coding sequence can be operably linked to at least one promoter control sequence for expression in the cell of interest. In certain embodiments, the DNA coding sequence can be operably linked to a promoter sequence for expression of the protein or RNA in bacterial (e.g., *E. coli*) cells or eukaryotic (e.g., yeast, insect, or mammalian) cells. Suitable bacterial promoters include, without limit, T7 promoters, lac operon promoters, trp promoters, tac promoters (which are hybrids of trp and lac promoters), variations of any of the foregoing, and combinations of any of the foregoing. Non-limiting examples of suitable eukaryotic Pol II promoters include constitutive, regulated, or cell- or tissue-specific promoters. Suitable eukaryotic constitutive promoter control sequences include, but are not limited to, cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, ubiquitin promoters, actin promoters, tubulin promoters, immunoglobulin promoters, fragments thereof, or combinations of any of the foregoing. Examples of suitable eukaryotic regulated promoter control sequences include, without limit, those regulated by heat shock, metals, steroids, antibiotics, or alcohol. Non-limiting examples of tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, NphsI promoter, OG-2 promoter, SP-B promoter, SYN1 promoter, and WASP promoter. The promoter sequence can be wild type or it can be modified for more efficient or efficacious expression. In some embodiments, the DNA coding sequence also can be linked to a polyadenylation signal (e.g., SV40 polyA signal, bovine growth hormone (BGH) polyA signal, etc.) and/or at least one transcriptional termination sequence. The sequence encoding the guide RNA is operably linked to a Pol III promoter control sequence for expression in eukaryotic cells. Examples of suitable Pol III promoters include, but are not limited to, mammalian U6, U3, H1, and 7SL RNA promoters. In some situations, the fusion protein or components of the complex can be purified from bacterial or eukaryotic cells.

In various embodiments, nucleic acid encoding the fusion protein or the CRISPR protein and guide RNA of the complex can be present in a vector. Suitable vectors include plasmid vectors, viral vectors, and self-replicating RNA (Yoshioka et al., Cell Stem Cell, 2013, 13:246-254). In some embodiments, the nucleic acid encoding the fusion protein or the components of the complex can be present in a plasmid vector. Non-limiting examples of suitable plasmid vectors include pUC, pBR322, pET, pBluescript, and variants thereof. In other embodiments, the nucleic acid encoding the fusion protein or the components of the complex or can be part of a viral vector (e.g., lentiviral vectors, adeno-associated viral vectors, adenoviral vectors, and so forth). The plasmid or viral vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information about vectors and use thereof can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, NY, 3$^{rd}$ edition, 2001.

(IV) Kits

A further aspect of the present disclosure provides kits comprising the at least one of the fusion proteins detailed above in section (I), at least one of the CRISPR complexes described above in section (II), and/or at least one of the nucleic acids described above in section (III). The kits can further comprise transfection reagents, cell growth media, selection media, in-vitro transcription reagents, nucleic acid purification reagents, protein purification reagents, buffers, and the like. The kits provided herein generally include instructions for carrying out the methods detailed below. Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

(V) Cells

The present disclosure also provides cells comprising the at least one of the fusion proteins detailed above in section (I), at least one of the CRISPR complexes described above in section (II), and/or at least one of the nucleic acids described above in section (III). In general, the cell is a eukaryotic cell. For example, the cell can be a human cell, a non-human mammalian cell, a non-mammalian vertebrate cell, an invertebrate cell, an insect cell, a plant cell, a yeast cell, or a single cell eukaryotic organism.

(VI) Methods for Increasing Efficiency of Targeted Genome, Transcriptional, or Epigenetic Modification Another aspect of the present disclosure encompasses methods for increasing the efficiency of targeted genome modification, targeted transcriptional modification, or targeted epigenetic modification in eukaryotic cells by increasing the accessibility of a programmable DNA modification protein to its target sequence in chromosomal DNA. In some embodiments, the method comprises introducing into the eukaryotic cell of interest at least one of the fusion proteins described above in section (I), at least one of the CRISPR complexes described above in section (II), or nucleic acid encoding the at least one fusion protein or CRISPR complex as described above in section (III), and optionally, a donor polynucleotide.

The programmable DNA modification protein of the fusion protein is engineered to recognize and bind to a target sequence in chromosomal DNA, and the one or more nucleosome interacting protein domains of the fusion protein interact with nucleosomes at or near the target sequence to alter or remodel nucleosomal and/or chromatin structure. As a consequence, the DNA modification protein has increased access to the target chromosomal sequence such that efficiency of modification by the DNA modification protein is increased. In specific embodiments, the fusion protein comprises at least one nucleosome interacting protein domain linked to a CRISPR nuclease, such that interactions between the nucleosome interacting protein domain(s) and nucleosomes/chromatin at or near the target sequence increases the efficiency to targeted genomic modifications (see, Examples 1-8).

Thus, the methods disclosed herein can increase the efficiency of targeted genome editing (e.g., gene corrections, gene knock-outs, gene knock-ins, and the like), targeted epigenetic modifications, and targeted transcriptional regulation.

(a) Introduction into the Cell

As mentioned above, the method comprises introducing into the cell at least one fusion protein, at least one CRISPR complex, or nucleic acid(s) encoding said fusion protein or CRISPR complex (and, optionally, a donor polynucleotide). The at least one fusion protein, CRISPR complex, or nucleic acid(s) can be introduced into the cell of interest by a variety of means.

In some embodiments, the cell can be transfected with the appropriate molecules (i.e., protein, DNA, and/or RNA). Suitable transfection methods include nucleofection (or electroporation), calcium phosphate-mediated transfection, cationic polymer transfection (e.g., DEAE-dextran or polyethylenimine), viral transduction, virosome transfection, virion transfection, liposome transfection, cationic liposome transfection, immunoliposome transfection, nonliposomal lipid transfection, dendrimer transfection, heat shock transfection, magnetofection, lipofection, gene gun delivery, impalefection, sonoporation, optical transfection, and proprietary agent-enhanced uptake of nucleic acids. Transfection methods are well known in the art (see, e.g., "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, NY, 3rd edition, 2001). In other embodiments, the molecules can be introduced into the cell by microinjection. For example, the molecules can be injected into the cytoplasm or nuclei of the cells of interest. The amount of each molecule introduced into the cell can vary, but those skilled in the art are familiar with means for determining the appropriate amount.

The various molecules can be introduced into the cell simultaneously or sequentially. For example, the fusion protein or CRISPR complex (or encoding nucleic acids) and the donor polynucleotide can be introduced at the same time. Alternatively, one can be introduced first and then the other can be introduced later into the cell.

In general, the cell is maintained under conditions appropriate for cell growth and/or maintenance. Suitable cell culture conditions are well known in the art and are described, for example, in Santiago et al., Proc. Natl. Acad. Sci. USA, 2008, 105:5809-5814; Moehle et al. Proc. Natl. Acad. Sci. USA, 2007, 104:3055-3060; Urnov et al., Nature, 2005, 435:646-651; and Lombardo et al., Nat. Biotechnol., 2007, 25:1298-1306. Those of skill in the art appreciate that methods for culturing cells are known in the art and can and will vary depending on the cell type. Routine optimization may be used, in all cases, to determine the best techniques for a particular cell type.

(b) Targeted Genome or Epigenetic Modification

The one or more nucleosome interacting protein domains of the fusion protein or CRISPR complex interacts with nucleosomes and/or chromosomal DNA at or near the target chromosomal sequence such that nucleosomal and/or chromatin structure is altered/remodeled, thereby increasing accessibility of the programmable DNA modification protein of the fusion protein or the CRISPR protein of the CRISPR complex to the target chromosomal sequence. Increased access to the target chromosomal sequence results in increased frequency/efficiency of targeted genome, transcriptional, or epigenetic modification.

In embodiments in which the fusion protein comprises a programmable DNA modification protein having nuclease activity, the fusion protein can cleave one or both strands of the targeted chromosomal sequence. Double-stranded breaks can be repaired by a non-homologous end-joining (NHEJ) repair process. Because NHEJ is error-prone, indels (i.e., deletions or insertions) of at least one base pair, substitutions of at least one base pair, or combinations thereof can occur during the repair of the break. Accordingly, the targeted chromosomal sequence can be modified, mutated, or inactivated. For example, a deletion, insertion, or substitution in the reading frame of a coding sequence can lead to an altered protein product, or no protein product (which is termed a "knock out"). In some iterations, the method can further comprise introducing into the cell a donor polynucleotide (see below) comprising a donor sequence that is flanked by sequence having substantial sequence identity to sequences located on either side of the target chromosomal sequence, such that during repair of the double-stranded break by a homology directed repair process (HDR) the donor sequence in the donor polynucleotide can be exchanged with or integrated into the chromosomal sequence at the target chromosomal sequence. Integration of an exogenous sequence is termed a "knock in."

In various iterations, therefore, the efficiency of targeted genome modification can be increased by at least about 0.1-fold, at least about 0.5-fold, at least about 1-fold, at least about 2-fold, at least about 5-fold, at least about 10-fold, or at least about 20-fold, at least about 50-fold, at least about 100-fold, or more than about 100-fold relative to the parental programmable DNA modification protein that is not linked to at least one nucleosome interacting protein domain.

In embodiments in which the fusion protein comprises a programmable DNA modification protein having non-nuclease activity, the fusion protein can modify DNA or associated proteins at the target chromosomal sequence or modify expression of the target chromosomal sequence. For example, when the programmable DNA modification protein comprises epigenetic modification activity, the status of histone acetylation, methylation, phosphorylation, adenylation, etc. can be modified or the status of DNA methylation, amination, etc. can be modified. As an example, in embodiments in which the programmable DNA modification protein comprises cytidine deaminase activity, one or more cytidine residues at the target chromosomal sequence can be converted to uridine residues. Alternatively, when the programmable DNA modification protein comprises transcriptional activation or repressor activity, transcription at target chromosomal sequence can be increased or decreased.

The resultant epigenetic modification or transcriptional regulation can be increased by at least about 0.1-fold, at least about 0.5-fold, at least about 1-fold, at least about 2-fold, at least about 5-fold, at least about 10-fold, or at least about 20-fold, at least about 50-fold, at least about 100-fold, or more than about 100-fold relative to the parental programmable DNA modification protein that is not linked to at least one nucleosome interacting protein domain.

The targeted genome, transcriptional, epigenetic modifications detailed above can be performed singly or multiplexed (i.e., two or more chromosomal sequences can be targeted simultaneously).

(c) Optional Donor Polynucleotide

In embodiments in which the fusion protein comprises a programmable DNA modification protein having nuclease activity, the method can further comprise introducing at least one donor polynucleotide into the cell. The donor polynucleotide can be single-stranded or double-stranded, linear or circular, and/or RNA or DNA. In some embodiments, the donor polynucleotide can be a vector, e.g., a plasmid vector.

The donor polynucleotide comprises at least one donor sequence. In some aspects, the donor sequence of the donor polynucleotide can be a modified version of an endogenous or native chromosomal sequence. For example, the donor sequence can be essentially identical to a portion of the chromosomal sequence at or near the sequence targeted by the DNA modification protein, but which comprises at least one nucleotide change. Thus, upon integration or exchange with the native sequence, the sequence at the targeted chromosomal location comprises at least one nucleotide change. For example, the change can be an insertion of one or more nucleotides, a deletion of one or more nucleotides, a substitution of one or more nucleotides, or combinations thereof. As a consequence of the "gene correction" integration of the modified sequence, the cell can produce a modified gene product from the targeted chromosomal sequence.

In other aspects, the donor sequence of the donor polynucleotide can be an exogenous sequence. As used herein, an "exogenous" sequence refers to a sequence that is not native to the cell, or a sequence whose native location is in a different location in the genome of the cell. For example, the exogenous sequence can comprise protein coding sequence, which can be operably linked to an exogenous promoter control sequence such that, upon integration into the genome, the cell is able to express the protein coded by the integrated sequence. Alternatively, the exogenous sequence can be integrated into the chromosomal sequence such that its expression is regulated by an endogenous promoter control sequence. In other iterations, the exogenous sequence can be a transcriptional control sequence, another expression control sequence, an RNA coding sequence, and so forth. As noted above, integration of an exogenous sequence into a chromosomal sequence is termed a "knock in."

As can be appreciated by those skilled in the art, the length of the donor sequence can and will vary. For example, the donor sequence can vary in length from several nucleotides to hundreds of nucleotides to hundreds of thousands of nucleotides.

Typically, the donor sequence in the donor polynucleotide is flanked by an upstream sequence and a downstream sequence, which have substantial sequence identity to sequences located upstream and downstream, respectively, of the sequence targeted by the programmable DNA modification protein. Because of these sequence similarities, the upstream and downstream sequences of the donor polynucleotide permit homologous recombination between the donor polynucleotide and the targeted chromosomal sequence such that the donor sequence can be integrated into (or exchanged with) the chromosomal sequence.

The upstream sequence, as used herein, refers to a nucleic acid sequence that shares substantial sequence identity with a chromosomal sequence upstream of the sequence targeted by the programmable DNA modification protein. Similarly, the downstream sequence refers to a nucleic acid sequence that shares substantial sequence identity with a chromosomal sequence downstream of the sequence targeted by the programmable DNA modification protein. As used herein, the phrase "substantial sequence identity" refers to sequences having at least about 75% sequence identity. Thus, the upstream and downstream sequences in the donor polynucleotide can have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity with sequence upstream or downstream to the target sequence. In an exemplary embodiment, the upstream and downstream sequences in the donor polynucleotide can have about 95% or 100% sequence identity with chromosomal sequences upstream or downstream to the sequence targeted by the programmable DNA modification protein.

In some embodiments, the upstream sequence shares substantial sequence identity with a chromosomal sequence located immediately upstream of the sequence targeted by the programmable DNA modification protein. In other embodiments, the upstream sequence shares substantial sequence identity with a chromosomal sequence that is located within about one hundred (100) nucleotides upstream from the target sequence. Thus, for example, the upstream sequence can share substantial sequence identity with a chromosomal sequence that is located about 1 to about 20, about 21 to about 40, about 41 to about 60, about 61 to about 80, or about 81 to about 100 nucleotides upstream from the target sequence. In some embodiments, the downstream sequence shares substantial sequence identity with a chromosomal sequence located immediately downstream of the sequence targeted by the programmable DNA modification protein. In other embodiments, the downstream sequence shares substantial sequence identity with a chromosomal sequence that is located within about one hundred (100) nucleotides downstream from the target sequence. Thus, for example, the downstream sequence can share substantial sequence identity with a chromosomal sequence that is located about 1 to about 20, about 21 to about 40, about 41 to about 60, about 61 to about 80, or about 81 to about 100 nucleotides downstream from the target sequence.

Each upstream or downstream sequence can range in length from about 20 nucleotides to about 5000 nucleotides. In some embodiments, upstream and downstream sequences can comprise about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, or 5000 nucleotides. In specific embodiments, upstream and downstream sequences can range in length from about 50 to about 1500 nucleotides.

(d) Cell Types

A variety of cells are suitable for use in the methods disclosed herein. In general, the cell is a eukaryotic cell. For example, the cell can be a human cell, a non-human mammalian cell, a non-mammalian vertebrate cell, an invertebrate cell, an insect cell, a plant cell, a yeast cell, or a single cell eukaryotic organism. In some embodiments, the cell can also be a one cell embryo. For example, a non-human mammalian embryo including rat, hamster, rodent, rabbit, feline, canine, ovine, porcine, bovine, equine, and primate embryos. In still other embodiments, the cell can be a stem cell such as embryonic stem cells, ES-like stem cells, fetal stem cells, adult stem cells, and the like. In one embodiment, the stem cell is not a human embryonic stem cell. Furthermore, the stem cells may include those made by the techniques disclosed in WO2003/046141, which is incorporated herein in its entirety, or Chung et al. (Cell Stem Cell, 2008, 2:113-117). The cell can be in vitro or in vivo (i.e., within an organism). In exemplary embodiments, the cell is a mammalian cell or mammalian cell line. In particular embodiments, the cell is a human cell or human cell line.

Non-limiting examples of suitable mammalian cells or cell lines include human embryonic kidney cells (HEK293, HEK293T); human cervical carcinoma cells (HELA); human lung cells (W138); human liver cells (Hep G2); human U2-OS osteosarcoma cells, human A549 cells, human A-431 cells, and human K562 cells; Chinese hamster ovary (CHO) cells, baby hamster kidney (BHK) cells; mouse myeloma NSO cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T½ cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9 L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; African green monkey kidney (VERO-76) cells. An extensive list of mammalian cell lines may be found in the American Type Culture Collection catalog (ATCC, Manassas, VA).

(VII) Methods for Detecting Specific Genomic Loci

In embodiments in which the fusion protein comprises a programmable DNA modification having non-nuclease activity or the CRISPR complex comprises a catalytically inactive CRISPR protein having non-nuclease activity, said fusion protein or CRISPR complex can be used in methods for detecting or visualizing specific genomic loci in eukaryotic cells. In such embodiments, the fusion protein or CRISPR protein of the complex further comprises at least one detectable label, such as a fluorophore (e.g., FAM, TMR, Cy3, Cy5, Texas Red, Oregon Green, Alexa Fluors, Halo tags, or suitable fluorescent dye), a detection tag (e.g., biotin, digoxigenin, and the like), quantum dots, or gold particles. Alternatively, the guide RNA of the CRISPR complex can further comprise a detectable label for in situ detection (e.g., FISH or CISH). The at least one nucleosome interacting protein domain of the fusion protein or CRISPR complex increases access of the programmable DNA modification protein or CRISPR protein having non-nuclease activity to the target chromosomal sequence, thereby enhancing detection of specific genomic loci or targeted chromosomal sequences.

The method comprises introducing into the eukaryotic cell the detectably labeled fusion protein, detectably labeled CRISPR complex, or encoding nucleic acid, and detecting the labeled programmable DNA modification protein or labeled CRISPR protein bound to the target chromosomal sequence. The detecting can be via dynamic live cell imaging, fluorescent microscopy, confocal microscopy, immunofluorescence, immunodetection, RNA-protein binding, protein-protein binding, and the like. The detecting step can be performed in live cells or fixed cells.

In embodiments in which the method comprises detecting chromatin structural dynamics in live cells, the detectably labeled fusion protein or detectably labeled CRISPR complex can be introduced into the cell as proteins or nucleic acids. In embodiments in which the method comprises detecting the targeted chromosomal sequence in fixed cells, the detectably labeled fusion protein or detectably labeled CRISPR complex can be introduced into the cell as proteins (or protein-RNA complexes). Means for fixing and permeabilizing cells are well known in the art. In some embodiments, the fixed cells can be subjected to chemical and/or thermal denaturation processes to convert double-stranded chromosomal DNA into single-stranded DNA. In other embodiments, the fixed cells are not subjected to chemical and/or thermal denaturation processes.

(VIII) Applications

The compositions and methods disclosed herein can be used in a variety of therapeutic, diagnostic, industrial, and research applications. In some embodiments, the present disclosure can be used to modify any chromosomal sequence of interest in a cell, animal, or plant in order to model and/or study the function of genes, study genetic or epigenetic conditions of interest, or study biochemical pathways involved in various diseases or disorders. For example, transgenic organisms can be created that model diseases or disorders, wherein the expression of one or more nucleic acid sequences associated with a disease or disorder is altered. The disease model can be used to study the effects of mutations on the organism, study the development and/or progression of the disease, study the effect of a pharmaceutically active compound on the disease, and/or assess the efficacy of a potential gene therapy strategy.

In other embodiments, the compositions and methods can be used to perform efficient and cost effective functional genomic screens, which can be used to study the function of genes involved in a particular biological process and how any alteration in gene expression can affect the biological process, or to perform saturating or deep scanning mutagenesis of genomic loci in conjunction with a cellular phenotype. Saturating or deep scanning mutagenesis can be used to determine critical minimal features and discrete vulnerabilities of functional elements required for gene expression, drug resistance, and reversal of disease, for example.

In further embodiments, the compositions and methods disclosed herein can be used for diagnostic tests to establish the presence of a disease or disorder and/or for use in determining treatment options. Examples of suitable diagnostic tests include detection of specific mutations in cancer cells (e.g., specific mutation in EGFR, HER2, and the like), detection of specific mutations associated with particular diseases (e.g., trinucleotide repeats, mutations in β-globin associated with sickle cell disease, specific SNPs, etc.), detection of hepatitis, detection of viruses (e.g., Zika), and so forth.

In additional embodiments, the compositions and methods disclosed herein can be used to correct genetic mutations associated with a particular disease or disorder such as, e.g., correct globin gene mutations associated with sickle cell disease or thalassemia, correct mutations in the adenosine deaminase gene associated with severe combined immune deficiency (SCID), reduce the expression of HTT, the disease-causing gene of Huntington's disease, or correct mutations in the rhodopsin gene for the treatment of retinitis pigmentosa. Such modifications may be made in cells ex vivo.

In still other embodiments, the compositions and methods disclosed herein can be used to generate crop plants with improved traits or increased resistance to environmental stresses. The present disclosure can also be used to generate farm animal with improved traits or production animals. For example, pigs have many features that make them attractive as biomedical models, especially in regenerative medicine or xenotransplantation.

(IX) Enumerated Embodiments

The following enumerated embodiments are presented to illustrate certain aspects of the present invention, and are not intended to limit its scope.

1. A fusion protein comprising at least one nucleosome interacting protein domain linked to a programmable DNA modification protein.

2. The fusion protein of embodiment 1, wherein the at least one nucleosome interacting protein domain is a DNA binding domain from a high mobility group (HMG) box (HMGB) protein chosen from HMGB1, HMGB2, or HMGB3; a HMG nucleosome-binding (HMGN) protein chosen from HMGN1, HMGN2, HMGN3a, HMGN3b, HMGN4, or HMGN5; a central globular domain from a histone H1 variant; a DNA binding domain from a chromatin remodeling complex protein chosen from switch/sucrose non-fermentable (SWI/SNF) complex, imitation switch (ISWI) complex, chromodomain-helicase-DNA binding (CHD) complex, nucleosome remodeling and deacetylase (NuRD) complex, INO80 complex, SWR1 complex, RSC complex, or combination thereof.

3. The fusion protein of embodiment 2, wherein the at least one nucleosome interacting protein domain is HMGB1 box A domain, HMGN1 protein, HMGN2 protein, HMGN3a protein, HMGN3b protein, histone H1 central globular domain, ISWI protein DNA binding domain, CHD1 protein DNA binding domain, or combination thereof.

4. The fusion protein of any one of embodiments 1 to 3, wherein the programmable DNA modification protein has nuclease activity.

5. The fusion protein of embodiment 4, wherein the programmable DNA modification protein is a clustered regularly interspersed short palindromic repeats (CRISPR) nuclease or nickase, a zinc finger nuclease (ZFN), a transcription activator-like effector nuclease (TALEN), a meganuclease, or a chimeric protein comprising a programmable DNA binding domain linked to a nuclease domain.

6. The fusion protein of any one of embodiments 1 to 3, wherein the programmable DNA modification protein has non-nuclease activity.

7. The fusion protein of embodiment 6, wherein the programmable DNA modification protein is a chimeric protein comprising a programmable DNA binding domain linked to a non-nuclease domain.

8. The fusion protein of embodiment 7, wherein the programmable DNA binding domain is a CRISPR protein modified to lack all nuclease activity, a zinc finger protein, or a transcription activator-like effector.

9. The fusion protein of embodiment 7, wherein the non-nuclease domain has acetyltransferase activity, deacetylase activity, methyltransferase activity, demethylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, citrullination activity, helicase activity, amination activity, deamination activity, alkylation activity, dealkylation activity, oxidation activity, transcriptional activation activity, or transcriptional repressor activity.

10. The fusion protein of embodiment 9, wherein the non-nuclease domain has cytosine deaminase activity, histone acetyltransferase activity, transcriptional activation activity, or transcriptional repressor activity.

11. The fusion protein of any one of embodiments 1 to 10, wherein the at least one nucleosome interacting protein domain is linked to the programmable DNA modification protein directly via a chemical bond, indirectly via a linker, or combination thereof.

12. The fusion protein of any one of embodiments 1 to 11, wherein the at least one nucleosome interacting protein domain is linked to the programmable DNA modification protein at its N-terminus, C-terminus, an internal location, or combination thereof.

13. The fusion protein of any one of embodiments 1 to 12, further comprising at least one nuclear localization signal, at least one cell-penetrating domain, at least one marker domain, or combination thereof.

14. A fusion protein comprising a clustered regularly interspersed short palindromic repeats (CRISPR) protein linked to at least one nucleosome interacting protein domain.

15. The fusion protein of embodiment 14, wherein the CRISPR protein is a type II CRISPR/Cas9 nuclease or nickase, or the CRISPR protein is a type V CRISPR/Cpf1 nuclease or nickase.

16. The fusion protein of embodiment 14, wherein the CRISPR protein is a type II CRISPR/Cas9 protein modified to lack all nuclease activity and linked to a non-nuclease domain, or a type V CRISPR/Cpf1 protein modified to lack all nuclease activity and linked to a non-nuclease domain.

17. The fusion protein of embodiment 16, wherein the non-nuclease domain has cytosine deaminase activity, histone acetyltransferase activity, transcriptional activation activity, or transcriptional repressor activity.

18. The fusion protein of any one of embodiments 14 to 17, wherein the at least one nucleosome interacting protein domain is a high mobility group (HMG) box (HMGB) DNA binding domain, a HMG nucleosome-binding (HMGN) protein, a central globular domain from a histone H1 variant, a DNA binding domain from a chromatin remodeling complex protein, or a combination thereof.

19. The fusion protein of embodiment 18, wherein at least one nucleosome interacting protein domain is HMGB1 box A domain, HMGN1 protein, HMGN2 protein, HMGN3a protein, HMGN3b protein, histone H1 central globular domain, imitation switch (ISWI) protein DNA binding domain, chromodomain-helicase-DNA protein 1 (CHD1) DNA binding domain, or a combination thereof.

20. The fusion protein of any one of embodiments 14 to 19, wherein the at least one nucleosome interacting protein domain is linked to the CRISPR protein directly via a chemical bond, indirectly via a linker, or a combination thereof.

21. The fusion protein of any one of embodiments 14 to 20, wherein the at least one nucleosome interacting protein domain is linked to the CRISPR protein at its N-terminus, C-terminus, an internal location, or a combination thereof.

22. The fusion protein of any one of embodiments 14 to 21, further comprising at least one nuclear localization signal, at least one cell-penetrating domain, at least one marker domain, or a combination thereof.

23. The fusion protein of any one of embodiments 14 to 22, wherein the CRISPR protein is *Streptococcus pyogenes* Cas9 (SpCas9), *Streptococcus thermophilus* Cas9 (StCas9), *Streptococcus pasteurianus* Cas9 (SpaCas9), *Campylobacter jejuni* Cas9 (CjCas9), *Staphylococcus aureus* Cas9 (SaCas9), *Francisella novicida* Cas9 (FnCas9), *Neisseria cinerea* Cas9 (NcCas9), *Neisseria meningitis* Cas9 (NmCas9), *Francisella novicida* Cpf1 (FnCpf1), *Acidaminococcus* sp. Cpf1 (AsCpf1), or *Lachnospiraceae* bacterium ND2006 Cpf1 (LbCpf1).

24. The fusion protein of any one of embodiments 14 to 23, wherein the fusion protein has an amino acid sequence having at least about 90% sequence identity with SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, or SEQ ID NO:79.

25. The fusion protein of any one of embodiments 14 to 24, wherein the fusion protein has an amino acid sequence as set forth in SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, or SEQ ID NO:79.

26. A complex comprising at least one fusion protein of any one of embodiments 14 to 25 and at least one guide RNA.

27. A nucleic acid encoding the fusion protein of any one of embodiments 1 to 25.

28. The nucleic acid of embodiment 27, which is codon optimized for translation in a eukaryotic cell.

29. The nucleic acid of embodiments 27 or 28, which is part of a viral vector, a plasmid vector, or a self-replicating RNA.

30. A method for increasing efficiency of targeted genome or epigenetic modification in a eukaryotic cell, the method comprising introducing into the eukaryotic cell at least one fusion protein as set forth in any one of embodiments 1 to 25, or nucleic acid encoding the at least one fusion protein as set forth in any one of embodiments 27 to 29, wherein the programmable DNA modification protein of the at least one fusion protein is targeted to a target chromosomal sequence and the at least one nucleosome interacting protein domain of the at least one fusion protein alters nucleosomal or chromatin structure such that the at least one fusion protein has increased access to the target chromosomal sequence, thereby increasing efficiency of targeted genome or epigenetic modification.

31. The method of embodiment 30, wherein the DNA modification protein of the at least one fusion protein comprises a CRISPR protein and the method further comprises introducing into the eukaryotic cell at least one guide RNA or nucleic acid encoding the at least one guide RNA.

32. The method of embodiments 30 or 31, wherein the method further comprises introducing into the eukaryotic cell at least one donor polynucleotide, the donor polynucleotide comprising at least one donor sequence.

33. The method of any one of embodiments 30 to 32, wherein the eukaryotic cell is in vitro.

34. The method of any one of embodiments 30 to 32, wherein the eukaryotic cell is in vivo.

35. The method of any one of embodiments 30 to 34, wherein the eukaryotic cell is a mammalian cell.

36. The method of any one of embodiments 30 to 35, wherein the eukaryotic cell is a human cell.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd Ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about" when used in relation to a numerical value, x, for example means x±5%.

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some (e.g., 70%) of the bases are complementary. The bases that are not complementary are "mismatched." Complementarity may also be complete (i.e., 100%), if all the bases in the duplex region are complementary.

As used herein, the term "CRISPR system" refers to a complex comprising a CRISPR protein (i.e., nuclease, nickase, or catalytically dead protein) and a guide RNA.

The term "endogenous sequence," as used herein, refers to a chromosomal sequence that is native to the cell.

As used herein, the term "exogenous" refers to a sequence that is not native to the cell, or a chromosomal sequence whose native location in the genome of the cell is in a different chromosomal location.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "heterologous" refers to an entity that is not endogenous or native to the cell of interest. For example, a heterologous protein refers to a protein that is derived from or was originally derived from an exogenous source, such as an exogenously introduced nucleic acid sequence. In some instances, the heterologous protein is not normally produced by the cell of interest.

The term "nickase" refers to an enzyme that cleaves one strand of a double-stranded nucleic acid sequence (i.e., nicks a double-stranded sequence). For example, a nuclease with double strand cleavage activity can be modified by mutation and/or deletion to function as a nickase and cleave only one strand of a double-stranded sequence.

The term "nuclease," as used herein, refers to an enzyme that cleaves both strands of a double-stranded nucleic acid sequence.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine), nucleotide isomers, or nucleotide analogs. A nucleotide analog refers to a nucleotide having a modified purine or pyrimidine base or a modified ribose moiety. A nucleotide analog may be a naturally occurring nucleotide (e.g., inosine, pseudouridine, etc.) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

As used herein, the term "programmable DNA modification protein" refers to a protein that is engineered to bind a specific target sequence in chromosomal DNA and which modifies the DNA or protein(s) associated with DNA at or near the target sequence.

The term "sequence identity" as used herein, indicates a quantitative measure of the degree of identity between two sequences of substantially equal length. The percent identity of two sequences, whether nucleic acid or amino acid sequences, is the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-

6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website. In general, the substitutions are conservative amino acid substitutions: limited to exchanges within members of group 1: glycine, alanine, valine, leucine, and Isoleucine; group 2: serine, cysteine, threonine, and methionine; group 3: proline; group 4: phenylalanine, tyrosine, and tryptophan; group 5: aspartate, glutamate, asparagine, and glutamine.

The terms "target sequence," "target chromosomal sequence," and "target site" are used interchangeably to refer to the specific sequence in chromosomal DNA to which the programmable DNA modification protein is targeted, and the site at which the programmable DNA modification protein modifies the DNA or protein(s) associated with the DNA.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion.

In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity.

As various changes could be made in the above-described cells and methods without departing from the scope of the invention, it is intended that all matter contained in the above description and in the examples given below, shall be interpreted as illustrative and not in a limiting sense.

EXAMPLES

The following examples illustrate certain aspects of the disclosure. Table 1 lists the peptide sequences of nucleosome interacting domains and Table 2 presents target chromosomal sequences used in Examples 1-8 presented below.

TABLE 1

Peptide Sequences of Nucleosome Interacting Domains

| Nucleosome Interacting Domain | Sequence (NH₂-COOH) | SEQ ID NO: |
|---|---|---|
| Human HMGB1 box A domain (1-84 aa) | MGKGDPKKPRGKMSSYAFFVQTCREEHKKKHPDASVNF SEFSKKCSERWKTMSAKEKGKFEDMAKADKARYEREMK TYIPPKGE | 40 |
| Human HMGN1 protein | MPKRKVSSAEGAAKEEPKRRSARLSAKPPAKVEAKPKKA AAKDKSSDKKVQTKGKRGAKGKQAEVANQETKEDLPAE NGETKTEESPASDEAGEKEAKSD | 41 |
| Human HMGN2 protein | MPKRKAEGDAKGDKAKVKDEPQRRSARLSAKPAPPKPE PKPKKAPAKKGEKVPKGKKGKADAGKEGNNPAENGDAK TDQAQKAEGAGDAK | 42 |
| Human HMGN3a protein | MPKRKSPENTEGKDGSKVTKQEPTRRSARLSAKPAPPK PEPKPRKTSAKKEPGAKISRGAKGKKEEKQEAGKEGTAP SENGETKAEEAQKTESVDNEGE | 43 |
| Human HMGN3b protein | MPKRKSPENTEGKDGSKVTKQEPTRRSARLSAKPAPPK PEPKPRKTSAKKEPGAKISRGAKGKKEEKQEAGKEGTEN | 44 |
| Human histone H1 central globular domain (22-101 aa) | STDHPKYSDMIVAAIQAEKNRAGSSRQSIQKYIKSHYKVG ENADSQIKLSIKRLVTTGVLKQTKGVGASGSFRLAKSDEP | 45 |
| Yeast ISWI chromatin-remodeling complex ATPase ISW1 DNA binding domain | LLNPTKRERKENYSIDNYYKDVLNTGRSSTPSHPRMPKP HVFHSHQLQPPQLKVLYEKERMWTAKKTGYVPTMDDVK AAYGDISDEEEKKQKLELLKLSVNNSQPLTEEEEKMKAD WESEGFTNWNKLEFRKFITVSGKYGRNSIQAIARELAPGK TLEEVRAYAKAFWSNIERIEDYEKYLKIIENEEEKIKRVKM QQEALRRKLSEYKNPFFDLKLKHPPSSNNKRTYSEEEDR FILLMLFKYGLDRDDVYELVRDEIRDCPLFELDFYFRSRTP VELARRGNTLLQCLEKEFNAGIVLDDATKDRMKKEDENG KRIREEFADQTANEKENVDGVESKKAKIEDTSNVGTEQLV AEKIPENETTH | 46 |
| Yeast chromo domain-containing | DMDSIGESEVRALYKAILKFGNLKEILDELIADGTLPVKSFE KYGETYDEMMEAAKDCVHEEEKNRKEILEKLEKHATAYR AKLKSGEIKAENQPKDNPLTRLSLKKREKKAVLFNFKGVK | 47 |

TABLE 1-continued

Peptide Sequences of Nucleosome Interacting Domains

| Nucleosome Interacting Domain | Sequence (NH$_2$-COOH) | SEQ ID NO: |
|---|---|---|
| protein 1 (CHD1) DNA binding domain | SLNAESLLSRVEDLKYLKNLINSNYKDDPLKFSLGNNTPK PVQNWSSNWTKEEDEKLLIGVFKYGYGSWTQIRDDPFL GITDKIFLNEVHNPVAKKSASSSDTTPTPSKKGKGITGSSK KVPGAIHLGRRVDYLLSFLRGGLNTKSPS | |

TABLE 2

Chromosomal Target Sites

| Locus | Site | Sequence (5'-3') | SEQ ID NO: |
|---|---|---|---|
| *Streptococcus pyogenes* Cas9 (SpCas9) | | | |
| POR | #1 | AGCCGTGAGTGGAGGGAGCGTGG | 48 |
| POR | #2 | AGAGGGAGGGGTTGGACTACAGG | 49 |
| POR | #3 | CATTCGCCAGTACGAGCTTGTGG | 50 |
| CAR | #1 | CTTTAATGCGCTGACTTGTGAGG | 51 |
| EMX1 | #1 | GTGGCGCATTGCCACGAAGCAGG | 52 |
| EMX1 | #2 | TTCTTCTTCTGCTCGGACTCAGG | 53 |
| *Streptococcus pasteurianus* Cas9 (SpaCas9) | | | |
| POR | #1 | TGCTGGAAAGGGGAGACCAAGGGTGA | 54 |
| POR | #2 | AGAGCTACGAGAACCAGAAGCCGTGA | 55 |
| *Francisella novicida* Cpf1 (FnCpf1) | | | |
| POR | #1 | TTCCCGGCCTCACCCTTGGTCTCCCC | 56 |
| POR | #2 | TTGGTCTCCCCTTTCCAGCATTCGCC | 57 |
| POR | #3 | TTCCAGCATTCGCCAGTACGAGCTTG | 58 |
| *Campylobacter jejuni* Cas9 (CjCas9) | | | |
| POR | #1 | GATCAACATGGGAGACTCCCACGTGGACAC | 59 |
| POR | #2 | AGATACTTCTTCGGCCACCGCCTCGGACAC | 60 |

Example 1. Improvement of *Streptococcus pyogenes* Cas9 (SpCas9) Activity Using Human HMGB1 Box A Domain A human HMGB1 box A domain (SEQ ID NO:40) was fused with SpCas9 (+NLS) at the nuclease carboxyl terminus with the linker LEGGGS (SEQ ID NO:1) between Cas9 and the HMGB1 box A domain. Human K562 cells (1×10$^6$) were transfected with plasmid DNA encoding the fusion protein or wild type SpCas9 protein in molar equivalent amounts (5.2 and 5.0 μg for the fusion protein and the wild type Cas9 protein, respectively) in combination with 3 μg of a sgRNA plasmid for targeting a genomic site (#1) in the human cytochrome p450 oxidoreductase (POR) locus. Transfection was carried out using nucleofection on an Amaxi nucleofector. Three days after transfection, cells were lysed with a DNA extraction solution (QuickExtract™) and the targeted genomic region was PCR amplified. Cas9 nuclease target cleavage activities (% indels) were measured using Cel-I assays. As shown in Table 3, fusion of the human HMGB1 box A domain with the nuclease increased SpCas9 cleavage efficiency at the target site.

TABLE 3

| Cleavage Efficiency | | |
|---|---|---|
| Nuclease | Target Site | Indel (%) |
| Wild type SpCas9 | POR/site #1 | 8.5 |
| SpCas9-HMGB1 box A fusion | POR/site #1 | 21.3 |

Example 2. Improvement of *Streptococcus pyogenes* Cas9 (SpCas9) Activity Using Human HMGN1, HMGN2, HMGN3a, and HMGN3b Human HMGN1, HMGN2, HMGN3a, and HMGN3b (SEQ ID NOS:41-44, respectively) were each fused with SpCas9 (+NLS) at the nuclease carboxyl terminus with the linker LEGGGS (SEQ ID NO:1) between Cas9 and each of the HMGN peptides. Human K562 cells (1×10$^6$) were transfected with plasmid DNA encoding each of the fusion proteins or the wild type SpCas9 protein in molar equivalent amounts (5.2 and 5.0 μg for each of the fusion proteins and the wild type Cas9 protein, respectively) in combination with 3 μg of a sgRNA plasmid for targeting a genomic site (#1) in the human cytochrome p450 oxidoreductase (POR) locus. Transfection was carried out using nucleofection on an Amaxi nucleofector. Three days after transfection, cells were lysed with a DNA extraction solution (QuickExtract™) and the targeted genomic region was PCR amplified. Cas9 target cleavage activities (% indels) were measured using Cel-I assays. The results, as summarized in Table 4, show that fusion of each of the human HMGN peptides with the nuclease increased SpCas9 cleavage efficiency at the target site.

TABLE 4

| Cleavage Efficiency | | |
|---|---|---|
| Nuclease | Target Site | Indel (%) |
| Wild type SpCas9 | POR/site #1 | 8.5 |
| SpCas9-HMGN1 fusion | POR/site #1 | 18.3 |
| SpCas9-HMGN2 fusion | POR/site #1 | 13.3 |
| SpCas9-HMGN3a fusion | POR/site #1 | 13.5 |
| SpCas9-HMGN3b fusion | POR/site #1 | 14.4 |

Example 3. Improvement of *Streptococcus pyogenes* Cas9 (SpCas9) Activity Using Human Histone H1 Central Globular Domain A human histone H1 central globular domain (SEQ ID NO:45) was fused with SpCas9 (+NLS) at the nuclease carboxyl terminus with the linker LEGGGS (SEQ ID NO:1) between Cas9 and the globular domain. Human K562 cells (1×10⁶) were transfected with plasmid DNA encoding the fusion protein or the wild type SpCas9 protein in molar equivalent amounts (5.2 and 5.0 μg for the fusion protein and the wild type Cas9 protein, respectively) in combination with 3 μg of a sgRNA plasmid for targeting a genomic site (#1) in the human cytochrome p450 oxidoreductase (POR) locus. Transfection was carried out using nucleofection on an Amaxi nucleofector. Three days after transfection, cells were lysed with a DNA extraction solution (QuickExtract™) and the targeted genomic region was PCR amplified. Cas9 target cleavage activities (% indels) were measured using Cel-I assays. The results are presented in Table 5. Fusion of the human histone H1 central globular domain with the nuclease increased SpCas9 cleavage efficiency at the target site.

TABLE 5

| Cleavage Efficiency | | |
| --- | --- | --- |
| Nuclease | Target Site | Indel (%) |
| Wild type SpCas9 | POR/site #1 | 8.5 |
| SpCas9-H1 central globular domain fusion | POR/site #1 | 19.4 |

Example 4. Improvement of *Streptococcus pyogenes* Cas9 (SpCas9) Activity Using a Chromatin Remodeling Protein DNA Binding Domain SpCas9 (+NLS) was fused with the DNA binding domain of the yeast ISWI chromatin-remodeling complex ATPase ISW1 (SEQ ID NO:46) at the nuclease amino terminus with the linker TGSG (SEQ ID NO:2) between Cas9 and the DNA binding domain. Independently, the wild type SpCas9 was fused with the DNA binding domain of the yeast chromo domain-containing protein 1 (CHD1) (SEQ ID NO:47) at the nuclease carboxyl terminus with the linker LEGGGS (SEQ ID NO:1) between Cas9 and the DNA binding domain. Human K562 cells (1×10⁶) were transfected with plasmid DNA encoding each of the fusion proteins or the wild type SpCas9 protein in molar equivalent amounts (6.0 and 5.0 μg for each of the fusion proteins and the wild type Cas9 protein, respectively) in combination with 3 μg of a sgRNA plasmid for targeting a genomic site (#1) in the human cytochrome p450 oxidoreductase (POR) locus. Transfection was carried out using nucleofection on an Amaxi nucleofector. Three days after transfection, cells were lysed with a DNA extraction solution (QuickExtract™) and the targeted genomic region was PCR amplified. Cas9 target cleavage activities (% indels) were measured using Cel-I assays. The results, as summarized in Table 6, show that the fusion of each of the DNA binding domains with the nuclease increased SpCas9 cleavage efficiency at the target site.

TABLE 6

| Cleavage Efficiency | | |
| --- | --- | --- |
| Nuclease | Target Site | Indel (%) |
| Wild type SpCas9 | POR/site #1 | 8.5 |
| ISW1 DNA binding domain-SpCas9 fusion | POR/site #1 | 21.1 |

TABLE 6-continued

| Cleavage Efficiency | | |
| --- | --- | --- |
| Nuclease | Target Site | Indel (%) |
| SpCas9-CHD1 DNA binding domain fusion | POR/site #1 | 20.8 |

Example 5. Improvement of *Streptococcus pyogenes* Cas9 (SpCas9) Activity Using Combinations of Nucleosome Interacting Domains SpCas9 (+NLS) was fused with the human HMGN1 (SEQ ID NO:41) at the nuclease amino terminus with the linker TGSG (SEQ ID NO:2) between Cas9 and HMGN1 and with the human HMGB1 box A domain (SEQ ID NO:40) or the human histone H1 central globular domain (SEQ ID NO: 45) or the yeast chromo domain-containing protein 1 (CHD1) DNA binding domain (SEQ ID NO:47) at the nuclease carboxyl terminus with the linker LEGGGS (SEQ ID NO: 1) between Cas9 and each of the protein domains. Human K562 cells (1×10⁶) were transfected with plasmid DNA encoding each of the fusion proteins or the wild type SpCas9 protein in molar equivalent amounts (5.4 μg for the HMGB1 box A and H1 central globular domain fusion proteins, 6.0 μg for the CHD1 DNA binding domain fusion protein, and 5.0 μg for the wild type Cas9 protein) in combination with 3 μg of a sgRNA plasmid for targeting a genomic site (#1, #2, #3) in the human cytochrome p450 oxidoreductase (POR) locus, or a genomic site (#1) the human nuclear receptor subfamily 1 group I member 3 (CAR) locus, or a genomic site (#1, #2) the human empty spiracles homeobox 1 (EMX1) locus. Transfection was carried out using nucleofection on an Amaxi nucleofector. Five days after transfection, cells were lysed with a DNA extraction solution (QuickExtract™) and each targeted genomic region was PCR amplified. Cas9 target cleavage activities (% indels) were measured using Cel-I assays. The results, as summarized in the Table 7, show that the combinatory fusion of these protein domains with the nuclease increased SpCas9 cleavage efficiency at the target sites.

TABLE 7

| Cleavage Efficiency | | |
| --- | --- | --- |
| Nuclease | Target Site | Indel (%) |
| Wild type SpCas9 | POR/site #1 | 3.4 |
|  | POR/site #2 | 1.3 |
|  | POR/site #3 | 22.2 |
|  | CAR/site #1 | 2.1 |
|  | EMX1/site #1 | 2.2 |
|  | EMX1/site #2 | 1.1 |
| HMGN1-SpCas9-HMGB1 box A fusion | POR/site #1 | 28.2 |
|  | POR/site #2 | 8.3 |
|  | POR/site #3 | 42.7 |
|  | CAR/site #1 | 14.3 |
|  | EMX1/site #1 | 29.0 |
|  | EMX1/site #2 | 12.1 |
| HMGN1-SpCas9-H1 central globular domain fusion | POR/site #1 | 24.3 |
|  | POR/site #2 | 6.5 |
|  | POR/site #3 | 44.2 |
|  | CAR/site #1 | 23.9 |
|  | EMX1/site #1 | 26.9 |
|  | EMX1/site #2 | 21.0 |

TABLE 7-continued

Cleavage Efficiency

| Nuclease | Target Site | Indel (%) |
|---|---|---|
| HMGN1-SpCas9- CHD1 DNA binding domain fusion | POR/site #1 | 21.5 |
|  | POR/site #2 | 3.6 |
|  | POR/site #3 | 39.8 |
|  | CAR/site #1 | 9.0 |
|  | EMX1/site #1 | 23.5 |
|  | EMX1/site #2 | 20.2 |

Example 6. Improvement of *Streptococcus pasteurianus* Cas9 (SpaCas9) Activity Using Combinations of Nucleosome Interacting Domains

*Streptococcus pasteurianus* Cas9 (SpaCas9) (+NLS) was fused with the human HMGN1 (SEQ ID NO:41) at the nuclease amino terminus with the linker TGSG (SEQ ID NO:2) between Cas9 and HMGN1 and with the human HMGB1 box A domain (SEQ ID NO:40) or the human histone H1 central globular domain (SEQ ID NO:45) or the yeast chromo domain-containing protein 1 (CHD1) DNA binding domain (SEQ ID NO:47) at the nuclease carboxyl terminus with the linker LEGGGS (SEQ ID NO:1) between Cas9 and each of the protein domains. Human K562 cells ($1 \times 10^6$) were transfected with plasmid DNA encoding each of the fusion proteins or the wild type SpaCas9 protein in molar equivalent amounts (5.4 and 5.0 µg for each of the fusion proteins and the wild type Cas9 protein, respectively) in combination with 3 µg of a sgRNA plasmid for targeting a genomic site (#1, #2) in the human cytochrome p450 oxidoreductase (POR) locus. Transfection was carried out using nucleofection on an Amaxi nucleofector. Three days after transfection, cells were lysed with a DNA extraction solution (QuickExtract™) and the targeted genomic region was PCR amplified. Cas9 target cleavage activities (% indels) were measured using Cel-I assays. As summarized in Table 8, the combinatory fusion of these protein domains with the nuclease increased SpaCas9 cleavage efficiency at the target sites.

TABLE 8

Cleavage Efficiency

| Nuclease | Target Site | Indel (%) |
|---|---|---|
| Wild type SpaCas9 | POR/site #1 | 16.6 |
|  | POR/site #2 | 12.9 |
| HMGN1-SpaCas9-HMGB1 box A fusion | POR/site #1 | 20.6 |
|  | POR/site #2 | 35.8 |
| HMGN1-SpaCas9-H1 central globular domain fusion | POR/site #1 | 28.6 |
|  | POR/site #2 | 31.7 |
| HMGN1-SpaCas9-CHD1 DNA binding domain fusion | POR/site #1 | 19.4 |
|  | POR/site #2 | 18.5 |

Example 7. Improvement of *Francisella novicida* Cpf1 (FnCpf1) Activity Using Combinations of Nucleosome Interacting Domains

*Francisella novicida* Cpf1 (FnCpf1) (+NLS) was fused with the human HMGN1 (SEQ ID NO:41) at the nuclease amino terminus with the linker TGSG (SEQ ID NO:2) between Cpf1 and HMGN1 and with the human HMGB1 box A domain (SEQ ID NO:40) or the human histone H1 central globular domain (SEQ ID NO:45) or the yeast chromo domain-containing protein 1 (CHD1) DNA binding domain (SEQ ID NO:47) at the nuclease carboxyl terminus with the linker LEGGGS (SEQ ID NO:1) between Cpf1 and each of the protein domains. Human K562 cells ($1 \times 10^6$) were transfected with plasmid DNA encoding each of the fusion proteins or the wild type FnCpf1 protein in molar equivalent amounts (5.4 and 5.0 µg for each of the fusion proteins and the wild type Cas9 protein, respectively) in combination with 3 µg of a sgRNA plasmid for targeting a genomic site (#1, #2, #3) in the human cytochrome p450 oxidoreductase (POR) locus. Transfection was carried out using nucleofection on an Amaxi nucleofector. Three days after transfection, cells were lysed with a DNA extraction solution (QuickExtract™) and the targeted genomic region was PCR amplified. Cas9 target cleavage activities (% indels) were measured using Cel-I assays. The results, as summarized in Table 9, show that the combinatory fusion of these protein domains with the nuclease increased FnCpf1 cleavage efficiency on the target sites.

TABLE 9

Cleavage Efficiency

| Nuclease | Target Site | Indel (%) |
|---|---|---|
| Wild typeFnCpf1 | POR/site #1 | 2.3 |
|  | POR/site #2 | 5.3 |
|  | POR/site #3 | 3.0 |
| HMGN1-FnCpf1-HMGB1 box A fusion | POR/site #1 | 8.2 |
|  | POR/site #2 | 12.8 |
|  | POR/site #3 | 13.2 |
| HMGN1-FnCpf1-H1 central globular domain fusion | POR/site #1 | 8.7 |
|  | POR/site #2 | 12.9 |
|  | POR/site #3 | 13.2 |
| HMGN1-FnCpf1-CHD1 DNA binding domain fusion | POR/site #1 | 7.7 |
|  | POR/site #2 | 7.5 |
|  | POR/site #3 | 9.4 |

Example 8. Improvement of *Campylobacter jejuni* Cas9 (CjCas9) Gene Editing Efficiency

*Campylobacter jejuni* Cas9 (CjCas9) (+NLS) was fused with the human HMGN1 (SEQ ID NO:41) at the nuclease amino terminus with the linker TGSG (SEQ ID NO:2) between Cas9 and HMGN1 and with the human HMGB1 box A domain (SEQ ID NO:40) or the human histone H1 central globular domain (SEQ ID NO:45) at the nuclease carboxyl terminus with the linker LEGGGS (SEQ ID NO:1) between Cas9 and each of the protein domains. The wild type CjCas9 gRNA was modified by introducing a U to C mutation into the crRNA constant repeat region and a corresponding A to G mutation into the 5' region of the tracrRNA sequence. The modified sgRNA sequence is: 5'-NNNNNNNNNNNNNNNNNNNNNNGUUCUAGU-CCCUGAAAAGGGACUAGAAUAAAG AGUUUGCGGGACUCUGCGGGGUUACAAUCCCC-UAAAACCGCUUUU-3', where the mutated nucleotides in the crRNA and tracrRNA moieties are underlined. Guide sequences targeting two different sites (#1, #2) in the human cytochrome p450 oxidoreductase gene (POR) were cloned into the wild type and the modified CjCas9 sgRNA scaffold, respectively. The expression of the sgRNAs was under the control of a U6 promoter. Human K562 cells ($1 \times 10^6$) were transfected with 4 µg of CjCas9 plasmid DNA and 3 µg of a sgRNA plasmid DNA. Transfection was carried out using nucleofection on an Amaxi nucleofector. Three days after transfection, cells were lysed with QuickExtract and the targeted genomic regions were PCR amplified. CjCas9 targeted DNA cleavage activities (% indels) were measured using Cel-I assays. The results are presented in FIG. 1 and show that the fusion proteins had increased cleavage efficiency on the target sites, and that modified CjCas9 sgRNA scaffold effectively increased CjCas9 cleavage efficiency on target sites.

Table 10 presents the amino acid sequences of the specific fusion proteins. The nucleosome interacting protein domains are shown in bold, the linkers are shown in italics, and the NLS is underlined.

TABLE 10

CRISPR Fusion Proteins

SpCas9-HMGB1 box A fusion (SEQ ID NO: 61)
MDKKYSIGLDIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKILTFRI
PYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKIVDELVKVMGHKPENIVIEMARENQT
TQKGQKNSRERMKRIEEGIKELGSQILKEHPVENTQLQNEKLYLYYLQNGRDMYVDQELDINRL
SDYDVDHIVPQSFIKDDSIDNKVLTRSDKNRGKSDNVPSEEVVKKMKNYWRQLLNAKLITQRKF
DNLTKAERGGLSELDKAGFIKRQLVETRQITKHVAQILDSRMNTKYDENDKLIREVKVITLKSK
LVSDFRKDFQFYKVREINNYHHAHDAYLNAVVGTALIKKYPKLESEFVYGDYKVYDVRKMIAKS
EQEIGKATAKYFFYSNIMNFFKTEITLANGEIRKRPLIETNGETGEIVWDKGRDFATVRKVLSM
PQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASA
GELQKGNELALPSKYVNFLYLASHYEKLKGSPEDNEQKQLFVEQHKYLDEIIEQISEFSKRVI
LADANLDKVLSAYNKHRDKPIREQAENIIHLFTLTNLGAPAAFKYFDTTIDRKRYTSTKEVLDA
TLIHQSITGLYETRIDLSQLGGDPKKKRKVLEGGGGSMGKGDPKKPRGKMSSYAFFVQTCREEH
KKKHPDASVNFSEFSKKCSERWKTMSAKEKGKFEDMAKADKARYEREMKTYIPPKGE SpCas9-HMGN1 fusion (SEQ ID NO: 62)
MDKKYSIGLDIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKILTFRI
PYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKIVDELVKVMGHKPENIVIEMARENQT
TQKGQKNSRERMKRIEEGIKELGSQILKEHPVENTQLQNEKLYLYYLQNGRDMYVDQELDINRL
SDYDVDHIVPQSFIKDDSIDNKVLTRSDKNRGKSDNVPSEEVVKKMKNYWRQLLNAKLITQRKF
DNLTKAERGGLSELDKAGFIKRQLVETRQITKHVAQILDSRMNTKYDENDKLIREVKVITLKSK
LVSDFRKDFQFYKVREINNYHHAHDAYLNAVVGTALIKKYPKLESEFVYGDYKVYDVRKMIAKS
EQEIGKATAKYFFYSNIMNFFKTEITLANGEIRKRPLIETNGETGEIVWDKGRDFATVRKVLSM
PQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASA
GELQKGNELALPSKYVNFLYLASHYEKLKGSPEDNEQKQLFVEQHKYLDEIIEQISEFSKRVI
LADANLDKVLSAYNKHRDKPIREQAENIIHLFTLTNLGAPAAFKYFDTTIDRKRYTSTKEVLDA
TLIHQSITGLYETRIDLSQLGGDPKKKRKVLEGGGGSMPKRKVSSAEGAAKEEPKRRSARLSAK
PPAKVEAKPKKAAAKDKSSDKKVQTKGKRGAKGKQAEVANQETKEDLPAENGETKTEESPASDE
AGEKEAKSD SpCas9-HMGN2 fusion (SEQ ID NO: 63)
MDKKYSIGLDIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKILTFRI
PYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKIVDELVKVMGHKPENIVIEMARENQT
TQKGQKNSRERMKRIEEGIKELGSQILKEHPVENTQLQNEKLYLYYLQNGRDMYVDQELDINRL
SDYDVDHIVPQSFIKDDSIDNKVLTRSDKNRGKSDNVPSEEVVKKMKNYWRQLLNAKLITQRKF TABLE 10-continued CRISPR Fusion Proteins DNLTKAERGGLSELDKAGFIKRQLVETRQITKHVAQILDSRMNTKYDENDKLIREVKVITLKSK
LVSDFRKDFQFYKVREINNYHHAHDAYLNAVVGTALIKKYPKLESEFVYGDYKVYDVRKMIAKS
EQEIGKATAKYFFYSNIMNFFKTEITLANGEIRKRPLIETNGETGEIVWDKGRDFATVRKVLSM
PQVNIVKKTEVQTGGFSKESILPKRNSDKLIARKKDWDPKKYGGFDSPTVAYSVLVVAKVEGK
SKKLKSVKELLGITIMERSSFEKNPIDFLEAKGYKEVKKDLIIKLPKYSLFELENGRKRMLASA
GELQKGNELALPSKYVNFLYLASHYEKLKGSPEDNEQKQLFVEQHKHYLDEIIEQISEFSKRVI
LADANLDKVLSAYNKHRDKPIREQAENIIHLFTLTNLGAPAAFKYFDTTIDRKRYTSTKEVLDA
TLIHQSITGLYETRIDLSQLGGDPKKKRKVLEGGGGSMPKRKAEGDAKGDKAKVKDEPQRRSAR
LSAKPAPPKPEPKPKKAPAKKGEKVPKGKKGKADAGKEGNNPAENGDAKTDQAQKAEGAGDAK SpCas9-HMGN3a fusion (SEQ ID NO: 64)
MDKKYSIGLDIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKILTFRI
PYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKIVDELVKVMGHKPENIVIEMARENQT
TQKGQKNSRERMKRIEEGIKELGSQILKEHPVENTQLQNEKLYLYYLQNGRDMYVDQELDINRL
SDYDVDHIVPQSFIKDDSIDNKVLTRSDKNRGKSDNVPSEEVVKKMKNYWRQLLNAKLITQRKF
DNLTKAERGGLSELDKAGFIKRQLVETRQITKHVAQILDSRMNTKYDENDKLIREVKVITLKSK
LVSDFRKDFQFYKVREINNYHHAHDAYLNAVVGTALIKKYPKLESEFVYGDYKVYDVRKMIAKS
EQEIGKATAKYFFYSNIMNFFKTEITLANGEIRKRPLIETNGETGEIVWDKGRDFATVRKVLSM
PQVNIVKKTEVQTGGFSKESILPKRNSDKLIARKKDWDPKKYGGFDSPTVAYSVLVVAKVEGK
SKKLKSVKELLGITIMERSSFEKNPIDFLEAKGYKEVKKDLIIKLPKYSLFELENGRKRMLASA
GELQKGNELALPSKYVNFLYLASHYEKLKGSPEDNEQKQLFVEQHKHYLDEIIEQISEFSKRVI
LADANLDKVLSAYNKHRDKPIREQAENIIHLFTLTNLGAPAAFKYFDTTIDRKRYTSTKEVLDA
TLIHQSITGLYETRIDLSQLGGDPKKKRKVLEGGGGSMPKRKSPENTEGKDGSKVTKQEPTRRS
ARLSAKPAPPKPEPKPRKTSAKKEPGAKISRGAKGKKEEKQEAGKEGTAPSENGETKAEEAQKT
ESVDNEGE SpCas9-HMGN3b fusion (SEQ ID NO: 65)
MDKKYSIGLDIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKILTFRI
PYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKIVDELVKVMGHKPENIVIEMARENQT
TQKGQKNSRERMKRIEEGIKELGSQILKEHPVENTQLQNEKLYLYYLQNGRDMYVDQELDINRL
SDYDVDHIVPQSFIKDDSIDNKVLTRSDKNRGKSDNVPSEEVVKKMKNYWRQLLNAKLITQRKF
DNLTKAERGGLSELDKAGFIKRQLVETRQITKHVAQILDSRMNTKYDENDKLIREVKVITLKSK
LVSDFRKDFQFYKVREINNYHHAHDAYLNAVVGTALIKKYPKLESEFVYGDYKVYDVRKMIAKS
EQEIGKATAKYFFYSNIMNFFKTEITLANGEIRKRPLIETNGETGEIVWDKGRDFATVRKVLSM
PQVNIVKKTEVQTGGFSKESILPKRNSDKLIARKKDWDPKKYGGFDSPTVAYSVLVVAKVEGK
SKKLKSVKELLGITIMERSSFEKNPIDFLEAKGYKEVKKDLIIKLPKYSLFELENGRKRMLASA
GELQKGNELALPSKYVNFLYLASHYEKLKGSPEDNEQKQLFVEQHKHYLDEIIEQISEFSKRVI
LADANLDKVLSAYNKHRDKPIREQAENIIHLFTLTNLGAPAAFKYFDTTIDRKRYTSTKEVLDA
TLIHQSITGLYETRIDLSQLGGDPKKKRKVLEGGGGSMPKRKSPENTEGKDGSKVTKQEPTRRS
ARLSAKPAPPKPEPKPRKTSAKKEPGAKISRGAKGKKEEKQEAGKEGTEN SpCas9-Histone H1 globular fusion (SEQ ID NO: 66)
MDKKYSIGLDIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKILTFRI
PYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKIVDELVKVMGHKPENIVIEMARENQT
TQKGQKNSRERMKRIEEGIKELGSQILKEHPVENTQLQNEKLYLYYLQNGRDMYVDQELDINRL
SDYDVDHIVPQSFIKDDSIDNKVLTRSDKNRGKSDNVPSEEVVKKMKNYWRQLLNAKLITQRKF
DNLTKAERGGLSELDKAGFIKRQLVETRQITKHVAQILDSRMNTKYDENDKLIREVKVITLKSK
LVSDFRKDFQFYKVREINNYHHAHDAYLNAVVGTALIKKYPKLESEFVYGDYKVYDVRKMIAKS TABLE 10-continued CRISPR Fusion Proteins EQEIGKATAKYFFYSNIMNFFKTEITLANGEIRKRPLIETNGETGEIVWDKGRDFATVRKVLSM
PQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASA
GELQKGNELALPSKYVNFLYLASHYEKLKGSPEDNEQKQLFVEQHKHYLDEIIEQISEFSKRVI
LADANLDKVLSAYNKHRDKPIREQAENIIHLFTLTNLGAPAAFKYFDTTIDRKRYTSTKEVLDA
TLIHQSITGLYETRIDLSQLGGDPKKKRKVLEGGGGSSTDHPKYSDMIVAAIQAEKNRAGSSRQ
SIQKYIKSHYKVGENADSQIKLSIKRLVTTGVLKQTKGVGASGSFRLAKSDEP ISWI-SpCas9 fusion (SEQ ID NO: 67)
LLNPTKRERKENYSIDNYYKDVLNTGRSSTPSHPRMPKPHVFHSHQLQPPQLKVLYEKERMWTA
KKTGYVPTMDDVKAAYGDISDEEEKKQKLELLKLSVNNSQPLTEEEEKMKADWESEGFTNWNKL
EFRKFITVSGKYGRNSIQAIARELAPGKTLEEVRAYAKAFWSNIERIEDYEKYLKIIENEEEKI
KRVKMQQEALRRKLSEYKNPFFDLKLKHPPSSNNKRTYSEEEDRFILLMLFKYGLDRDDVYELV
RDEIRDCPLFELDFYFRSRTPVELARRGNTLLQCLEKEFNAGIVLDDATKDRMKKEDENGKRIR
EEFADQTANEKENVDGVESKKAKIEDTSNVGTEQLVAEKIPENETTHTGSGMDKKYSIGLDIGT
NSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKK
LVDSTDKADLRLIYLALAHMIKFRGHFLIEGDLNPDNSDVDKLFIQLVQTYNQLFEENPINASG
VDAKAILSARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDEHHQDLT
LLKALVRQQLPEKYKEIFFDQSKNGYAGYIDGGASQEEFYKFIKPILEKMDGTEELLVKLNRED
LLRKQRTFDNGSIPHQIHLGELHAILRRQEDFYPFLKDNREKIEKILTFRIPYYVGPLARGNSR
FAWMTRKSEETITPWNFEEVVDKGASAQSFIERMTNFDKNLPKVLPKHSLLYEYFTVYNELT
KVKYVTEGMRKPAFLSGEQKKAIVDLLFKTNRKVTVKQLKEDYFKKIECFDSVEISGVEDRFNA
SLGTYHDLLKIIKDKDFLDNEENEDILEDIVLTLTLFEDREMIEERLKTYAHLFDDKVMKQLKR
RRYTGWGRLSRKLINGIRDKQSGKTILDFLKSDGFANRNFMQLIHDDSLTFKEDIQKAQVSGQG
DSLHEHIANLAGSPAIKKGILQTVKIVDELVKVMGHKPENIVIEMARENQTTQKGQKNSRERMK
RIEEGIKELGSQILKEHPVENTQLQNEKLYLYYLQNGRDMYVDQELDINRLSDYDVDHIVPQSF
IKDDSIDNKVLTRSDKNRGKSDNVPSEEVVKKMKNYWRQLLNAKLITQRKFDNLTKAERGGLSE
LDKAGFIKRQLVETRQITKHVAQILDSRMNTKYDENDKLIREVKVITLKSKLVSDFRKDFQYFK
VREINNYHHAHDAYLNAVVGTALIKKYPKLESEFVYGDYKVYDVRKMIAKSEQEIGKATAKYFF
YSNIMNFFKTEITLANGEIRKRPLIETNGETGEIVWDKGRDFATVRKVLSMPQVNIVKKTEVQT
GGFSKESILPKRNSDKLIARKKDWDPKKYGGFDSPTVAYSVLVVAKVEKGKSKKLKSVKELLGI
TIMERSSFEKNPIDFLEAKGYKEVKKDLIIKLPKYSLFELENGRKRMLASAGELQKGNELALPS
KYVNFLYLASHYEKLKGSPEDNEQKQLFVEQHKHYLDEIIEQISEFSKRVILADANLDKVLSAY
NKHRDKPIREQAENIIHLFTLTNLGAPAAFKYFDTTIDRKRYTSTKEVLDATLIHQSITGLYET
RIDLSQLGGDPKKKRKV SpCas9-CHD1 fusion (SEQ ID NO: 68)
MDKKYSIGLDIGTNSVGWAVITDEYKVPSKKFKVLGNTDRHSIKKNLIGALLFDSGETAEATRL
KRTARRRYTRRKNRICYLQEIFSNEMAKVDDSFFHRLEESFLVEEDKKHERHPIFGNIVDEVAY
HEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSLGLTPNFKSNF
DLAEDAKLQLSKDTYDDDLDNLLAQIGDQYADLFLAAKNLSDAILLSDILRVNTEITKAPLSAS
MIKRYDEHHQDLTLLKALVRQQLPEKYKEIFFDQSKNGYAGYIDGGASQEEFYKFIKPILEKMD
GTEELLVKLNREDLLRKQRTFDNGSIPHQIHLGELHAILRRQEDFYPFLKDNREKIEKILTFRI
PYYVGPLARGNSRFAWMTRKSEETITPWNFEEVVDKGASAQSFIERMTNFDKNLPNEKVLPKHS
LLYEYFTVYNELTKVKYVTEGMRKPAFLSGEQKKAIVDLLFKTNRKVTVKQLKEDYFKKIECFD
SVEISGVEDRFNASLGTYHDLLKIIKDKDFLDNEENEDILEDIVLTLTLFEDREMIEERLKTYA
HLFDDKVMKQLKRRRYTGWGRLSRKLINGIRDKQSGKTILDFLKSDGFANRNFMQLIHDDSLTF
KEDIQKAQVSGQGDSLHEHIANLAGSPAIKKGILQTVKIVDELVKVMGHKPENIVIEMARENQT
TQKGQKNSRERMKRIEEGIKELGSQILKEHPVENTQLQNEKLYLYYLQNGRDMYVDQELDINRL
SDYDVDHIVPQSFIKDDSIDNKVLTRSDKNRGKSDNVPSEEVVKKMKNYWRQLLNAKLITQRKF
DNLTKAERGGLSELDKAGFIKRQLVETRQITKHVAQILDSRMNTKYDENDKLIREVKVITLKSK
LVSDFRKDFQYFKVREINNYHHAHDAYLNAVVGTALIKKYPKLESEFVYGDYKVYDVRKMIAKS
EQEIGKATAKYFFYSNIMNFFKTEITLANGEIRKRPLIETNGETGEIVWDKGRDFATVRKVLSM
PQVNIVKKTEVQTGGFSKESILPKRNSDKLIARKKDWDPKKYGGFDSPTVAYSVLVVAKVEKGK
SKKLKSVKELLGITIMERSSFEKNPIDFLEAKGYKEVKKDLIIKLPKYSLFELENGRKRMLASA
GELQKGNELALPSKYVNFLYLASHYEKLKGSPEDNEQKQLFVEQHKHYLDEIIEQISEFSKRVI
LADANLDKVLSAYNKHRDKPIREQAENIIHLFTLTNLGAPAAFKYFDTTIDRKRYTSTKEVLDA
TLIHQSITGLYETRIDLSQLGGDPKKKRKVLEGGGGSDMDSIGESEVRALYKAILKFGNLKEIL
DELIADGTLPVKSFEKYGETYDEMMEAAKDCVHEEEKNRKEILEKLEKHATAYRAKLKSGEIKA
ENQPKDNPLTRLSLKKREKKAVLFNFKGVKSLNAESLLSRVEDLKYLKNLINSNYKDDPLKFSL
GNNTPKPVQNWSSNWTKEEDEKLLIGVFKYGYGSWTQIRDDPFLGITDKIFLNEVHNPVAKKSA
SSSDTTPTPSKKGKITGSSKKVPGAIHLGRRVDYLLSFLRGGLNTKSPS HMGN1-SpCas9-HMGB1 box A fusion (SEQ ID NO: 69)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMDKKYSIGLDIGTNSVGWAVITDE
YKVPSKKFKVLGNTDRHSIKKNLIGALLFDSGETAEATRLKRTARRRYTRRKNRICYLQEIFSN
EMAKVDDSFFHRLEESFLVEEDKKHERHPIFGNIVDEVAYHEKYPTIYHLRKKLVDSTDKADLR
LIYLALAHMIKFRGHFLIEGDLNPDNSDVDKLFIQLVQTYNQLFEENPINASGVDAKAILSARL
SKSRRLENLIAQLPGEKKNGLFGNLIALSLGLTPNFKSNFDLAEDAKLQLSKDTYDDDLDNLLA
QIGDQYADLFLAAKNLSDAILLSDILRVNTEITKAPLSASMIKRYDEHHQDLTLLKALVRQQLP
EKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVTEGMRK
PAFLSGEQKKAIVDLLFKTNRKVTVKQLKEDYFKKIECFDSVEISGVEDRFNASLGTYHDLLKI TABLE 10-continued CRISPR Fusion Proteins IKDKDFLDNEENEDILEDIVLTLTLFEDREMIEERLKTYAHLFDDKVMKQLKRRRYTGWGRLSR
KLINGIRDKQSGKTILDFLKSDGFANRNFMQLIHDDSLTFKEDIQKAQVSGQGDSLHEHIANLA
GSPAIKKGILQTVKIVDELVKVMGHKPENIVIEMARENQTTQKGQKNSRERMKRIEEGIKELGS
QILKEHPVENTQLQNEKLYLYYLQNGRDMYVDQELDINRLSDYDVDHIVPQSFIKDDSIDNKVL
TRSDKNRGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNFFKTE
ITLANGEIRKRPLIETNGETGEIVWDKGRDFATVRKVLSMPQVNIVKKTEVQTGGFSKESILPK
RNSDKLIARKKDWDPKKYGGFDSPTVAYSVLVVAKVEKGKSKKLKSVKELLGITIMERSSFEKN
PIDFLEAKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDKPIREQ
AENIIHLFTLTNLGAPAAFKYFDTTIDRKRYTSTKEVLDATLIHQSITGLYETRIDLSQLGGDP
KKKRKVLEGGGGSGKGDPKKPRGKMSSYAFFVQTCREEHKKKHPDASVNFSEFSKKCSERWKTM
SAKEKGKFEDMAKADKARYEREMKTYIPPKGE HMGN1-SpCas9-Histone H1 globular fusion (SEQ ID NO: 70)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMDKKYSIGLDIGTNSVGWAVITDE
YKVPSKKFKVLGNTDRHSIKKNLIGALLFDSGETAEATRLKRTARRRYTRRKNRICYLQEIFSN
EMAKVDDSFFHRLEESFLVEEDKKHERHPIFGNIVDEVAYHEKYPTIYHLRKKLVDSTDKADLR
LIYLALAHMIKFRGHFLIEGDLNPDNSDVDKLFIQLVQTYNQLFEENPINASGVDAKAILSARL
SKSRRLENLIAQLPGEKKNGLFGNLIALSLGLTPNFKSNFDLAEDAKLQLSKDTYDDDLDNLLA
QIGDQYADLFLAAKNLSDAILLSDILRVNTEITKAPLSASMIKRYDEHHQDLTLLKALVRQQLP
EKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVTEGMRK
PAFLSGEQKKAIVDLLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQLKRRRYTGWGRLSR
KLINGIRDKQSGKTILDFLKSDGFANRNFMQLIHDDSLTFKEDIQKAQVSGQGDSLHEHIANLA
GSPAIKKGILQTVKIVDELVKVMGHKPENIVIEMARENQTTQKGQKNSRERMKRIEEGIKELGS
QILKEHPVENTQLQNEKLYLYYLQNGRDMYVDQELDINRLSDYDVDHIVPQSFIKDDSIDNKVL
TRSDKNRGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNFFKTE
ITLANGEIRKRPLIETNGETGEIVWDKGRDFATVRKVLSMPQVNIVKKTEVQTGGFSKESILPK
RNSDKLIARKKDWDPKKYGGFDSPTVAYSVLVVAKVEKGKSKKLKSVKELLGITIMERSSFEKN
PIDFLEAKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDKPIREQ
AENIIHLFTLTNLGAPAAFKYFDTTIDRKRYTSTKEVLDATLIHQSITGLYETRIDLSQLGGDP
KKKRKVLEGGGGSSTDHPKYSDMIVAAIQAEKNRAGSSRQSIQKYIKSHYKVGENADSQIKLSI
KRLVTTGVLKQTKGVGASGSFRLAKSDEP HMGN1-SpCas9-CDH1 fusion (SEQ ID NO: 71)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMDKKYSIGLDIGTNSVGWAVITDE
YKVPSKKFKVLGNTDRHSIKKNLIGALLFDSGETAEATRLKRTARRRYTRRKNRICYLQEIFSN
EMAKVDDSFFHRLEESFLVEEDKKHERHPIFGNIVDEVAYHEKYPTIYHLRKKLVDSTDKADLR
LIYLALAHMIKFRGHFLIEGDLNPDNSDVDKLFIQLVQTYNQLFEENPINASGVDAKAILSARL
SKSRRLENLIAQLPGEKKNGLFGNLIALSLGLTPNFKSNFDLAEDAKLQLSKDTYDDDLDNLLA
QIGDQYADLFLAAKNLSDAILLSDILRVNTEITKAPLSASMIKRYDEHHQDLTLLKALVRQQLP
EKYKEIFFDQSKNGYAGYIDGGASQEEFYKFIKPILEKMDGTEELLVKLNREDLLRKQRTFDNG
SIPHQIHLGELHAILRRQEDFYPFLKDNREKIEKILTFRIPYYVGPLARGNSRFAWMTRKSEET
ITPWNFEEVVDKGASAQSFIERMTNFDKNLPNEKVLPKHSLLYEYFTVYNELTKVKYVTEGMRK
PAFLSGEQKKAIVDLLFKTNRKVTVKQLKEDYFKKIECFDSVEISGVEDRFNASLGTYHDLLKI
IKDKDFLDNEENEDILEDIVLTLTLFEDREMIEERLKTYAHLFDDKVMKQLKRRRYTGWGRLSR
KLINGIRDKQSGKTILDFLKSDGFANRNFMQLIHDDSLTFKEDIQKAQVSGQGDSLHEHIANLA
GSPAIKKGILQTVKIVDELVKVMGHKPENIVIEMARENQTTQKGQKNSRERMKRIEEGIKELGS
QILKEHPVENTQLQNEKLYLYYLQNGRDMYVDQELDINRLSDYDVDHIVPQSFIKDDSIDNKVL
TRSDKNRGKSDNVPSEEVVKKMKNYWRQLLNAKLITQRKFDNLTKAERGGLSELDKAGFIKRQL
VETRQITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNFFKTE
ITLANGEIRKRPLIETNGETGEIVWDKGRDFATVRKVLSMPQVNIVKKTEVQTGGFSKESILPK
RNSDKLIARKKDWDPKKYGGFDSPTVAYSVLVVAKVEKGKSKKLKSVKELLGITIMERSSFEKN
PIDFLEAKGYKEVKKDLIIKLPKYSLFELENGRKRMLASAGELQKGNELALPSKYVNFLYLASH
YEKLKGSPEDNEQKQLFVEQHKHYLDEIIEQISEFSKRVILADANLDKVLSAYNKHRDKPIREQ
AENIIHLFTLTNLGAPAAFKYFDTTIDRKRYTSTKEVLDATLIHQSITGLYETRIDLSQLGGDP
KKKRKVLEGGGGSDMDSIGESEVRALYKAILKFGNLKEILDELIADGTLPVKSFEKYGETYDEM
MEAAKDCVHEEEKNRKEILEKLEKHATAYRAKLKSGEIKAENQPKDNPLTRLSLKKREKKAVLF
NPKGVKSLNAESLLSRVEDLKYLKNLINSNWTKDDPLKFSLGNNTPKPVQNWSSNWTKEEDEKLL
IGVFKYGYGSWTQIRDDPFLGITDKIFLNEVHNPVAKKSASSSDTTPTPSKKGKGITGSSKKVP
GAIHLGRRVDYLLSFLRGGLNTKSPS HMGN1-SpaCas9-HMGB1 box A fusion (SEQ ID NO: 72)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMTNGKILGLDIGIASVGVGIIEAK
TGKVVHANSRLFSAANAENNAERRGFRGSRRLNRRKKHRVKRVRDLFEKYGIVTDFRNLNLNPY
ELRVKGLTEQLKNEELFAALRTISKRRGISYLDDAEDDSTGSTDYAKSIDENRRLLKNKTPGQI
QLERLEKYGQLRGNFTVYDENGEAHRLINVFSTSDYEKEARKILETQADYNKKITAEFIDDYVE TABLE 10-continued CRISPR Fusion Proteins ILTQKRKYYHGPGNEKSRTDYGRFRTDGTTLENIFGILIGKCNFYPDEYRASKASYTAQEYNFL
NDLNNLKVSTETGKLSTEQKESLVEFAKNTATLGPAKLLKEIAKILDCKVDEIKGYREDDKGKP
DLHTFEPYRKLKFNLESINIDDLSREVIDKLADILTLNTEREGIEDAIKRNLPNQFTEEQISEI
IKVRSQSTAFNKGWHSFSAKLMNELIPELYATSDEQMTILTRLEKFKVNKKSSKNTKTIDEKE
VTDEIYNPVVAKSVRQTIKIINAAVKKYGDFDKIVIEMPRDKNADDEKKFIDKRNKENKKEKDD
ALKRAAYLYNSSDKLPDEVFHGNKQLETKIRLWYQQGERCLYSGKPISIQELVHNSNNFEIDHI
LPLSLSFDDSLANKVLVYAWTNQEKGQKTPYQVIDSMDAAWSFREMKDYVLKQGKLGKKKRDYL
LTTENIDKIEVKKKFIERNLVDTRYASRVVLNSLQSALRELGKDTKVSVVRGQFTSQLRRKWKI
DKSRETYHHHAVDALIIAASSQLKLWEKQDNPMFVDYGKNQVVDKQTGEILSVSDDEYKELVFQ
PPYQGFVNTISSKGFEDEILFSYQVDSKYNRKVSDATIYSTRKAKIGKDKKEETYVLGKIKDIY
SQNGFDTFIKKYNKDKTQFLMYQKDSLTWENVIEVILRDYPTTKKSEDGKNDVKCNPFEEYRRE
NGLICKYSKKGKGTPIKSLKYYDKKLGNCIDITPEESRNKVILQSINPWRADVYFNPETLKYEL
MGLKYSDLSFEKGTGNYHISQEKYDAIKEKEGIGKKSEFKFTLYRNDLILIKDIASGEQEIYRF
LSRTMPNVNHYVELKPYDKEKFDNVQELVEALGEADKVGRCIKGLNKPNISIYKVRTDVLGNKY
FVKKKGDKPKLDFKNNKKPKKKRKVLEGGGGSGKGDPKKPRGKMSSYAFFVQTCREEHKKKHPD
ASVNFSEFSKKCSERWKTMSAKEKGKFEDMAKADKARYEREMKTYIPPKGE HMGN1-SpaCas9-Histone H1 globular fusion (SEQ ID NO: 73)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMTNGKILGLDIGIASVGVGIIEAK
TGKVVHANSRLFSAANAENNAERRGFRGSRRLNRRKKHRVKRVRDLFEKYGIVTDFRNLNLNPY
ELRVKGLTEQLKNEELFAALRTISKRRGISYLDDAEDDSTGSTDYAKSIDENRRLLKNKTPGQI
QLERLEKYGQLRGNFTVYDENGEAHRLINVFSTSDYEKEARKILETQADYNKKITAEFIDDYVE
ILTQKRKYYHGPGNEKSRTDYGRFRTDGTTLENIFGILIGKCNFYPDEYRASKASYTAQEYNFL
NDLNNLKVSTETGKLSTEQKESLVEFAKNTATLGPAKLLKEIAKILDCKVDEIKGYREDDKGKP
DLHTFEPYRKLKFNLESINIDDLSREVIDKLADILTLNTEREGIEDAIKRNLPNQFTEEQISEI
IKVRSQSTAFNKGWHSFSAKLMNELIPELYATSDEQMTILTRLEKFKVNKKSSKNTKTIDEKE
VTDEIYNPVVAKSVRQTIKIINAAVKKYGDFDKIVIEMPRDKNADDEKKFIDKRNKENKKEKDD
ALKRAAYLYNSSDKLPDEVFHGNKQLETKIRLWYQQGERCLYSGKPISIQELVHNSNNFEIDHI
LPLSLSFDDSLANKVLVYAWTNQEKGQKTPYQVIDSMDAAWSFREMKDYVLKQGKLGKKKRDYL
LTTENIDKIEVKKKFIERNLVDTRYASRVVLNSLQSALRELGKDTKVSVVRGQFTSQLRRKWKI
DKSRETYHHHAVDALIIAASSQLKLWEKQDNPMFVDYGKNQVVDKQTGEILSVSDDEYKELVFQ
PPYQGFVNTISSKGFEDEILFSYQVDSKYNRKVSDATIYSTRKAKIGKDKKEETYVLGKIKDIY
SQNGFDTFIKKYNKDKTQFLMYQKDSLTWENVIEVILRDYPTTKKSEDGKNDVKCNPFEEYRRE
NGLICKYSKKGKGTPIKSLKYYDKKLGNCIDITPEESRNKVILQSINPWRADVYFNPETLKYEL
MGLKYSDLSFEKGTGNYHISQEKYDAIKEKEGIGKKSEFKFTLYRNDLILIKDIASGEQEIYRF
LSRTMPNVNHYVELKPYDKEKFDNVQELVEALGEADKVGRCIKGLNKPNISIYKVRTDVLGNKY
FVKKKGDKPKLDFKNNKKPKKKRKVLEGGGGSSTDHPKYSDMIVAAIQAEKNRAGSSRQSIQKY
IKSHYKVGENADSQIKLSIKRLVTTGVLKQTKGVGASGSFRLAKSDEP HMGN1-SpaCas9-CHD1 fusion (SEQ ID NO: 74)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMTNGKILGLDIGIASVGVGIIEAK
TGKVVHANSRLFSAANAENNAERRGFRGSRRLNRRKKHRVKRVRDLFEKYGIVTDFRNLNLNPY
ELRVKGLTEQLKNEELFAALRTISKRRGISYLDDAEDDSTGSTDYAKSIDENRRLLKNKTPGQI
QLERLEKYGQLRGNFTVYDENGEAHRLINVFSTSDYEKEARKILETQADYNKKITAEFIDDYVE
ILTQKRKYYHGPGNEKSRTDYGRFRTDGTTLENIFGILIGKCNFYPDEYRASKASYTAQEYNFL
NDLNNLKVSTETGKLSTEQKESLVEFAKNTATLGPAKLLKEIAKILDCKVDEIKGYREDDKGKP
DLHTFEPYRKLKFNLESINIDDLSREVIDKLADILTLNTEREGIEDAIKRNLPNQFTEEQISEI
IKVRSQSTAFNKGWHSFSAKLMNELIPELYATSDEQMTILTRLEKFKVNKKSSKNTKTIDEKE
VTDEIYNPVVAKSVRQTIKIINAAVKKYGDFDKIVIEMPRDKNADDEKKFIDKRNKENKKEKDD
ALKRAAYLYNSSDKLPDEVFHGNKQLETKIRLWYQQGERCLYSGKPISIQELVHNSNNFEIDHI
LPLSLSFDDSLANKVLVYAWTNQEKGQKTPYQVIDSMDAAWSFREMKDYVLKQGKLGKKKRDYL
LTTENIDKIEVKKKFIERNLVDTRYASRVVLNSLQSALRELGKDTKVSVVRGQFTSQLRRKWKI
DKSRETYHHHAVDALIIAASSQLKLWEKQDNPMFVDYGKNQVVDKQTGEILSVSDDEYKELVFQ
PPYQGFVNTISSKGFEDEILFSYQVDSKYNRKVSDATIYSTRKAKIGKDKKEETYVLGKIKDIY
SQNGFDTFIKKYNKDKTQFLMYQKDSLTWENVIEVILRDYPTTKKSEDGKNDVKCNPFEEYRRE
NGLICKYSKKGKGTPIKSLKYYDKKLGNCIDITPEESRNKVILQSINPWRADVYFNPETLKYEL
MGLKYSDLSFEKGTGNYHISQEKYDAIKEKEGIGKKSEFKFTLYRNDLILIKDIASGEQEIYRF
LSRTMPNVNHYVELKPYDKEKFDNVQELVEALGEADKVGRCIKGLNKPNISIYKVRTDVLGNKY
FVKKKGDKPKLDFKNNKKPKKKRKVLEGGGGSDMDSIGESEVRALYKAILKFGNLKEILDELIA
DGTLPVKSFEKYGETYDEMMEAAKDCVHEEEKNRKEILEKLEKHATAYRAKLKSGEIKAENQPK
DNPLTRLSLKKREKKAVLFNFKGVKSLNAESLLSRVEDLKYLKNLINSNYKDDPLKFSLGNNTP
KPVQNWSSNWTKEEDEKLLIGVFKYGYGSWTQIRDDPFLGITDKIFLNEVHNPVAKKSASSSDT
TPTPSKKGKITGSSKKVPGAIHLGRRVDYLLSFLRGGLNTKSPS HMGN1-FnCpf1-HNGB1 fusion (SEQ ID NO: 75)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMSIYQEFVNKYSLSKTLRFELIPQ
GKTLENIKARGLILDDEKRAKDYKKAKQIIDKYHQFFIEEILSSVCISEDLLQNYSDVYFKLKK
SDDDNLQKDFKSAKDTIKKQISEYIKDSEKFKNLFNQNLIDAKKGQESDLILWLKQSKDNGIEL
FKANSDITDIDEALEIIKSFKGWTTYFKGFHENRKNVYSSNDIPTSIIYRIVDDNLPKFLENKA
KYESLKDKAPEAINYEQIKKDLAEELTFDIDYKTSEVNQRVFSLDEVFEIANFNNYLNQSGITK
FNTIIGGKFVNGENTKRKGINEYINLYSQQINDKTLKKYKMSVLFKQILSDTESKSFVIDKLED
DSDVVTTMQSFYEQIAAFKTVEEKSIKETLSLLFDDLKAQKLDLSKIYFKNDKSLTDLSQQVFD
DYSVIGTAVLEYITQQIAPKNLDNPSKKEQELIAKKTEKAKYLSLETIKLALEEFNKHRDIDKQ
CRFEEILANFAAIPMIFDEIAQNKDNLAQISIKYQNQGKKDLLQASAEDDVKAIKDLLDQTNNL
LHKLKIFHISQSEDKANILDKDEHFYLVFEECYFELANIVPLYNKIRNYITQKPYSDEKFKLNF TABLE 10-continued CRISPR Fusion Proteins ENSTLANGWDKNKEPDNTAILFIKDDKYYLGVMNKKNNKIFDDKAIKENKGEGYKKIVYKLLPG
ANKMLPKVFFSAKSIKFYNPSEDILRIRNHSTHTKNGSPQKGYEKFEFNIEDCRKFIDFYKQSI
SKHPEWKDFGFRFSDTQRYNSIDEFYREVENQGYKLTFENISESYIDSVVNQGKLYLFQIYNKD
FSAYSKGRPNLHTLYWKALFDERNLQDVVYKLNGEAELFYRKQSIPKKITHPAKEAIANKNKDN
PKKESVFEYDLIKDKRFTEDKFFFHCPITINFKSSGANKFNDEINLLLKEKANDVHILSIDRGE
RHLAYYTLVDGKGNIIKQDTFNIIGNDRMKTNYHDKLAAIEKDRDSARKDWKKINNIKEMKEGY
LSQVVHEIAKLVIEYNAIVVFEDLNFGFKRGRFKVEKQVYQKLEKMLIEKLNYLVFKDNEFDKT
GGVLRAYQLTAPFETFKKMGKQTGIIYYVPAGFTSKICPVTGFVNQLYPKYESVSKSQEFFSKF
DKICYNLDKGYFEFSFDYKNFGDKAAKGKWTIASFGSRLINFRNSDKNHNWDTREVYPTKELEK
LLKDYSIEYGHGECIKAAICGESDKKFFAKLTSVLNTILQMRNSKTGTELDYLISPVADVNGNF
FDSRQAPKNMPQDADANGAYHIGLKGLMLLGRIKNNQEGKKLNLVIKNEEYFEFVQNRNNPKKK
RKVLEGGGGSGKGDPKKPRGKMSSYAFFVQTCREEHKKKHPDASVNFSEFSKKCSERWKTMSAK
EKGKFEDMAKADKARYEREMKTYIPPKGE HMGN1-FnCpf1-Histone H1 globular fusion (SEQ ID NO: 76)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMSIYQEFVNKYSLSKTLRFELIPQ
GKTLENIKARGLILDDEKRAKDYKKAKQIIDKYHQFFIEEILSSVCISEDLLQNYSDVYFKLKK
SDDDNLQKDFKSAKDTIKKQISEYIKDSEKFKNLFNQNLIDAKKGQESDLILWLKQSKDNGIEL
FKANSDITDIDEALEIIKSFKGWTTYFKGFHENRKNVYSSNDIPTSIIYRIVDDNLPKFLENKA
KYESLKDKAPEAINYEQIKKDLAEELTFDIDYKTSEVNQRVFSLDEVFEIANFNNYLNQSGITK
FNTIIGGKFVNGENTKRKGINEYINLYSQQINDKTLKKYKMSVLFKQILSDTESKSFVIDKLED
DSDVVTTMQSFYEQIAAFKTVEEKSIKETLSLLFDDLKAQKLDLSKIYFKNDKSLTDLSQQVFD
DYSVIGTAVLEYITQQIAPKNLDNPSKKEQELIAKKTEKAKYLSLETIKLALEEFNKHRDIDKQ
CRFEEILANFAAIPMIFDEIAQNKDNLAQISIKYQNQGKKDLLQASAEDDVKAIKDLLDQTNNL
LHKLKIFHISQSEDKANILDKDEHFYLVFEECYFELANIVPLYNKIRNYITQKPYSDEKFKLNF
ENSTLANGWDKNKEPDNTAILFIKDDKYYLGVMNKKNNKIFDDKAIKENKGEGYKKIVYKLLPG
ANKMLPKVFFSAKSIKFYNPSEDILRIRNHSTHTKNGSPQKGYEKFEFNIEDCRKFIDFYKQSI
SKHPEWKDFGFRFSDTQRYNSIDEFYREVENQGYKLTFENISESYIDSVVNQGKLYLFQIYNKD
FSAYSKGRPNLHTLYWKALFDERNLQDVVYKLNGEAELFYRKQSIPKKITHPAKEAIANKNKDN
PKKESVFEYDLIKDKRFTEDKFFFHCPITINFKSSGANKFNDEINLLLKEKANDVHILSIDRGE
RHLAYYTLVDGKGNIIKQDTFNIIGNDRMKTNYHDKLAAIEKDRDSARKDWKKINNIKEMKEGY
LSQVVHEIAKLVIEYNAIVVFEDLNFGFKRGRFKVEKQVYQKLEKMLIEKLNYLVFKDNEFDKT
GGVLRAYQLTAPFETFKKMGKQTGIIYYVPAGFTSKICPVTGFVNQLYPKYESVSKSQEFFSKF
DKICYNLDKGYFEFSFDYKNFGDKAAKGKWTIASFGSRLINFRNSDKNHNWDTREVYPTKELEK
LLKDYSIEYGHGECIKAAICGESDKKFFAKLTSVLNTILQMRNSKTGTELDYLISPVADVNGNF
FDSRQAPKNMPQDADANGAYHIGLKGLMLLGRIKNNQEGKKLNLVIKNEEYFEFVQNRNNPKKK
RKVLEGGGGSSTDHPKYSDMIVAAIQAEKNRAGSSRQSIQKYIKSHYKVGENADSQIKLSIKRL
VTTGVLKQTKGVGASGSFRLAKSDEP HMGN1-FnCpf1-CHD1 fusion (SEQ ID NO: 77)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMSIYQEFVNKYSLSKTLRFELIPQ
GKTLENIKARGLILDDEKRAKDYKKAKQIIDKYHQFFIEEILSSVCISEDLLQNYSDVYFKLKK
SDDDNLQKDFKSAKDTIKKQISEYIKDSEKFKNLFNQNLIDAKKGQESDLILWLKQSKDNGIEL
FKANSDITDIDEALEIIKSFKGWTTYFKGFHENRKNVYSSNDIPTSIIYRIVDDNLPKFLENKA
KYESLKDKAPEAINYEQIKKDLAEELTFDIDYKTSEVNQRVFSLDEVFEIANFNNYLNQSGITK
FNTIIGGKFVNGENTKRKGINEYINLYSQQINDKTLKKYKMSVLFKQILSDTESKSFVIDKLED
DSDVVTTMQSFYEQIAAFKTVEEKSIKETLSLLFDDLKAQKLDLSKIYFKNDKSLTDLSQQVFD
DYSVIGTAVLEYITQQIAPKNLDNPSKKEQELIAKKTEKAKYLSLETIKLALEEFNKHRDIDKQ
CRFEEILANFAAIPMIFDEIAQNKDNLAQISIKYQNQGKKDLLQASAEDDVKAIKDLLDQTNNL
LHKLKIFHISQSEDKANILDKDEHFYLVFEECYFELANIVPLYNKIRNYITQKPYSDEKFKLNF
ENSTLANGWDKNKEPDNTAILFIKDDKYYLGVMNKKNNKIFDDKAIKENKGEGYKKIVYKLLPG
ANKMLPKVFFSAKSIKFYNPSEDILRIRNHSTHTKNGSPQKGYEKFEFNIEDCRKFIDFYKQSI
SKHPEWKDFGFRFSDTQRYNSIDEFYREVENQGYKLTFENISESYIDSVVNQGKLYLFQIYNKD
FSAYSKGRPNLHTLYWKALFDERNLQDVVYKLNGEAELFYRKQSIPKKITHPAKEAIANKNKDN
PKKESVFEYDLIKDKRFTEDKFFFHCPITINFKSSGANKFNDEINLLLKEKANDVHILSIDRGE
RHLAYYTLVDGKGNIIKQDTFNIIGNDRMKTNYHDKLAAIEKDRDSARKDWKKINNIKEMKEGY
LSQVVHEIAKLVIEYNAIVVFEDLNFGFKRGRFKVEKQVYQKLEKMLIEKLNYLVFKDNEFDKT
GGVLRAYQLTAPFETFKKMGKQTGIIYYVPAGFTSKICPVTGFVNQLYPKYESVSKSQEFFSKF
DKICYNLDKGYFEFSFDYKNFGDKAAKGKWTIASFGSRLINFRNSDKNHNWDTREVYPTKELEK
LLKDYSIEYGHGECIKAAICGESDKKFFAKLTSVLNTILQMRNSKTGTELDYLISPVADVNGNF
FDSRQAPKNMPQDADANGAYHIGLKGLMLLGRIKNNQEGKKLNLVIKNEEYFEFVQNRNNPKKK
RKVLEGGGGSDMDSIGESEVRALYKAILKFGNLKEILDELIADGTLPVKSFEKYGETYDEMMEA
AKDCVHEEEKNRKEILEKLEKHATAYRAKLKSGEIKAENQPKDNPLTRLSLKKREKKAVLFNFK
GVKSLNAESLLSRVEDLKYLKNLINSNYKDDPLKFSLGNNTPKPVQNWSSNWTKEEDEKLLIGV
FKYGYGSWTQIRDDPFLGITDKIFLNEVHNPVAKKSASSSDTTPTPSKKGKGITGSSKKVPGAI
HLGRRVDYLLSFLRGGLNTKSPS HMGN1-CjCas9-HMGB1 box A fusion (SEQ ID NO: 78)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMARILAFDIGISSIGWAFSENDEL
KDCGVRIFTKVENPKTGESLALPRRLARSARKRLARRKARLNHLKHLIANEFKLNYEDYQSPDE
SLAKAYKGSLISPYELRFRALNELLSKQDFARVILHIAKRRGYDDIKNSDDKEKGAILKAIKQN
EEKLANYQSVGEYLYKEYFQKFKENSKEFTNVRNKKESYERCIAQSFLKDELKLIFKKQREFGF
SFSKKFEEEVLSVAFYKRALKDFSHLVGNCSFFTDEKRAPKNSPLAFMFVALTRIINLLNNLKN
TEGILYTKDDLNALLNEVLKNGTLTYKQTKKLLGLSDDYEFKGEKGTYFIEFKKYKEFIKALGE
HNLSQDDLNEIAKDITLIKDEIKLKKALAKYDLNQNQIDSLSKLEFKDHLNISFKALKLVTPLM

TABLE 10-continued

CRISPR Fusion Proteins

LEGKKYDEACNELNLKVAINEDKKDFLPAFNETYYKDEVTNPVVLRAIKEYRKVLNALLKKYGK
VHKINIELAREVGKNHSQRAKIEKEQNENYKAKKDAELECEKLGLKINSKNILKLRLFKEQKEF
CAYSGEKIKISDLQDEKMLEIDHIYPYSRSFDDSYMNKVLVFTKQNQEKLNQTPFEAFGNDSAK
WQKIEVLAKNLPTKKQKRILDKNYKDKEQKNFKDRNLNDTRYIARLVLNYTKDYLDFLPLSDDE
NTKLNDTQKGSKVHVEAKSGMLTSALRHTWGFSAKDRNNHLHHAIDAVIIAYANNSIVKAFSDF
KKEQESNSAELYAKKISELDYKNKRKFFEPFSGFRQKVLDKIDEIFVSKPERKKPSGALHEETF
RKEEEFYQSYGGKEGVLKALELGKIRKVNGKIVKNGDMFRVDIFKHKKTNKFYAVPIYTMDFAL
KVLPNKAVARSKKGEIKDWILMDENYEFCFSLYKDSLILIQTKDMQEPEFVYYNAFTSSTVSLI
VSKHDNKFETLSKNQKILFKNANEKEVIAKSIGIQNLKVFEKYIVSALGEVTKAEFRQREDFKK
PKKKRKVLEGGGGSGKGDPKKPRGKMSSYAFFVQTCREEHKKKHPDASVNFSEFSKKCSERWKT
MSAKEKGKFEDMAKADKARYEREMKTYIPPKGE

HMGN1-CjCas9-Histone H1 globular fusion (SEQ ID NO: 79)
MPKRKVSSAEGAAKEEPKRRSARLSAKPPAKVEAKPKKAAAKDKSSDKKVQTKGKRGAKGKQAE
VANQETKEDLPAENGETKTEESPASDEAGEKEAKSDTGSGMARILAFDIGISSIGWAFSENDEL
KDCGVRIFTKVENPKTGESLALPRRLARSARKRLARRKARLNHLKHLIANEFKLNYEDYQSFDE
SLAKAYKGSLISPYELRFRALNELLSKQDFARVILHIAKRRGYDDIKNSDDKEKGAILKAIKQN
EEKLANYQSVGEYLYKEYFQKFKENSKEFTNVRNKKESYERCIAQSFLKDELKLIFKKQREFGF
SFSKKFEEEVLSVAFYKRALKDFSHLVGNCSFFTDEKRAPKNSPLAFMFVALTRIINLLNNLKN
TEGILYTKDDLNALLNEVLKNGTLTYKQTKKLLGLSDDYEFKGEKGTYFIEFKKYKEFIKALGE
HNLSQDDLNEIAKDITLIKDEIKLKKALAKYDLNQNQIDSLSKLEFKDHLNISFKALKLVTPLM
LEGKKYDEACNELNLKVAINEDKKDFLPAFNETYYKDEVTNPVVLRAIKEYRKVLNALLKKYGK
VHKINIELAREVGKNHSQRAKIEKEQNENYKAKKDAELECEKLGLKINSKNILKLRLFKEQKEF
CAYSGEKIKISDLQDEKMLEIDHIYPYSRSFDDSYMNKVLVFTKQNQEKLNQTPFEAFGNDSAK
WQKIEVLAKNLPTKKQKRILDKNYKDKEQKNFKDRNLNDTRYIARLVLNYTKDYLDFLPLSDDE
NTKLNDTQKGSKVHVEAKSGMLTSALRHTWGFSAKDRNNHLHHAIDAVIIAYANNSIVKAFSDF
KKEQESNSAELYAKKISELDYKNKRKFFEPFSGFRQKVLDKIDEIFVSKPERKKPSGALHEETF
RKEEEFYQSYGGKEGVLKALELGKIRKVNGKIVKNGDMFRVDIFKHKKTNKFYAVPIYTMDFAL
KVLPNKAVARSKKGEIKDWILMDENYEFCFSLYKDSLILIQTKDMQEPEFVYYNAFTSSTVSLI
VSKHDNKFETLSKNQKILFKNANEKEVIAKSIGIQNLKVFEKYIVSALGEVTKAEFRQREDFKK
PKKKRKVLEGGGGSSTDHPKYSDMIVAAIQAEKNRAGSSRQSIQKYIKSHYKVGENADSQIKLS
IKRLVTTGVLKQTKGVGASGSFRLAKSDEP

What is claimed is:

1. A fusion protein comprising a clustered regularly interspersed short palindromic repeats (CRISPR) protein directly or indirectly linked to two nucleosome interacting protein domains,
    wherein the CRISPR protein is *Streptococcus pyogenes* Cas9 (SpCas9), *Streptococcus pasteurianus* Cas9 (SpaCas9), *Francisella novicida* Cpf1 (FnCpf1), or *Campylobacter jejuni* Cas9 (CjCas9),
    wherein one of the two nucleosome interacting protein domains is a high mobility group (HMG) nucleosome-binding (HMGN) protein, and the other of the two nucleosome interacting protein domains is a high mobility group (HMG) box (HMGB) protein, a central globular domain from a histone H1 variant comprising SEQ ID NO:45, or a DNA binding domain from a chromatin remodeling complex protein, and
    wherein the one of the two nucleosome interacting protein domains is directly or indirectly linked to the CRISPR protein at its N-terminus and the other of the two nucleosome interacting protein domains is directly or indirectly linked to the CRISPR protein at its C-terminus.

2. The fusion protein of claim 1, wherein one of the two nucleosome interacting protein domains is a HMGN1 protein, a HMGN2 protein, a HMGN3a protein, a HMGN3b protein, a HMGN4 protein, or a HMGN5 protein, and the other of the two nucleosome interacting protein domains is a HMGB1 box A domain, a central globular domain from a histone H1 variant comprising SEQ ID NO:45, or a chromodomain-helicase-DNA protein 1 (CHD1).

3. The fusion protein of claim 1, wherein the two nucleosome interacting protein domain(s) are each independently linked to the CRISPR protein directly via a chemical bond, or indirectly via a linker.

4. The fusion protein of claim 1, further comprising at least one nuclear localization signal, at least one cell-penetrating domain, at least one marker domain, or a combination thereof.

5. The fusion protein of claim 4, further comprising only one nuclear localization signal directly or indirectly linked to the CRISPR protein at its C-terminus.

6. The fusion protein of claim 3, wherein at least one of the two nucleosome interacting protein domains is indirectly linked to the CRISPR protein via a linker.

7. The fusion protein of claim 6, wherein the linker is LEGGGS (SEQ ID NO:1).

8. A composition comprising the fusion protein of claim 1, and a donor polynucleotide comprising a donor sequence flanked by an upstream sequence and a downstream sequence that permit homologous recombination between the donor polynucleotide and a target chromosomal sequence in a eukaryotic cell, such that the donor sequence can be integrated into or exchanged with the target chromosomal sequence.

9. A complex comprising a fusion protein of claim 1 and at least one guide RNA.

10. An in vitro eukaryotic cell comprising the fusion protein of claim 1.

11. The in vitro eukaryotic cell of claim 10, wherein the eukaryotic cell is a mammalian cell.

12. The in vitro eukaryotic cell of claim 10, wherein the eukaryotic cell is a human cell.

13. An in vitro eukaryotic cell comprising the composition of claim 8.

14. The in vitro eukaryotic cell of claim 13, wherein the eukaryotic cell is a mammalian cell.

15. The in vitro eukaryotic cell of claim 13, wherein the eukaryotic cell is a human cell.

16. The fusion protein of claim 1, wherein the fusion protein has at least 90% sequence identity with the sequence of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, or SEQ ID NO:79.

17. The fusion protein of claim 1, wherein the fusion protein has the amino acid sequence of SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, or SEQ ID NO:79.

18. A nucleic acid encoding a fusion protein comprising a CRISPR protein directly or indirectly linked to two nucleosome interacting protein domains, wherein the CRISPR protein is *Streptococcus pyogenes* Cas9 (SpCas9), *Streptococcus pasteurianus* Cas9 (SpaCas9), *Francisella novicida* Cpf1 (FnCpf1), or *Campylobacter jejuni* Cas9 (CjCas9), wherein one of the two nucleosome interacting protein domains is a HMGN protein, and the other of the two nucleosome interacting protein domains is a HMGB protein, a central globular domain from a histone H1 variant comprising SEQ ID NO:45, or a DNA binding domain from a chromatin remodeling complex protein, and wherein the one of the two nucleosome interacting protein domains is directly or indirectly linked to the CRISPR protein at its N-terminus and the other of the two nucleosome interacting protein domains is directly or indirectly linked to the CRISPR protein at its C-terminus.

19. The nucleic acid of claim 18, which is codon optimized for translation in a eukaryotic cell.

20. The nucleic acid of claim 18, which is part of a viral vector, a plasmid vector, or a self-replicating RNA.

* * * * *

SEQUENCE LISTING

```
<160> NUMBER OF SEQ ID NOS: 79

<210> SEQ ID NO 1
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 1

Leu Glu Gly Gly Gly Ser
1               5

<210> SEQ ID NO 2
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 2

Thr Gly Ser Gly
1

<210> SEQ ID NO 3
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 3

Gly Gly Ser Gly Gly Gly Ser Gly
```

```
1               5

<210> SEQ ID NO 4
<211> LENGTH: 20
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (6)..(20)
<223> OTHER INFORMATION: can be either absent or present

<400> SEQUENCE: 4

Gly Gly Gly Gly Ser Gly Gly Gly Gly Ser Gly Gly Gly Gly Ser Gly
1               5                   10                  15

Gly Gly Gly Ser
            20

<210> SEQ ID NO 5
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (7)..(8)
<223> OTHER INFORMATION: can be either absent or present)

<400> SEQUENCE: 5

Gly Gly Gly Gly Gly Gly Gly Gly
1               5

<210> SEQ ID NO 6
<211> LENGTH: 20
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (6)..(20)
<223> OTHER INFORMATION: can be either absent or present

<400> SEQUENCE: 6

Glu Ala Ala Ala Lys Glu Ala Ala Ala Lys Glu Ala Ala Ala Lys Glu
1               5                   10                  15

Ala Ala Ala Lys
            20

<210> SEQ ID NO 7
<211> LENGTH: 27
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (12)..(26)
<223> OTHER INFORMATION: can be either absent or present

<400> SEQUENCE: 7

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25
```

<210> SEQ ID NO 8
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 8

Pro Ala Pro Ala Pro
1               5

<210> SEQ ID NO 9
<211> LENGTH: 16
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (13)..(16)
<223> OTHER INFORMATION: can be either absent or present

<400> SEQUENCE: 9

Ala Pro Ala Pro Ala Pro Ala Pro Ala Pro Ala Pro Ala Pro Ala Pro
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 10

Pro Lys Lys Lys Arg Lys Val
1               5

<210> SEQ ID NO 11
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 11

Pro Lys Lys Lys Arg Arg Val
1               5

<210> SEQ ID NO 12
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 12

Lys Arg Pro Ala Ala Thr Lys Lys Ala Gly Gln Ala Lys Lys Lys Lys
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 13

Tyr Gly Arg Lys Lys Arg Arg Gln Arg Arg
1               5                   10

<210> SEQ ID NO 14
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 14

Arg Lys Lys Arg Arg Gln Arg Arg Arg
1               5

<210> SEQ ID NO 15
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 15

Pro Ala Ala Lys Arg Val Lys Leu Asp
1               5

<210> SEQ ID NO 16
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 16

Arg Gln Arg Arg Asn Glu Leu Lys Arg Ser Pro
1               5                   10

<210> SEQ ID NO 17
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 17

Val Ser Arg Lys Arg Pro Arg Pro
1               5

<210> SEQ ID NO 18
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 18

Pro Pro Lys Lys Ala Arg Glu Asp
1               5

<210> SEQ ID NO 19
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 19

Pro Gln Pro Lys Lys Lys Pro Leu

```
1               5

<210> SEQ ID NO 20
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 20

Ser Ala Leu Ile Lys Lys Lys Lys Lys Met Ala Pro
1               5                   10

<210> SEQ ID NO 21
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 21

Pro Lys Gln Lys Lys Arg Lys
1               5

<210> SEQ ID NO 22
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 22

Arg Lys Leu Lys Lys Lys Ile Lys Lys Leu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 23

Arg Glu Lys Lys Lys Phe Leu Lys Arg Arg
1               5                   10

<210> SEQ ID NO 24
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 24

Lys Arg Lys Gly Asp Glu Val Asp Gly Val Asp Glu Val Ala Lys Lys
1               5                   10                  15

Lys Ser Lys Lys
            20

<210> SEQ ID NO 25
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 25
```

Arg Lys Cys Leu Gln Ala Gly Met Asn Leu Glu Ala Arg Lys Thr Lys
1               5                   10                  15

Lys

<210> SEQ ID NO 26
<211> LENGTH: 38
<212> TYPE: PRT
<213> ORGANISM: Artificial Sequence
<220> FEATURE:
<223> OTHER INFORMATION: SYNTHESIZED

<400> SEQUENCE: 26

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 27
<211> LENGTH: 42
<212> TYPE: PRT
<213> ORGANISM: Artificial Sequence
<220> FEATURE:
<223> OTHER INFORMATION: SYNTHESIZED

<400> SEQUENCE: 27

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 28
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 28

Gly Arg Lys Lys Arg Arg Gln Arg Arg Arg Pro Pro Gln Pro Lys Lys
1               5                   10                  15

Lys Arg Lys Val
            20

<210> SEQ ID NO 29
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 29

Pro Leu Ser Ser Ile Phe Ser Arg Ile Gly Asp Pro Pro Lys Lys Lys
1               5                   10                  15

Arg Lys Val

<210> SEQ ID NO 30
<211> LENGTH: 24
<212> TYPE: PRT

```
<213> ORGANISM: Artificial Sequence
<220> FEATURE:
<223> OTHER INFORMATION: SYNTHESIZED

<400> SEQUENCE: 30

Gly Ala Leu Phe Leu Gly Trp Leu Gly Ala Ala Gly Ser Thr Met Gly
1               5                   10                  15

Ala Pro Lys Lys Lys Arg Lys Val
            20

<210> SEQ ID NO 31
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 31

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 32
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 32

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 33
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 33

Tyr Ala Arg Ala Ala Ala Arg Gln Ala Arg Ala
1               5                   10

<210> SEQ ID NO 34
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 34

Thr His Arg Leu Pro Arg Arg Arg Arg Arg
1               5                   10

<210> SEQ ID NO 35
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 35
```

```
Gly Gly Arg Arg Ala Arg Arg Arg Arg Arg
1               5                   10
```

<210> SEQ ID NO 36
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 36

```
Arg Arg Gln Arg Arg Thr Ser Lys Leu Met Lys Arg
1               5                   10
```

<210> SEQ ID NO 37
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 37

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 38
<211> LENGTH: 33
<212> TYPE: PRT
<213> ORGANISM: Artificial Sequence
<220> FEATURE:
<223> OTHER INFORMATION: SYNTHESIZED

<400> SEQUENCE: 38

```
Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala
```

<210> SEQ ID NO 39
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 39

```
Arg Gln Ile Lys Ile Trp Phe Gln Asn Arg Arg Met Lys Trp Lys Lys
1               5                   10                  15
```

<210> SEQ ID NO 40
<211> LENGTH: 84
<212> TYPE: PRT
<213> ORGANISM: Homo sapiens

<400> SEQUENCE: 40

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
```

```
                35                  40                  45
Trp Lys Thr Met Ser Ala Lys Glu Lys Gly Lys Phe Glu Asp Met Ala
 50                  55                  60
Lys Ala Asp Lys Ala Arg Tyr Glu Arg Glu Met Lys Thr Tyr Ile Pro
 65                  70                  75                  80
Pro Lys Gly Glu

<210> SEQ ID NO 41
<211> LENGTH: 100
<212> TYPE: PRT
<213> ORGANISM: Homo sapiens

<400> SEQUENCE: 41

Met Pro Lys Arg Lys Val Ser Ser Ala Glu Gly Ala Ala Lys Glu Glu
 1               5                  10                  15
Pro Lys Arg Arg Ser Ala Arg Leu Ser Ala Lys Pro Ala Lys Val
                20                  25                  30
Glu Ala Lys Pro Lys Ala Ala Ala Lys Asp Lys Ser Ser Asp Lys
                35                  40                  45
Lys Val Gln Thr Lys Gly Lys Arg Gly Ala Lys Gly Lys Gln Ala Glu
 50                  55                  60
Val Ala Asn Gln Glu Thr Lys Glu Asp Leu Pro Ala Glu Asn Gly Glu
 65                  70                  75                  80
Thr Lys Thr Glu Glu Ser Pro Ala Ser Asp Glu Ala Gly Glu Lys Glu
                85                  90                  95
Ala Lys Ser Asp
            100

<210> SEQ ID NO 42
<211> LENGTH: 90
<212> TYPE: PRT
<213> ORGANISM: Homo sapiens

<400> SEQUENCE: 42

Met Pro Lys Arg Lys Ala Glu Gly Asp Ala Lys Gly Asp Lys Ala Lys
 1               5                  10                  15
Val Lys Asp Glu Pro Gln Arg Arg Ser Ala Arg Leu Ser Ala Lys Pro
                20                  25                  30
Ala Pro Pro Lys Pro Glu Pro Lys Pro Lys Lys Ala Pro Ala Lys Lys
                35                  40                  45
Gly Glu Lys Val Pro Lys Gly Lys Lys Gly Lys Ala Asp Ala Gly Lys
 50                  55                  60
Glu Gly Asn Asn Pro Ala Glu Asn Gly Asp Ala Lys Thr Asp Gln Ala
 65                  70                  75                  80
Gln Lys Ala Glu Gly Ala Gly Asp Ala Lys
                85                  90

<210> SEQ ID NO 43
<211> LENGTH: 99
<212> TYPE: PRT
<213> ORGANISM: Homo sapiens

<400> SEQUENCE: 43

Met Pro Lys Arg Lys Ser Pro Glu Asn Thr Glu Gly Lys Asp Gly Ser
 1               5                  10                  15
Lys Val Thr Lys Gln Glu Pro Thr Arg Arg Ser Ala Arg Leu Ser Ala
                20                  25                  30
```

Lys Pro Ala Pro Pro Lys Pro Glu Pro Lys Pro Arg Lys Thr Ser Ala
                35                  40                  45

Lys Lys Glu Pro Gly Ala Lys Ile Ser Arg Gly Ala Lys Gly Lys Lys
 50                  55                  60

Glu Glu Lys Gln Glu Ala Gly Lys Gly Thr Ala Pro Ser Glu Asn
 65                  70                  75                  80

Gly Glu Thr Lys Ala Glu Ala Gln Lys Thr Glu Ser Val Asp Asn
             85                  90                  95

Glu Gly Glu

<210> SEQ ID NO 44
<211> LENGTH: 77
<212> TYPE: PRT
<213> ORGANISM: Homo sapiens

<400> SEQUENCE: 44

Met Pro Lys Arg Lys Ser Pro Glu Asn Thr Glu Gly Lys Asp Gly Ser
 1               5                  10                  15

Lys Val Thr Lys Gln Glu Pro Thr Arg Arg Ser Ala Arg Leu Ser Ala
             20                  25                  30

Lys Pro Ala Pro Pro Lys Pro Glu Pro Lys Pro Arg Lys Thr Ser Ala
                35                  40                  45

Lys Lys Glu Pro Gly Ala Lys Ile Ser Arg Gly Ala Lys Gly Lys Lys
 50                  55                  60

Glu Glu Lys Gln Glu Ala Gly Lys Gly Thr Glu Asn
 65                  70                  75

<210> SEQ ID NO 45
<211> LENGTH: 80
<212> TYPE: PRT
<213> ORGANISM: Homo sapiens

<400> SEQUENCE: 45

Ser Thr Asp His Pro Lys Tyr Ser Asp Met Ile Val Ala Ala Ile Gln
 1               5                  10                  15

Ala Glu Lys Asn Arg Ala Gly Ser Ser Arg Gln Ser Ile Gln Lys Tyr
             20                  25                  30

Ile Lys Ser His Tyr Lys Val Gly Glu Asn Ala Asp Ser Gln Ile Lys
             35                  40                  45

Leu Ser Ile Lys Arg Leu Val Thr Thr Gly Val Leu Lys Gln Thr Lys
 50                  55                  60

Gly Val Gly Ala Ser Gly Ser Phe Arg Leu Ala Lys Ser Asp Glu Pro
 65                  70                  75                  80

<210> SEQ ID NO 46
<211> LENGTH: 367
<212> TYPE: PRT
<213> ORGANISM: Saccharomyces cerevisiae

<400> SEQUENCE: 46

Leu Leu Asn Pro Thr Lys Arg Glu Arg Lys Glu Asn Tyr Ser Ile Asp
 1               5                  10                  15

Asn Tyr Tyr Lys Asp Val Leu Asn Thr Gly Arg Ser Ser Thr Pro Ser
             20                  25                  30

His Pro Arg Met Pro Lys Pro His Val Phe His Ser His Gln Leu Gln
             35                  40                  45

Pro Pro Gln Leu Lys Val Leu Tyr Glu Lys Glu Arg Met Trp Thr Ala
 50                  55                  60

Lys Lys Thr Gly Tyr Val Pro Thr Met Asp Asp Val Lys Ala Ala Tyr
65                  70                  75                  80

Gly Asp Ile Ser Asp Glu Glu Glu Lys Lys Gln Lys Leu Glu Leu Leu
                85                  90                  95

Lys Leu Ser Val Asn Asn Ser Gln Pro Leu Thr Glu Glu Glu Glu Lys
            100                 105                 110

Met Lys Ala Asp Trp Glu Ser Glu Gly Phe Thr Asn Trp Asn Lys Leu
        115                 120                 125

Glu Phe Arg Lys Phe Ile Thr Val Ser Gly Lys Tyr Gly Arg Asn Ser
    130                 135                 140

Ile Gln Ala Ile Ala Arg Glu Leu Ala Pro Gly Lys Thr Leu Glu Glu
145                 150                 155                 160

Val Arg Ala Tyr Ala Lys Ala Phe Trp Ser Asn Ile Glu Arg Ile Glu
                165                 170                 175

Asp Tyr Glu Lys Tyr Leu Lys Ile Ile Glu Asn Glu Glu Lys Ile
                180                 185                 190

Lys Arg Val Lys Met Gln Gln Glu Ala Leu Arg Arg Lys Leu Ser Glu
            195                 200                 205

Tyr Lys Asn Pro Phe Phe Asp Leu Lys Leu Lys His Pro Pro Ser Ser
210                 215                 220

Asn Asn Lys Arg Thr Tyr Ser Glu Glu Glu Asp Arg Phe Ile Leu Leu
225                 230                 235                 240

Met Leu Phe Lys Tyr Gly Leu Asp Arg Asp Asp Val Tyr Glu Leu Val
                245                 250                 255

Arg Asp Glu Ile Arg Asp Cys Pro Leu Phe Glu Leu Asp Phe Tyr Phe
                260                 265                 270

Arg Ser Arg Thr Pro Val Glu Leu Ala Arg Arg Gly Asn Thr Leu Leu
            275                 280                 285

Gln Cys Leu Glu Lys Glu Phe Asn Ala Gly Ile Val Leu Asp Asp Ala
    290                 295                 300

Thr Lys Asp Arg Met Lys Lys Glu Asp Glu Asn Gly Lys Arg Ile Arg
305                 310                 315                 320

Glu Glu Phe Ala Asp Gln Thr Ala Asn Glu Lys Glu Asn Val Asp Gly
                325                 330                 335

Val Glu Ser Lys Lys Ala Lys Ile Glu Asp Thr Ser Asn Val Gly Thr
            340                 345                 350

Glu Gln Leu Val Ala Glu Lys Ile Pro Glu Asn Glu Thr Thr His
        355                 360                 365

<210> SEQ ID NO 47
<211> LENGTH: 269
<212> TYPE: PRT
<213> ORGANISM: Saccharomyces cerevisiae

<400> SEQUENCE: 47

Asp Met Asp Ser Ile Gly Glu Ser Glu Val Arg Ala Leu Tyr Lys Ala
1               5                   10                  15

Ile Leu Lys Phe Gly Asn Leu Lys Glu Ile Leu Asp Glu Leu Ile Ala
            20                  25                  30

Asp Gly Thr Leu Pro Val Lys Ser Phe Glu Lys Tyr Gly Glu Thr Tyr
        35                  40                  45

Asp Glu Met Met Glu Ala Ala Lys Asp Cys Val His Glu Glu Glu Lys
    50                  55                  60

Asn Arg Lys Glu Ile Leu Glu Lys Leu Glu Lys His Ala Thr Ala Tyr

```
              65                  70                  75                  80
        Arg Ala Lys Leu Lys Ser Gly Glu Ile Lys Ala Glu Asn Gln Pro Lys
                            85                  90                  95

Asp Asn Pro Leu Thr Arg Leu Ser Leu Lys Arg Glu Lys Lys Ala
                        100                 105                 110

Val Leu Phe Asn Phe Lys Gly Val Lys Ser Leu Asn Ala Glu Ser Leu
                        115                 120                 125

Leu Ser Arg Val Glu Asp Leu Lys Tyr Leu Lys Asn Leu Ile Asn Ser
                    130                 135                 140

Asn Tyr Lys Asp Asp Pro Leu Lys Phe Ser Leu Gly Asn Asn Thr Pro
        145                 150                 155                 160

Lys Pro Val Gln Asn Trp Ser Ser Asn Trp Thr Lys Glu Glu Asp Glu
                            165                 170                 175

Lys Leu Leu Ile Gly Val Phe Lys Tyr Gly Tyr Gly Ser Trp Thr Gln
                        180                 185                 190

Ile Arg Asp Asp Pro Phe Leu Gly Ile Thr Asp Lys Ile Phe Leu Asn
                        195                 200                 205

Glu Val His Asn Pro Val Ala Lys Lys Ser Ala Ser Ser Ser Asp Thr
                    210                 215                 220

Thr Pro Thr Pro Ser Lys Lys Gly Lys Gly Ile Thr Gly Ser Ser Lys
        225                 230                 235                 240

Lys Val Pro Gly Ala Ile His Leu Gly Arg Arg Val Asp Tyr Leu Leu
                            245                 250                 255

Ser Phe Leu Arg Gly Gly Leu Asn Thr Lys Ser Pro Ser
                        260                 265
```

<210> SEQ ID NO 48
<211> LENGTH: 23
<212> TYPE: DNA
<213> ORGANISM: Homo sapiens

<400> SEQUENCE: 48
agccgtgagt ggagggagcg tgg                                           23

<210> SEQ ID NO 49
<211> LENGTH: 23
<212> TYPE: DNA
<213> ORGANISM: Homo sapiens

<400> SEQUENCE: 49
agagggaggg gttggactac agg                                           23

<210> SEQ ID NO 50
<211> LENGTH: 23
<212> TYPE: DNA
<213> ORGANISM: Homo sapiens

<400> SEQUENCE: 50
cattcgccag tacgagcttg tgg                                           23

<210> SEQ ID NO 51
<211> LENGTH: 23
<212> TYPE: DNA
<213> ORGANISM: Homo sapiens

<400> SEQUENCE: 51
ctttaatgcg ctgacttgtg agg                                           23

<210> SEQ ID NO 52
<211> LENGTH: 23
<212> TYPE: DNA
<213> ORGANISM: Homo sapiens

<400> SEQUENCE: 52
gtggcgcatt gccacgaagc agg                                          23

<210> SEQ ID NO 53
<211> LENGTH: 23
<212> TYPE: DNA
<213> ORGANISM: Homo sapiens

<400> SEQUENCE: 53
ttcttcttct gctcggactc agg                                          23

<210> SEQ ID NO 54
<211> LENGTH: 26
<212> TYPE: DNA
<213> ORGANISM: Homo sapiens

<400> SEQUENCE: 54
tgctggaaag gggagaccaa gggtga                                       26

<210> SEQ ID NO 55
<211> LENGTH: 26
<212> TYPE: DNA
<213> ORGANISM: Homo sapiens

<400> SEQUENCE: 55
agagctacga gaaccagaag ccgtga                                       26

<210> SEQ ID NO 56
<211> LENGTH: 26
<212> TYPE: DNA
<213> ORGANISM: Homo sapiens

<400> SEQUENCE: 56
ttcccggcct cacccttggt ctcccc                                       26

<210> SEQ ID NO 57
<211> LENGTH: 26
<212> TYPE: DNA
<213> ORGANISM: Homo sapiens

<400> SEQUENCE: 57
ttggtctccc ctttccagca ttcgcc                                       26

<210> SEQ ID NO 58
<211> LENGTH: 26
<212> TYPE: DNA
<213> ORGANISM: Homo sapiens

<400> SEQUENCE: 58
ttccagcatt cgccagtacg agcttg                                       26

<210> SEQ ID NO 59
<211> LENGTH: 30
<212> TYPE: DNA
<213> ORGANISM: Homo sapiens

<400> SEQUENCE: 59
gatcaacatg ggagactccc acgtggacac                                   30

-continued

```
<210> SEQ ID NO 60
<211> LENGTH: 30
<212> TYPE: DNA
<213> ORGANISM: Homo sapiens

<400> SEQUENCE: 60
agatacttct tcggccaccg cctcggacac                                        30

<210> SEQ ID NO 61
<211> LENGTH: 1465
<212> TYPE: PRT
<213> ORGANISM: Artificial Sequence
<220> FEATURE:
<223> OTHER INFORMATION: SYNTHESIZED

<400> SEQUENCE: 61

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320
```

```
Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735
```

-continued

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser

```
            1145                1150                1155

Val Lys Glu Leu Leu Gly Ile Thr Ile Met Glu Arg Ser Ser Phe
            1160                1165                1170

Glu Lys Asn Pro Ile Asp Phe Leu Glu Ala Lys Gly Tyr Lys Glu
            1175                1180                1185

Val Lys Lys Asp Leu Ile Ile Lys Leu Pro Lys Tyr Ser Leu Phe
            1190                1195                1200

Glu Leu Glu Asn Gly Arg Lys Arg Met Leu Ala Ser Ala Gly Glu
            1205                1210                1215

Leu Gln Lys Gly Asn Glu Leu Ala Leu Pro Ser Lys Tyr Val Asn
            1220                1225                1230

Phe Leu Tyr Leu Ala Ser His Tyr Glu Lys Leu Lys Gly Ser Pro
            1235                1240                1245

Glu Asp Asn Glu Gln Lys Gln Leu Phe Val Glu Gln His Lys His
            1250                1255                1260

Tyr Leu Asp Glu Ile Ile Glu Gln Ile Ser Glu Phe Ser Lys Arg
            1265                1270                1275

Val Ile Leu Ala Asp Ala Asn Leu Asp Lys Val Leu Ser Ala Tyr
            1280                1285                1290

Asn Lys His Arg Asp Lys Pro Ile Arg Glu Gln Ala Glu Asn Ile
            1295                1300                1305

Ile His Leu Phe Thr Leu Thr Asn Leu Gly Ala Pro Ala Ala Phe
            1310                1315                1320

Lys Tyr Phe Asp Thr Thr Ile Asp Arg Lys Arg Tyr Thr Ser Thr
            1325                1330                1335

Lys Glu Val Leu Asp Ala Thr Leu Ile His Gln Ser Ile Thr Gly
            1340                1345                1350

Leu Tyr Glu Thr Arg Ile Asp Leu Ser Gln Leu Gly Gly Asp Pro
            1355                1360                1365

Lys Lys Lys Arg Lys Val Leu Glu Gly Gly Gly Ser Met Gly
            1370                1375                1380

Lys Gly Asp Pro Lys Lys Pro Arg Gly Lys Met Ser Ser Tyr Ala
            1385                1390                1395

Phe Phe Val Gln Thr Cys Arg Glu Glu His Lys Lys Lys His Pro
            1400                1405                1410

Asp Ala Ser Val Asn Phe Ser Glu Phe Ser Lys Lys Cys Ser Glu
            1415                1420                1425

Arg Trp Lys Thr Met Ser Ala Lys Glu Lys Gly Lys Phe Glu Asp
            1430                1435                1440

Met Ala Lys Ala Asp Lys Ala Arg Tyr Glu Arg Glu Met Lys Thr
            1445                1450                1455

Tyr Ile Pro Pro Lys Gly Glu
            1460                1465

<210> SEQ ID NO 62
<211> LENGTH: 1481
<212> TYPE: PRT
<213> ORGANISM: Artificial Sequence
<220> FEATURE:
<223> OTHER INFORMATION: SYNTHESIZED

<400> SEQUENCE: 62

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
```

```
                    20                  25                  30
Lys Val Leu Gly Asn Thr Asp Arg His Ser Ile Lys Lys Asn Leu Ile
                35                  40                  45
Gly Ala Leu Leu Phe Asp Ser Gly Glu Thr Ala Glu Ala Thr Arg Leu
            50                  55                  60
Lys Arg Thr Ala Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
            130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
            195                 200                 205
Lys Ala Ile Leu Ser Ala Arg Leu Ser Lys Ser Arg Arg Leu Glu Asn
            210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
```

```
Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
        835                 840                 845

Asp Ser Ile Asp Asn Lys Val Leu Thr Arg Ser Asp Lys Asn Arg Gly
    850                 855                 860
```

```
Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
        900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
        930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
                980                 985                 990

Gly Thr Ala Leu Ile Lys Lys Tyr Pro Lys Leu Glu Ser Glu Phe Val
        995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
```

```
                1265                1270                1275

Val Ile Leu Ala Asp Ala Asn Leu Asp Lys Val Leu Ser Ala Tyr
            1280                1285                1290

Asn Lys His Arg Asp Lys Pro Ile Arg Glu Gln Ala Glu Asn Ile
        1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
1325                1330                1335

Lys Glu Val Leu Asp Ala Thr Leu Ile His Gln Ser Ile Thr Gly
1340                1345                1350

Leu Tyr Glu Thr Arg Ile Asp Leu Ser Gln Leu Gly Gly Asp Pro
    1355                1360                1365

Lys Lys Lys Arg Lys Val Leu Glu Gly Gly Gly Ser Met Pro
        1370                1375                1380

Lys Arg Lys Val Ser Ser Ala Glu Gly Ala Ala Lys Glu Glu Pro
            1385                1390                1395

Lys Arg Arg Ser Ala Arg Leu Ser Ala Lys Pro Pro Ala Lys Val
                1400                1405                1410

Glu Ala Lys Pro Lys Lys Ala Ala Ala Lys Asp Lys Ser Ser Asp
                    1415                1420                1425

Lys Lys Val Gln Thr Lys Gly Lys Arg Gly Ala Lys Gly Lys Gln
                        1430                1435                1440

Ala Glu Val Ala Asn Gln Glu Thr Lys Glu Asp Leu Pro Ala Glu
                            1445                1450                1455

Asn Gly Glu Thr Lys Thr Glu Glu Ser Pro Ala Ser Asp Glu Ala
                                1460                1465                1470

Gly Glu Lys Glu Ala Lys Ser Asp
                                    1475                1480

<210> SEQ ID NO 63
<211> LENGTH: 1471
<212> TYPE: PRT
<213> ORGANISM: Artificial Sequence
<220> FEATURE:
<223> OTHER INFORMATION: SYNTHESIZED

<400> SEQUENCE: 63

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
```

```
              130                 135                 140
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560
```

```
Val Lys Gln Leu Lys Glu Asp Tyr Phe Lys Ile Glu Cys Phe Asp
            565                 570                 575

Ser Val Glu Ile Ser Gly Val Glu Asp Arg Phe Asn Ala Ser Leu Gly
        580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
        770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
        820                 825                 830

Ser Asp Tyr Asp Val Asp His Ile Val Pro Gln Ser Phe Ile Lys Asp
        835                 840                 845

Asp Ser Ile Asp Asn Lys Val Leu Thr Arg Ser Asp Lys Asn Arg Gly
        850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
            930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975
```

```
Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995             1000                1005

Tyr Gly Asp Tyr Lys Val Tyr Asp Val Arg Lys Met Ile Ala Lys
        1010            1015            1020

Ser Glu Gln Glu Ile Gly Lys Ala Thr Ala Lys Tyr Phe Phe Tyr
    1025            1030            1035

Ser Asn Ile Met Asn Phe Phe Lys Thr Glu Ile Thr Leu Ala Asn
    1040            1045            1050

Gly Glu Ile Arg Lys Arg Pro Leu Ile Glu Thr Asn Gly Glu Thr
    1055            1060            1065

Gly Glu Ile Val Trp Asp Lys Gly Arg Asp Phe Ala Thr Val Arg
    1070            1075            1080

Lys Val Leu Ser Met Pro Gln Val Asn Ile Val Lys Lys Thr Glu
    1085            1090            1095

Val Gln Thr Gly Gly Phe Ser Lys Glu Ser Ile Leu Pro Lys Arg
    1100            1105            1110

Asn Ser Asp Lys Leu Ile Ala Arg Lys Lys Asp Trp Asp Pro Lys
    1115            1120            1125

Lys Tyr Gly Gly Phe Asp Ser Pro Thr Val Ala Tyr Ser Val Leu
    1130            1135            1140

Val Val Ala Lys Val Glu Lys Gly Lys Ser Lys Lys Leu Lys Ser
    1145            1150            1155

Val Lys Glu Leu Leu Gly Ile Thr Ile Met Glu Arg Ser Ser Phe
    1160            1165            1170

Glu Lys Asn Pro Ile Asp Phe Leu Glu Ala Lys Gly Tyr Lys Glu
    1175            1180            1185

Val Lys Lys Asp Leu Ile Ile Lys Leu Pro Lys Tyr Ser Leu Phe
    1190            1195            1200

Glu Leu Glu Asn Gly Arg Lys Arg Met Leu Ala Ser Ala Gly Glu
    1205            1210            1215

Leu Gln Lys Gly Asn Glu Leu Ala Leu Pro Ser Lys Tyr Val Asn
    1220            1225            1230

Phe Leu Tyr Leu Ala Ser His Tyr Glu Lys Leu Lys Gly Ser Pro
    1235            1240            1245

Glu Asp Asn Glu Gln Lys Gln Leu Phe Val Glu Gln His Lys His
    1250            1255            1260

Tyr Leu Asp Glu Ile Ile Glu Gln Ile Ser Glu Phe Ser Lys Arg
    1265            1270            1275

Val Ile Leu Ala Asp Ala Asn Leu Asp Lys Val Leu Ser Ala Tyr
    1280            1285            1290

Asn Lys His Arg Asp Lys Pro Ile Arg Glu Gln Ala Glu Asn Ile
    1295            1300            1305

Ile His Leu Phe Thr Leu Thr Asn Leu Gly Ala Pro Ala Ala Phe
    1310            1315            1320

Lys Tyr Phe Asp Thr Thr Ile Asp Arg Lys Arg Tyr Thr Ser Thr
    1325            1330            1335

Lys Glu Val Leu Asp Ala Thr Leu Ile His Gln Ser Ile Thr Gly
    1340            1345            1350

Leu Tyr Glu Thr Arg Ile Asp Leu Ser Gln Leu Gly Gly Asp Pro
    1355            1360            1365

Lys Lys Lys Arg Lys Val Leu Glu Gly Gly Gly Gly Ser Met Pro
```

```
                1370              1375              1380
Lys Arg  Lys Ala Glu Gly Asp  Ala Lys Gly Asp  Lys Ala Lys Val
         1385              1390              1395
Lys Asp  Glu Pro Gln Arg Arg  Ser Ala Arg Leu  Ser Ala Lys Pro
         1400              1405              1410
Ala Pro  Pro Lys Pro Glu Pro  Lys Pro Lys Lys  Ala Pro Ala Lys
         1415              1420              1425
Lys Gly  Glu Lys Val Pro Lys  Gly Lys Lys Gly  Lys Ala Asp Ala
         1430              1435              1440
Gly Lys  Glu Gly Asn Asn Pro  Ala Glu Asn Gly  Asp Ala Lys Thr
         1445              1450              1455
Asp Gln  Ala Gln Lys Ala Glu  Gly Ala Gly Asp  Ala Lys
         1460              1465              1470
```

<210> SEQ ID NO 64
<211> LENGTH: 1480
<212> TYPE: PRT
<213> ORGANISM: Artificial Sequence
<220> FEATURE:
<223> OTHER INFORMATION: SYNTHESIZED

<400> SEQUENCE: 64

```
Met Asp Lys Lys Tyr Ser Ile Gly Leu Asp Ile Gly Thr Asn Ser Val
1               5                   10                  15
Gly Trp Ala Val Ile Thr Asp Glu Tyr Lys Val Pro Ser Lys Lys Phe
            20                  25                  30
Lys Val Leu Gly Asn Thr Asp Arg His Ser Ile Lys Lys Asn Leu Ile
        35                  40                  45
Gly Ala Leu Leu Phe Asp Ser Gly Glu Thr Ala Glu Ala Thr Arg Leu
    50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
            100                 105                 110
His Glu Arg His Pro Ile Phe Gly Asn Ile Val Asp Glu Val Ala Tyr
        115                 120                 125
His Glu Lys Tyr Pro Thr Ile Tyr His Leu Arg Lys Lys Leu Val Asp
    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
```

-continued

```
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
                450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
                530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
                610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
                675                 680                 685
```

```
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Ile Val Asp Glu Leu Val Lys Val Met Gly
                740                 745                 750
His Lys Pro Glu Asn Ile Val Ile Glu Met Ala Arg Glu Asn Gln Thr
                755                 760                 765
Thr Gln Lys Gly Gln Lys Asn Ser Arg Glu Arg Met Lys Arg Ile Glu
770                 775                 780
Glu Gly Ile Lys Glu Leu Gly Ser Gln Ile Leu Lys Glu His Pro Val
785                 790                 795                 800
Glu Asn Thr Gln Leu Gln Asn Glu Lys Leu Tyr Leu Tyr Tyr Leu Gln
                805                 810                 815
Asn Gly Arg Asp Met Tyr Val Asp Gln Glu Leu Asp Ile Asn Arg Leu
                820                 825                 830
Ser Asp Tyr Asp Val Asp His Ile Val Pro Gln Ser Phe Ile Lys Asp
                835                 840                 845
Asp Ser Ile Asp Asn Lys Val Leu Thr Arg Ser Asp Lys Asn Arg Gly
850                 855                 860
Lys Ser Asp Asn Val Pro Ser Glu Glu Val Val Lys Lys Met Lys Asn
865                 870                 875                 880
Tyr Trp Arg Gln Leu Leu Asn Ala Lys Leu Ile Thr Gln Arg Lys Phe
                885                 890                 895
Asp Asn Leu Thr Lys Ala Glu Arg Gly Gly Leu Ser Glu Leu Asp Lys
                900                 905                 910
Ala Gly Phe Ile Lys Arg Gln Leu Val Glu Thr Arg Gln Ile Thr Lys
                915                 920                 925
His Val Ala Gln Ile Leu Asp Ser Arg Met Asn Thr Lys Tyr Asp Glu
                930                 935                 940
Asn Asp Lys Leu Ile Arg Glu Val Lys Val Ile Thr Leu Lys Ser Lys
945                 950                 955                 960
Leu Val Ser Asp Phe Arg Lys Asp Phe Gln Phe Tyr Lys Val Arg Glu
                965                 970                 975
Ile Asn Asn Tyr His His Ala His Asp Ala Tyr Leu Asn Ala Val Val
                980                 985                 990
Gly Thr Ala Leu Ile Lys Lys Tyr Pro Lys Leu Glu Ser Glu Phe Val
                995                 1000                1005
Tyr Gly Asp Tyr Lys Val Tyr Asp Val Arg Lys Met Ile Ala Lys
                1010                1015                1020
Ser Glu Gln Glu Ile Gly Lys Ala Thr Ala Lys Tyr Phe Phe Tyr
                1025                1030                1035
Ser Asn Ile Met Asn Phe Phe Lys Thr Glu Ile Thr Leu Ala Asn
                1040                1045                1050
Gly Glu Ile Arg Lys Arg Pro Leu Ile Glu Thr Asn Gly Glu Thr
                1055                1060                1065
Gly Glu Ile Val Trp Asp Lys Gly Arg Asp Phe Ala Thr Val Arg
                1070                1075                1080
Lys Val Leu Ser Met Pro Gln Val Asn Ile Val Lys Lys Thr Glu
                1085                1090                1095
```

-continued

```
Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp Pro
    1355                1360                1365

Lys Lys Lys Arg Lys Val Leu Glu Gly Gly Gly Gly Ser Met Pro
    1370                1375                1380

Lys Arg Lys Ser Pro Glu Asn Thr Glu Gly Lys Asp Gly Ser Lys
    1385                1390                1395

Val Thr Lys Gln Glu Pro Thr Arg Arg Ser Ala Arg Leu Ser Ala
    1400                1405                1410

Lys Pro Ala Pro Pro Lys Pro Glu Pro Lys Pro Arg Lys Thr Ser
    1415                1420                1425

Ala Lys Lys Glu Pro Gly Ala Lys Ile Ser Arg Gly Ala Lys Gly
    1430                1435                1440

Lys Lys Glu Glu Lys Gln Glu Ala Gly Lys Glu Gly Thr Ala Pro
    1445                1450                1455

Ser Glu Asn Gly Glu Thr Lys Ala Glu Glu Ala Gln Lys Thr Glu
    1460                1465                1470

Ser Val Asp Asn Glu Gly Glu
    1475                1480
```

```
<210> SEQ ID NO 65
<211> LENGTH: 1458
<212> TYPE: PRT
<213> ORGANISM: Artificial Sequence
<220> FEATURE:
<223> OTHER INFORMATION: SYNTHESIZED

<400> SEQUENCE: 65
```

| | | | | | | | | | | | | | | |
|---|---|---|---|---|---|---|---|---|---|---|---|---|---|---|
| Met | Asp | Lys | Lys | Tyr | Ser | Ile | Gly | Leu | Asp | Ile | Gly | Thr | Asn | Ser | Val |
| 1 | | | | 5 | | | | | 10 | | | | | 15 | |

Gly Trp Ala Val Ile Thr Asp Glu Tyr Lys Val Pro Ser Lys Lys Phe
        20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp

```
                370                 375                 380
Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
                740                 745                 750

His Lys Pro Glu Asn Ile Val Ile Glu Met Ala Arg Glu Asn Gln Thr
                755                 760                 765

Thr Gln Lys Gly Gln Lys Asn Ser Arg Glu Arg Met Lys Arg Ile Glu
                770                 775                 780

Glu Gly Ile Lys Glu Leu Gly Ser Gln Ile Leu Lys Glu His Pro Val
785                 790                 795                 800
```

-continued

Glu Asn Thr Gln Leu Gln Asn Glu Lys Leu Tyr Leu Tyr Tyr Leu Gln
            805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
            835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
            885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
            965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

```
Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp Pro
    1355                1360                1365

Lys Lys Lys Arg Lys Val Leu Glu Gly Gly Gly Gly Ser Met Pro
    1370                1375                1380

Lys Arg Lys Ser Pro Glu Asn Thr Glu Gly Lys Asp Gly Ser Lys
    1385                1390                1395

Val Thr Lys Gln Glu Pro Thr Arg Arg Ser Ala Arg Leu Ser Ala
    1400                1405                1410

Lys Pro Ala Pro Pro Lys Pro Glu Pro Lys Pro Arg Lys Thr Ser
    1415                1420                1425

Ala Lys Lys Glu Pro Gly Ala Lys Ile Ser Arg Gly Ala Lys Gly
    1430                1435                1440

Lys Lys Glu Glu Lys Gln Glu Ala Gly Lys Glu Gly Thr Glu Asn
    1445                1450                1455
```

<210> SEQ ID NO 66
<211> LENGTH: 1461
<212> TYPE: PRT
<213> ORGANISM: Artificial Sequence
<220> FEATURE:
<223> OTHER INFORMATION: SYNTHESIZED

<400> SEQUENCE: 66

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95
```

```
Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
```

-continued

```
                515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
                740                 745                 750

His Lys Pro Glu Asn Ile Val Ile Glu Met Ala Arg Glu Asn Gln Thr
                755                 760                 765

Thr Gln Lys Gly Gln Lys Asn Ser Arg Glu Arg Met Lys Arg Ile Glu
            770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Ile Lys Asp
                835                 840                 845

Asp Ser Ile Asp Asn Lys Val Leu Thr Arg Ser Asp Lys Asn Arg Gly
            850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
                915                 920                 925

His Val Ala Gln Ile Leu Asp Ser Arg Met Asn Thr Lys Tyr Asp Glu
            930                 935                 940
```

-continued

```
Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335
```

-continued

```
Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp Pro
    1355                1360                1365

Lys Lys Lys Arg Lys Val Leu Glu Gly Gly Gly Ser Ser Thr
    1370                1375                1380

Asp His Pro Lys Tyr Ser Asp Met Ile Val Ala Ala Ile Gln Ala
    1385                1390                1395

Glu Lys Asn Arg Ala Gly Ser Ser Arg Gln Ser Ile Gln Lys Tyr
    1400                1405                1410

Ile Lys Ser His Tyr Lys Val Gly Glu Asn Ala Asp Ser Gln Ile
    1415                1420                1425

Lys Leu Ser Ile Lys Arg Leu Val Thr Thr Gly Val Leu Lys Gln
    1430                1435                1440

Thr Lys Gly Val Gly Ala Ser Gly Ser Phe Arg Leu Ala Lys Ser
    1445                1450                1455

Asp Glu Pro
    1460
```

```
<210> SEQ ID NO 67
<211> LENGTH: 1745
<212> TYPE: PRT
<213> ORGANISM: Artificial Sequence
<220> FEATURE:
<223> OTHER INFORMATION: SYNTHESIZED

<400> SEQUENCE: 67
```

```
Leu Leu Asn Pro Thr Lys Arg Glu Arg Lys Glu Asn Tyr Ser Ile Asp
1               5                   10                  15

Asn Tyr Tyr Lys Asp Val Leu Asn Thr Gly Arg Ser Ser Thr Pro Ser
                20                  25                  30

His Pro Arg Met Pro Lys Pro His Val Phe His Ser His Gln Leu Gln
            35                  40                  45

Pro Pro Gln Leu Lys Val Leu Tyr Glu Lys Glu Arg Met Trp Thr Ala
        50                  55                  60

Lys Lys Thr Gly Tyr Val Pro Thr Met Asp Asp Val Lys Ala Ala Tyr
65                  70                  75                  80

Gly Asp Ile Ser Asp Glu Glu Lys Lys Gln Lys Leu Glu Leu Leu
                85                  90                  95

Lys Leu Ser Val Asn Asn Ser Gln Pro Leu Thr Glu Glu Glu Lys
            100                 105                 110

Met Lys Ala Asp Trp Glu Ser Glu Gly Phe Thr Asn Trp Asn Lys Leu
        115                 120                 125

Glu Phe Arg Lys Phe Ile Thr Val Ser Gly Lys Tyr Gly Arg Asn Ser
    130                 135                 140

Ile Gln Ala Ile Ala Arg Glu Leu Ala Pro Gly Lys Thr Leu Glu Glu
145                 150                 155                 160

Val Arg Ala Tyr Ala Lys Ala Phe Trp Ser Asn Ile Glu Arg Ile Glu
                165                 170                 175

Asp Tyr Glu Lys Tyr Leu Lys Ile Ile Glu Asn Glu Glu Lys Ile
            180                 185                 190

Lys Arg Val Lys Met Gln Gln Glu Ala Leu Arg Arg Lys Leu Ser Glu
        195                 200                 205

Tyr Lys Asn Pro Phe Phe Asp Leu Lys Leu Lys His Pro Pro Ser Ser
    210                 215                 220
```

Asn Asn Lys Arg Thr Tyr Ser Glu Glu Asp Arg Phe Ile Leu Leu
225                 230                 235                 240

Met Leu Phe Lys Tyr Gly Leu Asp Arg Asp Val Tyr Glu Leu Val
            245                 250                 255

Arg Asp Glu Ile Arg Asp Cys Pro Leu Phe Glu Leu Asp Phe Tyr Phe
        260                 265                 270

Arg Ser Arg Thr Pro Val Glu Leu Ala Arg Arg Gly Asn Thr Leu Leu
        275                 280                 285

Gln Cys Leu Glu Lys Glu Phe Asn Ala Gly Ile Val Leu Asp Asp Ala
290                 295                 300

Thr Lys Asp Arg Met Lys Lys Glu Asp Glu Asn Gly Lys Arg Ile Arg
305                 310                 315                 320

Glu Glu Phe Ala Asp Gln Thr Ala Asn Glu Lys Glu Asn Val Asp Gly
            325                 330                 335

Val Glu Ser Lys Lys Ala Lys Ile Glu Asp Thr Ser Asn Val Gly Thr
            340                 345                 350

Glu Gln Leu Val Ala Glu Lys Ile Pro Glu Asn Glu Thr Thr His Thr
            355                 360                 365

Gly Ser Gly Met Asp Lys Lys Tyr Ser Ile Gly Leu Asp Ile Gly Thr
370                 375                 380

Asn Ser Val Gly Trp Ala Val Ile Thr Asp Glu Tyr Lys Val Pro Ser
385                 390                 395                 400

Lys Lys Phe Lys Val Leu Gly Asn Thr Asp Arg His Ser Ile Lys Lys
            405                 410                 415

Asn Leu Ile Gly Ala Leu Leu Phe Asp Ser Gly Glu Thr Ala Glu Ala
            420                 425                 430

Thr Arg Leu Lys Arg Thr Ala Arg Arg Arg Tyr Thr Arg Arg Lys Asn
            435                 440                 445

Arg Ile Cys Tyr Leu Gln Glu Ile Phe Ser Asn Glu Met Ala Lys Val
450                 455                 460

Asp Asp Ser Phe Phe His Arg Leu Glu Glu Ser Phe Leu Val Glu Glu
465                 470                 475                 480

Asp Lys Lys His Glu Arg His Pro Ile Phe Gly Asn Ile Val Asp Glu
            485                 490                 495

Val Ala Tyr His Glu Lys Tyr Pro Thr Ile Tyr His Leu Arg Lys Lys
            500                 505                 510

Leu Val Asp Ser Thr Asp Lys Ala Asp Leu Arg Leu Ile Tyr Leu Ala
            515                 520                 525

Leu Ala His Met Ile Lys Phe Arg Gly His Phe Leu Ile Glu Gly Asp
530                 535                 540

Leu Asn Pro Asp Asn Ser Asp Val Asp Lys Leu Phe Ile Gln Leu Val
545                 550                 555                 560

Gln Thr Tyr Asn Gln Leu Phe Glu Glu Asn Pro Ile Asn Ala Ser Gly
            565                 570                 575

Val Asp Ala Lys Ala Ile Leu Ser Ala Arg Leu Ser Lys Ser Arg Arg
            580                 585                 590

Leu Glu Asn Leu Ile Ala Gln Leu Pro Gly Glu Lys Lys Asn Gly Leu
            595                 600                 605

Phe Gly Asn Leu Ile Ala Leu Ser Leu Gly Leu Thr Pro Asn Phe Lys
            610                 615                 620

Ser Asn Phe Asp Leu Ala Glu Asp Ala Lys Leu Gln Leu Ser Lys Asp
625                 630                 635                 640

Thr Tyr Asp Asp Asp Leu Asp Asn Leu Leu Ala Gln Ile Gly Asp Gln

-continued

```
                645                 650                 655
Tyr Ala Asp Leu Phe Leu Ala Ala Lys Asn Leu Ser Asp Ala Ile Leu
                660                 665                 670

Leu Ser Asp Ile Leu Arg Val Asn Thr Glu Ile Thr Lys Ala Pro Leu
        675                 680                 685

Ser Ala Ser Met Ile Lys Arg Tyr Asp Glu His His Gln Asp Leu Thr
    690                 695                 700

Leu Leu Lys Ala Leu Val Arg Gln Gln Leu Pro Glu Lys Tyr Lys Glu
705                 710                 715                 720

Ile Phe Phe Asp Gln Ser Lys Asn Gly Tyr Ala Gly Tyr Ile Asp Gly
                725                 730                 735

Gly Ala Ser Gln Glu Glu Phe Tyr Lys Phe Ile Lys Pro Ile Leu Glu
                740                 745                 750

Lys Met Asp Gly Thr Glu Glu Leu Leu Val Lys Leu Asn Arg Glu Asp
                755                 760                 765

Leu Leu Arg Lys Gln Arg Thr Phe Asp Asn Gly Ser Ile Pro His Gln
770                 775                 780

Ile His Leu Gly Glu Leu His Ala Ile Leu Arg Arg Gln Glu Asp Phe
785                 790                 795                 800

Tyr Pro Phe Leu Lys Asp Asn Arg Glu Lys Ile Glu Lys Ile Leu Thr
                805                 810                 815

Phe Arg Ile Pro Tyr Tyr Val Gly Pro Leu Ala Arg Gly Asn Ser Arg
                820                 825                 830

Phe Ala Trp Met Thr Arg Lys Ser Glu Glu Thr Ile Thr Pro Trp Asn
                835                 840                 845

Phe Glu Glu Val Val Asp Lys Gly Ala Ser Ala Gln Ser Phe Ile Glu
850                 855                 860

Arg Met Thr Asn Phe Asp Lys Asn Leu Pro Asn Glu Lys Val Leu Pro
865                 870                 875                 880

Lys His Ser Leu Leu Tyr Glu Tyr Phe Thr Val Tyr Asn Glu Leu Thr
                885                 890                 895

Lys Val Lys Tyr Val Thr Glu Gly Met Arg Lys Pro Ala Phe Leu Ser
                900                 905                 910

Gly Glu Gln Lys Lys Ala Ile Val Asp Leu Leu Phe Lys Thr Asn Arg
                915                 920                 925

Lys Val Thr Val Lys Gln Leu Lys Glu Asp Tyr Phe Lys Lys Ile Glu
                930                 935                 940

Cys Phe Asp Ser Val Glu Ile Ser Gly Val Glu Asp Arg Phe Asn Ala
945                 950                 955                 960

Ser Leu Gly Thr Tyr His Asp Leu Leu Lys Ile Ile Lys Asp Lys Asp
                965                 970                 975

Phe Leu Asp Asn Glu Glu Asn Glu Asp Ile Leu Glu Asp Ile Val Leu
                980                 985                 990

Thr Leu Thr Leu Phe Glu Asp Arg Glu Met Ile Glu Glu Arg Leu Lys
                995                1000                1005

Thr Tyr Ala His Leu Phe Asp Asp Lys Val Met Lys Gln Leu Lys
        1010                1015                1020

Arg Arg Arg Tyr Thr Gly Trp Gly Arg Leu Ser Arg Lys Leu Ile
        1025                1030                1035

Asn Gly Ile Arg Asp Lys Gln Ser Gly Lys Thr Ile Leu Asp Phe
        1040                1045                1050

Leu Lys Ser Asp Gly Phe Ala Asn Arg Asn Phe Met Gln Leu Ile
        1055                1060                1065
```

His Asp Asp Ser Leu Thr Phe Lys Glu Asp Ile Gln Lys Ala Gln
    1070                1075                1080

Val Ser Gly Gln Gly Asp Ser Leu His Glu His Ile Ala Asn Leu
    1085                1090                1095

Ala Gly Ser Pro Ala Ile Lys Lys Gly Ile Leu Gln Thr Val Lys
    1100                1105                1110

Ile Val Asp Glu Leu Val Lys Val Met Gly His Lys Pro Glu Asn
    1115                1120                1125

Ile Val Ile Glu Met Ala Arg Glu Asn Gln Thr Thr Gln Lys Gly
    1130                1135                1140

Gln Lys Asn Ser Arg Glu Arg Met Lys Arg Ile Glu Glu Gly Ile
    1145                1150                1155

Lys Glu Leu Gly Ser Gln Ile Leu Lys Glu His Pro Val Glu Asn
    1160                1165                1170

Thr Gln Leu Gln Asn Glu Lys Leu Tyr Leu Tyr Tyr Leu Gln Asn
    1175                1180                1185

Gly Arg Asp Met Tyr Val Asp Gln Glu Leu Asp Ile Asn Arg Leu
    1190                1195                1200

Ser Asp Tyr Asp Val Asp His Ile Val Pro Gln Ser Phe Ile Lys
    1205                1210                1215

Asp Asp Ser Ile Asp Asn Lys Val Leu Thr Arg Ser Asp Lys Asn
    1220                1225                1230

Arg Gly Lys Ser Asp Asn Val Pro Ser Glu Glu Val Val Lys Lys
    1235                1240                1245

Met Lys Asn Tyr Trp Arg Gln Leu Leu Asn Ala Lys Leu Ile Thr
    1250                1255                1260

Gln Arg Lys Phe Asp Asn Leu Thr Lys Ala Glu Arg Gly Gly Leu
    1265                1270                1275

Ser Glu Leu Asp Lys Ala Gly Phe Ile Lys Arg Gln Leu Val Glu
    1280                1285                1290

Thr Arg Gln Ile Thr Lys His Val Ala Gln Ile Leu Asp Ser Arg
    1295                1300                1305

Met Asn Thr Lys Tyr Asp Glu Asn Asp Lys Leu Ile Arg Glu Val
    1310                1315                1320

Lys Val Ile Thr Leu Lys Ser Lys Leu Val Ser Asp Phe Arg Lys
    1325                1330                1335

Asp Phe Gln Phe Tyr Lys Val Arg Glu Ile Asn Asn Tyr His His
    1340                1345                1350

Ala His Asp Ala Tyr Leu Asn Ala Val Val Gly Thr Ala Leu Ile
    1355                1360                1365

Lys Lys Tyr Pro Lys Leu Glu Ser Glu Phe Val Tyr Gly Asp Tyr
    1370                1375                1380

Lys Val Tyr Asp Val Arg Lys Met Ile Ala Lys Ser Glu Gln Glu
    1385                1390                1395

Ile Gly Lys Ala Thr Ala Lys Tyr Phe Phe Tyr Ser Asn Ile Met
    1400                1405                1410

Asn Phe Phe Lys Thr Glu Ile Thr Leu Ala Asn Gly Glu Ile Arg
    1415                1420                1425

Lys Arg Pro Leu Ile Glu Thr Asn Gly Glu Thr Gly Glu Ile Val
    1430                1435                1440

Trp Asp Lys Gly Arg Asp Phe Ala Thr Val Arg Lys Val Leu Ser
    1445                1450                1455

```
Met Pro Gln Val Asn Ile Val Lys Lys Thr Glu Val Gln Thr Gly
    1460                1465                1470

Gly Phe Ser Lys Glu Ser Ile Leu Pro Lys Arg Asn Ser Asp Lys
    1475                1480                1485

Leu Ile Ala Arg Lys Lys Asp Trp Asp Pro Lys Lys Tyr Gly Gly
    1490                1495                1500

Phe Asp Ser Pro Thr Val Ala Tyr Ser Val Leu Val Val Ala Lys
    1505                1510                1515

Val Glu Lys Gly Lys Ser Lys Lys Leu Lys Ser Val Lys Glu Leu
    1520                1525                1530

Leu Gly Ile Thr Ile Met Glu Arg Ser Ser Phe Glu Lys Asn Pro
    1535                1540                1545

Ile Asp Phe Leu Glu Ala Lys Gly Tyr Lys Glu Val Lys Lys Asp
    1550                1555                1560

Leu Ile Ile Lys Leu Pro Lys Tyr Ser Leu Phe Glu Leu Glu Asn
    1565                1570                1575

Gly Arg Lys Arg Met Leu Ala Ser Ala Gly Glu Leu Gln Lys Gly
    1580                1585                1590

Asn Glu Leu Ala Leu Pro Ser Lys Tyr Val Asn Phe Leu Tyr Leu
    1595                1600                1605

Ala Ser His Tyr Glu Lys Leu Lys Gly Ser Pro Glu Asp Asn Glu
    1610                1615                1620

Gln Lys Gln Leu Phe Val Glu Gln His Lys His Tyr Leu Asp Glu
    1625                1630                1635

Ile Ile Glu Gln Ile Ser Glu Phe Ser Lys Arg Val Ile Leu Ala
    1640                1645                1650

Asp Ala Asn Leu Asp Lys Val Leu Ser Ala Tyr Asn Lys His Arg
    1655                1660                1665

Asp Lys Pro Ile Arg Glu Gln Ala Glu Asn Ile Ile His Leu Phe
    1670                1675                1680

Thr Leu Thr Asn Leu Gly Ala Pro Ala Ala Phe Lys Tyr Phe Asp
    1685                1690                1695

Thr Thr Ile Asp Arg Lys Arg Tyr Thr Ser Thr Lys Glu Val Leu
    1700                1705                1710

Asp Ala Thr Leu Ile His Gln Ser Ile Thr Gly Leu Tyr Glu Thr
    1715                1720                1725

Arg Ile Asp Leu Ser Gln Leu Gly Gly Asp Pro Lys Lys Lys Arg
    1730                1735                1740

Lys Val
    1745

<210> SEQ ID NO 68
<211> LENGTH: 1650
<212> TYPE: PRT
<213> ORGANISM: Artificial Sequence
<220> FEATURE:
<223> OTHER INFORMATION: SYNTHESIZED

<400> SEQUENCE: 68

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45
```

```
Gly Ala Leu Leu Phe Asp Ser Gly Glu Thr Ala Glu Ala Thr Arg Leu
    50                  55                  60

Lys Arg Thr Ala Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                    85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
```

```
                    465                 470                 475                 480
Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
                740                 745                 750

His Lys Pro Glu Asn Ile Val Ile Glu Met Ala Arg Glu Asn Gln Thr
                755                 760                 765

Thr Gln Lys Gly Gln Lys Asn Ser Arg Glu Arg Met Lys Arg Ile Glu
                770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
                820                 825                 830

Ser Asp Tyr Asp Val Asp His Ile Val Pro Gln Ser Phe Ile Lys Asp
                835                 840                 845

Asp Ser Ile Asp Asn Lys Val Leu Thr Arg Ser Asp Lys Asn Arg Gly
                850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895
```

```
Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr Pro Lys Leu Glu Ser Glu Phe Val
        995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290
```

Asn Lys His Arg Asp Lys Pro Ile Arg Glu Gln Ala Glu Asn Ile
1295                1300                1305

Ile His Leu Phe Thr Leu Thr Asn Leu Gly Ala Pro Ala Ala Phe
1310                1315                1320

Lys Tyr Phe Asp Thr Thr Ile Asp Arg Lys Arg Tyr Thr Ser Thr
1325                1330                1335

Lys Glu Val Leu Asp Ala Thr Leu Ile His Gln Ser Ile Thr Gly
1340                1345                1350

Leu Tyr Glu Thr Arg Ile Asp Leu Ser Gln Leu Gly Gly Asp Pro
1355                1360                1365

Lys Lys Lys Arg Lys Val Leu Glu Gly Gly Gly Ser Asp Met
1370                1375                1380

Asp Ser Ile Gly Glu Ser Glu Val Arg Ala Leu Tyr Lys Ala Ile
1385                1390                1395

Leu Lys Phe Gly Asn Leu Lys Glu Ile Leu Asp Glu Leu Ile Ala
1400                1405                1410

Asp Gly Thr Leu Pro Val Lys Ser Phe Glu Lys Tyr Gly Glu Thr
1415                1420                1425

Tyr Asp Glu Met Met Glu Ala Ala Lys Asp Cys Val His Glu Glu
1430                1435                1440

Glu Lys Asn Arg Lys Glu Ile Leu Glu Lys Leu Glu Lys His Ala
1445                1450                1455

Thr Ala Tyr Arg Ala Lys Leu Lys Ser Gly Glu Ile Lys Ala Glu
1460                1465                1470

Asn Gln Pro Lys Asp Asn Pro Leu Thr Arg Leu Ser Leu Lys Lys
1475                1480                1485

Arg Glu Lys Lys Ala Val Leu Phe Asn Phe Lys Gly Val Lys Ser
1490                1495                1500

Leu Asn Ala Glu Ser Leu Leu Ser Arg Val Glu Asp Leu Lys Tyr
1505                1510                1515

Leu Lys Asn Leu Ile Asn Ser Asn Tyr Lys Asp Asp Pro Leu Lys
1520                1525                1530

Phe Ser Leu Gly Asn Asn Thr Pro Lys Pro Val Gln Asn Trp Ser
1535                1540                1545

Ser Asn Trp Thr Lys Glu Glu Asp Glu Lys Leu Leu Ile Gly Val
1550                1555                1560

Phe Lys Tyr Gly Tyr Gly Ser Trp Thr Gln Ile Arg Asp Asp Pro
1565                1570                1575

Phe Leu Gly Ile Thr Asp Lys Ile Phe Leu Asn Glu Val His Asn
1580                1585                1590

Pro Val Ala Lys Lys Ser Ala Ser Ser Ser Asp Thr Thr Pro Thr
1595                1600                1605

Pro Ser Lys Lys Gly Lys Gly Ile Thr Gly Ser Ser Lys Lys Val
1610                1615                1620

Pro Gly Ala Ile His Leu Gly Arg Arg Val Asp Tyr Leu Leu Ser
1625                1630                1635

Phe Leu Arg Gly Gly Leu Asn Thr Lys Ser Pro Ser
1640                1645                1650

<210> SEQ ID NO 69
<211> LENGTH: 1568
<212> TYPE: PRT
<213> ORGANISM: Artificial Sequence
<220> FEATURE:
<223> OTHER INFORMATION: SYNTHESIZED

<400> SEQUENCE: 69

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Pro Ala Lys Val
            20                  25                  30

Glu Ala Lys Pro Lys Lys Ala Ala Ala Lys Asp Lys Ser Ser Asp Lys
        35                  40                  45

Lys Val Gln Thr Lys Gly Lys Arg Gly Ala Lys Gly Lys Gln Ala Glu
    50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Asp Lys Lys Tyr Ser Ile Gly
            100                 105                 110

Leu Asp Ile Gly Thr Asn Ser Val Gly Trp Ala Val Ile Thr Asp Glu
            115                 120                 125

Tyr Lys Val Pro Ser Lys Lys Phe Lys Val Leu Gly Asn Thr Asp Arg
130                 135                 140

His Ser Ile Lys Lys Asn Leu Ile Gly Ala Leu Leu Phe Asp Ser Gly
145                 150                 155                 160

Glu Thr Ala Glu Ala Thr Arg Leu Lys Arg Thr Ala Arg Arg Arg Tyr
                165                 170                 175

Thr Arg Arg Lys Asn Arg Ile Cys Tyr Leu Gln Glu Ile Phe Ser Asn
            180                 185                 190

Glu Met Ala Lys Val Asp Asp Ser Phe Phe His Arg Leu Glu Glu Ser
        195                 200                 205

Phe Leu Val Glu Glu Asp Lys Lys His Glu Arg His Pro Ile Phe Gly
    210                 215                 220

Asn Ile Val Asp Glu Val Ala Tyr His Glu Lys Tyr Pro Thr Ile Tyr
225                 230                 235                 240

His Leu Arg Lys Lys Leu Val Asp Ser Thr Asp Lys Ala Asp Leu Arg
                245                 250                 255

Leu Ile Tyr Leu Ala Leu Ala His Met Ile Lys Phe Arg Gly His Phe
            260                 265                 270

Leu Ile Glu Gly Asp Leu Asn Pro Asp Asn Ser Asp Val Asp Lys Leu
        275                 280                 285

Phe Ile Gln Leu Val Gln Thr Tyr Asn Gln Leu Phe Glu Glu Asn Pro
    290                 295                 300

Ile Asn Ala Ser Gly Val Asp Ala Lys Ala Ile Leu Ser Ala Arg Leu
305                 310                 315                 320

Ser Lys Ser Arg Arg Leu Glu Asn Leu Ile Ala Gln Leu Pro Gly Glu
                325                 330                 335

Lys Lys Asn Gly Leu Phe Gly Asn Leu Ile Ala Leu Ser Leu Gly Leu
            340                 345                 350

Thr Pro Asn Phe Lys Ser Asn Phe Asp Leu Ala Glu Asp Ala Lys Leu
        355                 360                 365

Gln Leu Ser Lys Asp Thr Tyr Asp Asp Asp Leu Asp Asn Leu Leu Ala
    370                 375                 380

Gln Ile Gly Asp Gln Tyr Ala Asp Leu Phe Leu Ala Ala Lys Asn Leu
385                 390                 395                 400

Ser Asp Ala Ile Leu Leu Ser Asp Ile Leu Arg Val Asn Thr Glu Ile

```
                      405                 410                 415
Thr Lys Ala Pro Leu Ser Ala Ser Met Ile Lys Arg Tyr Asp Glu His
                420                 425                 430

His Gln Asp Leu Thr Leu Leu Lys Ala Leu Val Arg Gln Gln Leu Pro
                435                 440                 445

Glu Lys Tyr Lys Glu Ile Phe Phe Asp Gln Ser Lys Asn Gly Tyr Ala
                450                 455                 460

Gly Tyr Ile Asp Gly Gly Ala Ser Gln Glu Glu Phe Tyr Lys Phe Ile
465                 470                 475                 480

Lys Pro Ile Leu Glu Lys Met Asp Gly Thr Glu Glu Leu Leu Val Lys
                485                 490                 495

Leu Asn Arg Glu Asp Leu Leu Arg Lys Gln Arg Thr Phe Asp Asn Gly
                500                 505                 510

Ser Ile Pro His Gln Ile His Leu Gly Glu Leu His Ala Ile Leu Arg
                515                 520                 525

Arg Gln Glu Asp Phe Tyr Pro Phe Leu Lys Asp Asn Arg Glu Lys Ile
                530                 535                 540

Glu Lys Ile Leu Thr Phe Arg Ile Pro Tyr Tyr Val Gly Pro Leu Ala
545                 550                 555                 560

Arg Gly Asn Ser Arg Phe Ala Trp Met Thr Arg Lys Ser Glu Glu Thr
                565                 570                 575

Ile Thr Pro Trp Asn Phe Glu Glu Val Val Asp Lys Gly Ala Ser Ala
                580                 585                 590

Gln Ser Phe Ile Glu Arg Met Thr Asn Phe Asp Lys Asn Leu Pro Asn
                595                 600                 605

Glu Lys Val Leu Pro Lys His Ser Leu Leu Tyr Glu Tyr Phe Thr Val
                610                 615                 620

Tyr Asn Glu Leu Thr Lys Val Lys Tyr Val Thr Glu Gly Met Arg Lys
625                 630                 635                 640

Pro Ala Phe Leu Ser Gly Glu Gln Lys Lys Ala Ile Val Asp Leu Leu
                645                 650                 655

Phe Lys Thr Asn Arg Lys Val Thr Val Lys Gln Leu Lys Glu Asp Tyr
                660                 665                 670

Phe Lys Lys Ile Glu Cys Phe Asp Ser Val Glu Ile Ser Gly Val Glu
                675                 680                 685

Asp Arg Phe Asn Ala Ser Leu Gly Thr Tyr His Asp Leu Leu Lys Ile
                690                 695                 700

Ile Lys Asp Lys Asp Phe Leu Asp Asn Glu Glu Asn Glu Asp Ile Leu
705                 710                 715                 720

Glu Asp Ile Val Leu Thr Leu Thr Leu Phe Glu Asp Arg Glu Met Ile
                725                 730                 735

Glu Glu Arg Leu Lys Thr Tyr Ala His Leu Phe Asp Asp Lys Val Met
                740                 745                 750

Lys Gln Leu Lys Arg Arg Arg Tyr Thr Gly Trp Gly Arg Leu Ser Arg
                755                 760                 765

Lys Leu Ile Asn Gly Ile Arg Asp Lys Gln Ser Gly Lys Thr Ile Leu
                770                 775                 780

Asp Phe Leu Lys Ser Asp Gly Phe Ala Asn Arg Asn Phe Met Gln Leu
785                 790                 795                 800

Ile His Asp Asp Ser Leu Thr Phe Lys Glu Asp Ile Gln Lys Ala Gln
                805                 810                 815

Val Ser Gly Gln Gly Asp Ser Leu His Glu His Ile Ala Asn Leu Ala
                820                 825                 830
```

```
Gly Ser Pro Ala Ile Lys Lys Gly Ile Leu Gln Thr Val Lys Ile Val
        835                 840                 845

Asp Glu Leu Val Lys Val Met Gly His Lys Pro Glu Asn Ile Val Ile
    850                 855                 860

Glu Met Ala Arg Glu Asn Gln Thr Thr Gln Lys Gly Gln Lys Asn Ser
865                 870                 875                 880

Arg Glu Arg Met Lys Arg Ile Glu Glu Gly Ile Lys Glu Leu Gly Ser
                885                 890                 895

Gln Ile Leu Lys Glu His Pro Val Glu Asn Thr Gln Leu Gln Asn Glu
            900                 905                 910

Lys Leu Tyr Leu Tyr Tyr Leu Gln Asn Gly Arg Asp Met Tyr Val Asp
        915                 920                 925

Gln Glu Leu Asp Ile Asn Arg Leu Ser Asp Tyr Asp Val Asp His Ile
930                 935                 940

Val Pro Gln Ser Phe Ile Lys Asp Asp Ser Ile Asp Asn Lys Val Leu
945                 950                 955                 960

Thr Arg Ser Asp Lys Asn Arg Gly Lys Ser Asp Asn Val Pro Ser Glu
                965                 970                 975

Glu Val Val Lys Lys Met Lys Asn Tyr Trp Arg Gln Leu Leu Asn Ala
            980                 985                 990

Lys Leu Ile Thr Gln Arg Lys Phe Asp Asn Leu Thr Lys Ala Glu Arg
        995                 1000                1005

Gly Gly Leu Ser Glu Leu Asp Lys Ala Gly Phe Ile Lys Arg Gln
    1010                1015                1020

Leu Val Glu Thr Arg Gln Ile Thr Lys His Val Ala Gln Ile Leu
    1025                1030                1035

Asp Ser Arg Met Asn Thr Lys Tyr Asp Glu Asn Asp Lys Leu Ile
    1040                1045                1050

Arg Glu Val Lys Val Ile Thr Leu Lys Ser Lys Leu Val Ser Asp
    1055                1060                1065

Phe Arg Lys Asp Phe Gln Phe Tyr Lys Val Arg Glu Ile Asn Asn
    1070                1075                1080

Tyr His His Ala His Asp Ala Tyr Leu Asn Ala Val Val Gly Thr
    1085                1090                1095

Ala Leu Ile Lys Lys Tyr Pro Lys Leu Glu Ser Glu Phe Val Tyr
    1100                1105                1110

Gly Asp Tyr Lys Val Tyr Asp Val Arg Lys Met Ile Ala Lys Ser
    1115                1120                1125

Glu Gln Glu Ile Gly Lys Ala Thr Ala Lys Tyr Phe Phe Tyr Ser
    1130                1135                1140

Asn Ile Met Asn Phe Phe Lys Thr Glu Ile Thr Leu Ala Asn Gly
    1145                1150                1155

Glu Ile Arg Lys Arg Pro Leu Ile Glu Thr Asn Gly Glu Thr Gly
    1160                1165                1170

Glu Ile Val Trp Asp Lys Gly Arg Asp Phe Ala Thr Val Arg Lys
    1175                1180                1185

Val Leu Ser Met Pro Gln Val Asn Ile Val Lys Lys Thr Glu Val
    1190                1195                1200

Gln Thr Gly Gly Phe Ser Lys Glu Ser Ile Leu Pro Lys Arg Asn
    1205                1210                1215

Ser Asp Lys Leu Ile Ala Arg Lys Lys Asp Trp Asp Pro Lys Lys
    1220                1225                1230
```

```
Tyr Gly Gly Phe Asp Ser Pro Thr Val Ala Tyr Ser Val Leu Val
    1235                1240                1245

Val Ala Lys Val Glu Lys Gly Lys Ser Lys Lys Leu Lys Ser Val
1250                1255                1260

Lys Glu Leu Leu Gly Ile Thr Ile Met Glu Arg Ser Ser Phe Glu
1265                1270                1275

Lys Asn Pro Ile Asp Phe Leu Glu Ala Lys Gly Tyr Lys Glu Val
    1280                1285                1290

Lys Lys Asp Leu Ile Ile Lys Leu Pro Lys Tyr Ser Leu Phe Glu
1295                1300                1305

Leu Glu Asn Gly Arg Lys Arg Met Leu Ala Ser Ala Gly Glu Leu
    1310                1315                1320

Gln Lys Gly Asn Glu Leu Ala Leu Pro Ser Lys Tyr Val Asn Phe
1325                1330                1335

Leu Tyr Leu Ala Ser His Tyr Glu Lys Leu Lys Gly Ser Pro Glu
    1340                1345                1350

Asp Asn Glu Gln Lys Gln Leu Phe Val Glu Gln His Lys His Tyr
1355                1360                1365

Leu Asp Glu Ile Ile Glu Gln Ile Ser Glu Phe Ser Lys Arg Val
    1370                1375                1380

Ile Leu Ala Asp Ala Asn Leu Asp Lys Val Leu Ser Ala Tyr Asn
1385                1390                1395

Lys His Arg Asp Lys Pro Ile Arg Glu Gln Ala Glu Asn Ile Ile
    1400                1405                1410

His Leu Phe Thr Leu Thr Asn Leu Gly Ala Pro Ala Ala Phe Lys
1415                1420                1425

Tyr Phe Asp Thr Thr Ile Asp Arg Lys Arg Tyr Thr Ser Thr Lys
    1430                1435                1440

Glu Val Leu Asp Ala Thr Leu Ile His Gln Ser Ile Thr Gly Leu
1445                1450                1455

Tyr Glu Thr Arg Ile Asp Leu Ser Gln Leu Gly Gly Asp Pro Lys
    1460                1465                1470

Lys Lys Arg Lys Val Leu Glu Gly Gly Gly Ser Gly Lys Gly
1475                1480                1485

Asp Pro Lys Lys Pro Arg Gly Lys Met Ser Ser Tyr Ala Phe Phe
    1490                1495                1500

Val Gln Thr Cys Arg Glu Glu His Lys Lys Lys His Pro Asp Ala
1505                1510                1515

Ser Val Asn Phe Ser Glu Phe Ser Lys Lys Cys Ser Glu Arg Trp
    1520                1525                1530

Lys Thr Met Ser Ala Lys Glu Lys Gly Lys Phe Glu Asp Met Ala
1535                1540                1545

Lys Ala Asp Lys Ala Arg Tyr Glu Arg Glu Met Lys Thr Tyr Ile
    1550                1555                1560

Pro Pro Lys Gly Glu
    1565
```

<210> SEQ ID NO 70
<211> LENGTH: 1565
<212> TYPE: PRT
<213> ORGANISM: Artificial Sequence
<220> FEATURE:
<223> OTHER INFORMATION: SYNTHESIZED

<400> SEQUENCE: 70

-continued

```
Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Pro Ala Lys Val
            20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
            85                  90                  95

Ala Lys Ser Asp Thr Gly Ser Gly Met Asp Lys Lys Tyr Ser Ile Gly
            100                 105                 110

Leu Asp Ile Gly Thr Asn Ser Val Gly Trp Ala Val Ile Thr Asp Glu
            115                 120                 125

Tyr Lys Val Pro Ser Lys Lys Phe Lys Val Leu Gly Asn Thr Asp Arg
            130                 135                 140

His Ser Ile Lys Lys Asn Leu Ile Gly Ala Leu Leu Phe Asp Ser Gly
145                 150                 155                 160

Glu Thr Ala Glu Ala Thr Arg Leu Lys Arg Thr Ala Arg Arg Arg Tyr
            165                 170                 175

Thr Arg Arg Lys Asn Arg Ile Cys Tyr Leu Gln Glu Ile Phe Ser Asn
            180                 185                 190

Glu Met Ala Lys Val Asp Asp Ser Phe Phe His Arg Leu Glu Glu Ser
            195                 200                 205

Phe Leu Val Glu Glu Asp Lys Lys His Glu Arg His Pro Ile Phe Gly
210                 215                 220

Asn Ile Val Asp Glu Val Ala Tyr His Glu Lys Tyr Pro Thr Ile Tyr
225                 230                 235                 240

His Leu Arg Lys Lys Leu Val Asp Ser Thr Asp Lys Ala Asp Leu Arg
            245                 250                 255

Leu Ile Tyr Leu Ala Leu Ala His Met Ile Lys Phe Arg Gly His Phe
            260                 265                 270

Leu Ile Glu Gly Asp Leu Asn Pro Asp Asn Ser Asp Val Asp Lys Leu
            275                 280                 285

Phe Ile Gln Leu Val Gln Thr Tyr Asn Gln Leu Phe Glu Glu Asn Pro
290                 295                 300

Ile Asn Ala Ser Gly Val Asp Ala Lys Ala Ile Leu Ser Ala Arg Leu
305                 310                 315                 320

Ser Lys Ser Arg Arg Leu Glu Asn Leu Ile Ala Gln Leu Pro Gly Glu
            325                 330                 335

Lys Lys Asn Gly Leu Phe Gly Asn Leu Ile Ala Leu Ser Leu Gly Leu
            340                 345                 350

Thr Pro Asn Phe Lys Ser Asn Phe Asp Leu Ala Glu Asp Ala Lys Leu
            355                 360                 365

Gln Leu Ser Lys Asp Thr Tyr Asp Asp Asp Leu Asp Asn Leu Leu Ala
370                 375                 380

Gln Ile Gly Asp Gln Tyr Ala Asp Leu Phe Leu Ala Ala Lys Asn Leu
385                 390                 395                 400

Ser Asp Ala Ile Leu Leu Ser Asp Ile Leu Arg Val Asn Thr Glu Ile
            405                 410                 415

Thr Lys Ala Pro Leu Ser Ala Ser Met Ile Lys Arg Tyr Asp Glu His
```

```
                420              425              430
His Gln Asp Leu Thr Leu Leu Lys Ala Leu Val Arg Gln Gln Leu Pro
                435              440              445
Glu Lys Tyr Lys Glu Ile Phe Phe Asp Gln Ser Lys Asn Gly Tyr Ala
        450              455              460
Gly Tyr Ile Asp Gly Gly Ala Ser Gln Glu Glu Phe Tyr Lys Phe Ile
465              470              475              480
Lys Pro Ile Leu Glu Lys Met Asp Gly Thr Glu Glu Leu Leu Val Lys
                485              490              495
Leu Asn Arg Glu Asp Leu Leu Arg Lys Gln Arg Thr Phe Asp Asn Gly
                500              505              510
Ser Ile Pro His Gln Ile His Leu Gly Glu Leu His Ala Ile Leu Arg
        515              520              525
Arg Gln Glu Asp Phe Tyr Pro Phe Leu Lys Asp Asn Arg Glu Lys Ile
        530              535              540
Glu Lys Ile Leu Thr Phe Arg Ile Pro Tyr Tyr Val Gly Pro Leu Ala
545              550              555              560
Arg Gly Asn Ser Arg Phe Ala Trp Met Thr Arg Lys Ser Glu Glu Thr
                565              570              575
Ile Thr Pro Trp Asn Phe Glu Glu Val Val Asp Lys Gly Ala Ser Ala
                580              585              590
Gln Ser Phe Ile Glu Arg Met Thr Asn Phe Asp Lys Asn Leu Pro Asn
        595              600              605
Glu Lys Val Leu Pro Lys His Ser Leu Leu Tyr Glu Tyr Phe Thr Val
        610              615              620
Tyr Asn Glu Leu Thr Lys Val Lys Tyr Val Thr Glu Gly Met Arg Lys
625              630              635              640
Pro Ala Phe Leu Ser Gly Glu Gln Lys Lys Ala Ile Val Asp Leu Leu
                645              650              655
Phe Lys Thr Asn Arg Lys Val Thr Val Lys Gln Leu Lys Glu Asp Tyr
                660              665              670
Phe Lys Lys Ile Glu Cys Phe Asp Ser Val Glu Ile Ser Gly Val Glu
                675              680              685
Asp Arg Phe Asn Ala Ser Leu Gly Thr Tyr His Asp Leu Leu Lys Ile
        690              695              700
Ile Lys Asp Lys Asp Phe Leu Asp Asn Glu Glu Asn Glu Asp Ile Leu
705              710              715              720
Glu Asp Ile Val Leu Thr Leu Thr Leu Phe Glu Asp Arg Glu Met Ile
                725              730              735
Glu Glu Arg Leu Lys Thr Tyr Ala His Leu Phe Asp Asp Lys Val Met
                740              745              750
Lys Gln Leu Lys Arg Arg Arg Tyr Thr Gly Trp Gly Arg Leu Ser Arg
                755              760              765
Lys Leu Ile Asn Gly Ile Arg Asp Lys Gln Ser Gly Lys Thr Ile Leu
                770              775              780
Asp Phe Leu Lys Ser Asp Gly Phe Ala Asn Arg Asn Phe Met Gln Leu
785              790              795              800
Ile His Asp Asp Ser Leu Thr Phe Lys Glu Asp Ile Gln Lys Ala Gln
                805              810              815
Val Ser Gly Gln Gly Asp Ser Leu His Glu His Ile Ala Asn Leu Ala
        820              825              830
Gly Ser Pro Ala Ile Lys Lys Gly Ile Leu Gln Thr Val Lys Ile Val
        835              840              845
```

```
Asp Glu Leu Val Lys Val Met Gly His Lys Pro Glu Asn Ile Val Ile
850                 855                 860

Glu Met Ala Arg Glu Asn Gln Thr Thr Gln Lys Gly Gln Lys Asn Ser
865                 870                 875                 880

Arg Glu Arg Met Lys Arg Ile Glu Glu Gly Ile Lys Glu Leu Gly Ser
            885                 890                 895

Gln Ile Leu Lys Glu His Pro Val Glu Asn Thr Gln Leu Gln Asn Glu
            900                 905                 910

Lys Leu Tyr Leu Tyr Tyr Leu Gln Asn Gly Arg Asp Met Tyr Val Asp
            915                 920                 925

Gln Glu Leu Asp Ile Asn Arg Leu Ser Asp Tyr Asp Val Asp His Ile
930                 935                 940

Val Pro Gln Ser Phe Ile Lys Asp Asp Ser Ile Asp Asn Lys Val Leu
945                 950                 955                 960

Thr Arg Ser Asp Lys Asn Arg Gly Lys Ser Asp Asn Val Pro Ser Glu
                965                 970                 975

Glu Val Val Lys Lys Met Lys Asn Tyr Trp Arg Gln Leu Leu Asn Ala
            980                 985                 990

Lys Leu Ile Thr Gln Arg Lys Phe Asp Asn Leu Thr Lys Ala Glu Arg
            995                 1000                1005

Gly Gly Leu Ser Glu Leu Asp Lys Ala Gly Phe Ile Lys Arg Gln
1010                1015                1020

Leu Val Glu Thr Arg Gln Ile Thr Lys His Val Ala Gln Ile Leu
1025                1030                1035

Asp Ser Arg Met Asn Thr Lys Tyr Asp Glu Asn Asp Lys Leu Ile
1040                1045                1050

Arg Glu Val Lys Val Ile Thr Leu Lys Ser Lys Leu Val Ser Asp
1055                1060                1065

Phe Arg Lys Asp Phe Gln Phe Tyr Lys Val Arg Glu Ile Asn Asn
1070                1075                1080

Tyr His His Ala His Asp Ala Tyr Leu Asn Ala Val Val Gly Thr
1085                1090                1095

Ala Leu Ile Lys Lys Tyr Pro Lys Leu Glu Ser Glu Phe Val Tyr
1100                1105                1110

Gly Asp Tyr Lys Val Tyr Asp Val Arg Lys Met Ile Ala Lys Ser
1115                1120                1125

Glu Gln Glu Ile Gly Lys Ala Thr Ala Lys Tyr Phe Phe Tyr Ser
1130                1135                1140

Asn Ile Met Asn Phe Phe Lys Thr Glu Ile Thr Leu Ala Asn Gly
1145                1150                1155

Glu Ile Arg Lys Arg Pro Leu Ile Glu Thr Asn Gly Glu Thr Gly
1160                1165                1170

Glu Ile Val Trp Asp Lys Gly Arg Asp Phe Ala Thr Val Arg Lys
1175                1180                1185

Val Leu Ser Met Pro Gln Val Asn Ile Val Lys Lys Thr Glu Val
1190                1195                1200

Gln Thr Gly Gly Phe Ser Lys Glu Ser Ile Leu Pro Lys Arg Asn
1205                1210                1215

Ser Asp Lys Leu Ile Ala Arg Lys Lys Asp Trp Asp Pro Lys Lys
1220                1225                1230

Tyr Gly Gly Phe Asp Ser Pro Thr Val Ala Tyr Ser Val Leu Val
1235                1240                1245
```

```
Val Ala Lys Val Glu Lys Gly Lys Ser Lys Leu Lys Ser Val
    1250            1255                1260
Lys Glu Leu Leu Gly Ile Thr Ile Met Glu Arg Ser Ser Phe Glu
1265                1270                1275
Lys Asn Pro Ile Asp Phe Leu Glu Ala Lys Gly Tyr Lys Glu Val
    1280                1285                1290
Lys Lys Asp Leu Ile Ile Lys Leu Pro Lys Tyr Ser Leu Phe Glu
1295                1300                1305
Leu Glu Asn Gly Arg Lys Arg Met Leu Ala Ser Ala Gly Glu Leu
    1310                1315                1320
Gln Lys Gly Asn Glu Leu Ala Leu Pro Ser Lys Tyr Val Asn Phe
1325                1330                1335
Leu Tyr Leu Ala Ser His Tyr Glu Lys Leu Lys Gly Ser Pro Glu
    1340                1345                1350
Asp Asn Glu Gln Lys Gln Leu Phe Val Glu Gln His Lys His Tyr
1355                1360                1365
Leu Asp Glu Ile Ile Glu Gln Ile Ser Glu Phe Ser Lys Arg Val
    1370                1375                1380
Ile Leu Ala Asp Ala Asn Leu Asp Lys Val Leu Ser Ala Tyr Asn
1385                1390                1395
Lys His Arg Asp Lys Pro Ile Arg Glu Gln Ala Glu Asn Ile Ile
    1400                1405                1410
His Leu Phe Thr Leu Thr Asn Leu Gly Ala Pro Ala Ala Phe Lys
1415                1420                1425
Tyr Phe Asp Thr Thr Ile Asp Arg Lys Arg Tyr Thr Ser Thr Lys
    1430                1435                1440
Glu Val Leu Asp Ala Thr Leu Ile His Gln Ser Ile Thr Gly Leu
1445                1450                1455
Tyr Glu Thr Arg Ile Asp Leu Ser Gln Leu Gly Gly Asp Pro Lys
    1460                1465                1470
Lys Lys Arg Lys Val Leu Glu Gly Gly Gly Gly Ser Ser Thr Asp
1475                1480                1485
His Pro Lys Tyr Ser Asp Met Ile Val Ala Ala Ile Gln Ala Glu
    1490                1495                1500
Lys Asn Arg Ala Gly Ser Ser Arg Gln Ser Ile Gln Lys Tyr Ile
1505                1510                1515
Lys Ser His Tyr Lys Val Gly Glu Asn Ala Asp Ser Gln Ile Lys
    1520                1525                1530
Leu Ser Ile Lys Arg Leu Val Thr Thr Gly Val Leu Lys Gln Thr
1535                1540                1545
Lys Gly Val Gly Ala Ser Gly Ser Phe Arg Leu Ala Lys Ser Asp
    1550                1555                1560
Glu Pro
1565

<210> SEQ ID NO 71
<211> LENGTH: 1754
<212> TYPE: PRT
<213> ORGANISM: Artificial Sequence
<220> FEATURE:
<223> OTHER INFORMATION: SYNTHESIZED

<400> SEQUENCE: 71

Met Pro Lys Arg Lys Val Ser Ser Ala Glu Gly Ala Ala Lys Glu Glu
1               5                   10                  15
```

Pro Lys Arg Arg Ser Ala Arg Leu Ser Ala Lys Pro Ala Lys Val
            20                  25                  30

Glu Ala Lys Pro Lys Lys Ala Ala Ala Lys Asp Lys Ser Ser Asp Lys
        35                  40                  45

Lys Val Gln Thr Lys Gly Lys Arg Gly Ala Lys Gly Lys Gln Ala Glu
50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Asp Lys Lys Tyr Ser Ile Gly
            100                 105                 110

Leu Asp Ile Gly Thr Asn Ser Val Gly Trp Ala Val Ile Thr Asp Glu
            115                 120                 125

Tyr Lys Val Pro Ser Lys Lys Phe Lys Val Leu Gly Asn Thr Asp Arg
        130                 135                 140

His Ser Ile Lys Lys Asn Leu Ile Gly Ala Leu Leu Phe Asp Ser Gly
145                 150                 155                 160

Glu Thr Ala Glu Ala Thr Arg Leu Lys Arg Thr Ala Arg Arg Arg Tyr
                165                 170                 175

Thr Arg Arg Lys Asn Arg Ile Cys Tyr Leu Gln Glu Ile Phe Ser Asn
            180                 185                 190

Glu Met Ala Lys Val Asp Asp Ser Phe Phe His Arg Leu Glu Glu Ser
        195                 200                 205

Phe Leu Val Glu Glu Asp Lys Lys His Glu Arg His Pro Ile Phe Gly
210                 215                 220

Asn Ile Val Asp Glu Val Ala Tyr His Glu Lys Tyr Pro Thr Ile Tyr
225                 230                 235                 240

His Leu Arg Lys Lys Leu Val Asp Ser Thr Asp Lys Ala Asp Leu Arg
                245                 250                 255

Leu Ile Tyr Leu Ala Leu Ala His Met Ile Lys Phe Arg Gly His Phe
            260                 265                 270

Leu Ile Glu Gly Asp Leu Asn Pro Asp Asn Ser Asp Val Asp Lys Leu
        275                 280                 285

Phe Ile Gln Leu Val Gln Thr Tyr Asn Gln Leu Phe Glu Glu Asn Pro
290                 295                 300

Ile Asn Ala Ser Gly Val Asp Ala Lys Ala Ile Leu Ser Ala Arg Leu
305                 310                 315                 320

Ser Lys Ser Arg Arg Leu Glu Asn Leu Ile Ala Gln Leu Pro Gly Glu
                325                 330                 335

Lys Lys Asn Gly Leu Phe Gly Asn Leu Ile Ala Leu Ser Leu Gly Leu
            340                 345                 350

Thr Pro Asn Phe Lys Ser Asn Phe Asp Leu Ala Glu Asp Ala Lys Leu
        355                 360                 365

Gln Leu Ser Lys Asp Thr Tyr Asp Asp Asp Leu Asp Asn Leu Leu Ala
370                 375                 380

Gln Ile Gly Asp Gln Tyr Ala Asp Leu Phe Leu Ala Ala Lys Asn Leu
385                 390                 395                 400

Ser Asp Ala Ile Leu Leu Ser Asp Ile Leu Arg Val Asn Thr Glu Ile
                405                 410                 415

Thr Lys Ala Pro Leu Ser Ala Ser Met Ile Lys Arg Tyr Asp Glu His
            420                 425                 430

His Gln Asp Leu Thr Leu Leu Lys Ala Leu Val Arg Gln Gln Leu Pro

```
                435                 440                 445
Glu Lys Tyr Lys Glu Ile Phe Phe Asp Gln Ser Lys Asn Gly Tyr Ala
450                 455                 460

Gly Tyr Ile Asp Gly Gly Ala Ser Gln Glu Glu Phe Tyr Lys Phe Ile
465                 470                 475                 480

Lys Pro Ile Leu Glu Lys Met Asp Gly Thr Glu Glu Leu Leu Val Lys
                485                 490                 495

Leu Asn Arg Glu Asp Leu Leu Arg Lys Gln Arg Thr Phe Asp Asn Gly
            500                 505                 510

Ser Ile Pro His Gln Ile His Leu Gly Glu Leu His Ala Ile Leu Arg
        515                 520                 525

Arg Gln Glu Asp Phe Tyr Pro Phe Leu Lys Asp Asn Arg Glu Lys Ile
    530                 535                 540

Glu Lys Ile Leu Thr Phe Arg Ile Pro Tyr Tyr Val Gly Pro Leu Ala
545                 550                 555                 560

Arg Gly Asn Ser Arg Phe Ala Trp Met Thr Arg Lys Ser Glu Glu Thr
                565                 570                 575

Ile Thr Pro Trp Asn Phe Glu Glu Val Val Asp Lys Gly Ala Ser Ala
            580                 585                 590

Gln Ser Phe Ile Glu Arg Met Thr Asn Phe Asp Lys Asn Leu Pro Asn
        595                 600                 605

Glu Lys Val Leu Pro Lys His Ser Leu Leu Tyr Glu Tyr Phe Thr Val
    610                 615                 620

Tyr Asn Glu Leu Thr Lys Val Lys Tyr Val Thr Glu Gly Met Arg Lys
625                 630                 635                 640

Pro Ala Phe Leu Ser Gly Glu Gln Lys Lys Ala Ile Val Asp Leu Leu
                645                 650                 655

Phe Lys Thr Asn Arg Lys Val Thr Val Lys Gln Leu Lys Glu Asp Tyr
            660                 665                 670

Phe Lys Lys Ile Glu Cys Phe Asp Ser Val Glu Ile Ser Gly Val Glu
        675                 680                 685

Asp Arg Phe Asn Ala Ser Leu Gly Thr Tyr His Asp Leu Leu Lys Ile
    690                 695                 700

Ile Lys Asp Lys Asp Phe Leu Asp Asn Glu Glu Asn Glu Asp Ile Leu
705                 710                 715                 720

Glu Asp Ile Val Leu Thr Leu Thr Leu Phe Glu Asp Arg Glu Met Ile
                725                 730                 735

Glu Glu Arg Leu Lys Thr Tyr Ala His Leu Phe Asp Asp Lys Val Met
            740                 745                 750

Lys Gln Leu Lys Arg Arg Arg Tyr Thr Gly Trp Gly Arg Leu Ser Arg
        755                 760                 765

Lys Leu Ile Asn Gly Ile Arg Asp Lys Gln Ser Gly Lys Thr Ile Leu
    770                 775                 780

Asp Phe Leu Lys Ser Asp Gly Phe Ala Asn Arg Asn Phe Met Gln Leu
785                 790                 795                 800

Ile His Asp Asp Ser Leu Thr Phe Lys Glu Asp Ile Gln Lys Ala Gln
                805                 810                 815

Val Ser Gly Gln Gly Asp Ser Leu His Glu His Ile Ala Asn Leu Ala
            820                 825                 830

Gly Ser Pro Ala Ile Lys Lys Gly Ile Leu Gln Thr Val Lys Ile Val
        835                 840                 845

Asp Glu Leu Val Lys Val Met Gly His Lys Pro Glu Asn Ile Val Ile
    850                 855                 860
```

```
Glu Met Ala Arg Glu Asn Gln Thr Thr Gln Lys Gly Gln Lys Asn Ser
865                 870                 875                 880

Arg Glu Arg Met Lys Arg Ile Glu Glu Gly Ile Lys Glu Leu Gly Ser
                885                 890                 895

Gln Ile Leu Lys Glu His Pro Val Glu Asn Thr Gln Leu Gln Asn Glu
            900                 905                 910

Lys Leu Tyr Leu Tyr Tyr Leu Gln Asn Gly Arg Asp Met Tyr Val Asp
        915                 920                 925

Gln Glu Leu Asp Ile Asn Arg Leu Ser Asp Tyr Asp Val Asp His Ile
930                 935                 940

Val Pro Gln Ser Phe Ile Lys Asp Asp Ser Ile Asp Asn Lys Val Leu
945                 950                 955                 960

Thr Arg Ser Asp Lys Asn Arg Gly Lys Ser Asp Asn Val Pro Ser Glu
                965                 970                 975

Glu Val Val Lys Lys Met Lys Asn Tyr Trp Arg Gln Leu Leu Asn Ala
            980                 985                 990

Lys Leu Ile Thr Gln Arg Lys Phe Asp Asn Leu Thr Lys Ala Glu Arg
        995                 1000                1005

Gly Gly Leu Ser Glu Leu Asp Lys Ala Gly Phe Ile Lys Arg Gln
    1010                1015                1020

Leu Val Glu Thr Arg Gln Ile Thr Lys His Val Ala Gln Ile Leu
    1025                1030                1035

Asp Ser Arg Met Asn Thr Lys Tyr Asp Glu Asn Asp Lys Leu Ile
    1040                1045                1050

Arg Glu Val Lys Val Ile Thr Leu Lys Ser Lys Leu Val Ser Asp
    1055                1060                1065

Phe Arg Lys Asp Phe Gln Phe Tyr Lys Val Arg Glu Ile Asn Asn
    1070                1075                1080

Tyr His His Ala His Asp Ala Tyr Leu Asn Ala Val Val Gly Thr
    1085                1090                1095

Ala Leu Ile Lys Lys Tyr Pro Lys Leu Glu Ser Glu Phe Val Tyr
    1100                1105                1110

Gly Asp Tyr Lys Val Tyr Asp Val Arg Lys Met Ile Ala Lys Ser
    1115                1120                1125

Glu Gln Glu Ile Gly Lys Ala Thr Ala Lys Tyr Phe Phe Tyr Ser
    1130                1135                1140

Asn Ile Met Asn Phe Phe Lys Thr Glu Ile Thr Leu Ala Asn Gly
    1145                1150                1155

Glu Ile Arg Lys Arg Pro Leu Ile Glu Thr Asn Gly Glu Thr Gly
    1160                1165                1170

Glu Ile Val Trp Asp Lys Gly Arg Asp Phe Ala Thr Val Arg Lys
    1175                1180                1185

Val Leu Ser Met Pro Gln Val Asn Ile Val Lys Lys Thr Glu Val
    1190                1195                1200

Gln Thr Gly Gly Phe Ser Lys Glu Ser Ile Leu Pro Lys Arg Asn
    1205                1210                1215

Ser Asp Lys Leu Ile Ala Arg Lys Lys Asp Trp Asp Pro Lys Lys
    1220                1225                1230

Tyr Gly Gly Phe Asp Ser Pro Thr Val Ala Tyr Ser Val Leu Val
    1235                1240                1245

Val Ala Lys Val Glu Lys Gly Lys Ser Lys Lys Leu Lys Ser Val
    1250                1255                1260
```

-continued

```
Lys Glu Leu Leu Gly Ile Thr Ile Met Glu Arg Ser Ser Phe Glu
    1265                1270                1275

Lys Asn Pro Ile Asp Phe Leu Glu Ala Lys Gly Tyr Lys Glu Val
    1280                1285                1290

Lys Lys Asp Leu Ile Ile Lys Leu Pro Lys Tyr Ser Leu Phe Glu
    1295                1300                1305

Leu Glu Asn Gly Arg Lys Arg Met Leu Ala Ser Ala Gly Glu Leu
    1310                1315                1320

Gln Lys Gly Asn Glu Leu Ala Leu Pro Ser Lys Tyr Val Asn Phe
    1325                1330                1335

Leu Tyr Leu Ala Ser His Tyr Glu Lys Leu Lys Gly Ser Pro Glu
    1340                1345                1350

Asp Asn Glu Gln Lys Gln Leu Phe Val Glu Gln His Lys His Tyr
    1355                1360                1365

Leu Asp Glu Ile Ile Glu Gln Ile Ser Glu Phe Ser Lys Arg Val
    1370                1375                1380

Ile Leu Ala Asp Ala Asn Leu Asp Lys Val Leu Ser Ala Tyr Asn
    1385                1390                1395

Lys His Arg Asp Lys Pro Ile Arg Glu Gln Ala Glu Asn Ile Ile
    1400                1405                1410

His Leu Phe Thr Leu Thr Asn Leu Gly Ala Pro Ala Ala Phe Lys
    1415                1420                1425

Tyr Phe Asp Thr Thr Ile Asp Arg Lys Arg Tyr Thr Ser Thr Lys
    1430                1435                1440

Glu Val Leu Asp Ala Thr Leu Ile His Gln Ser Ile Thr Gly Leu
    1445                1450                1455

Tyr Glu Thr Arg Ile Asp Leu Ser Gln Leu Gly Gly Asp Pro Lys
    1460                1465                1470

Lys Lys Arg Lys Val Leu Glu Gly Gly Gly Ser Asp Met Asp
    1475                1480                1485

Ser Ile Gly Glu Ser Glu Val Arg Ala Leu Tyr Lys Ala Ile Leu
    1490                1495                1500

Lys Phe Gly Asn Leu Lys Glu Ile Leu Asp Glu Leu Ile Ala Asp
    1505                1510                1515

Gly Thr Leu Pro Val Lys Ser Phe Glu Lys Tyr Gly Glu Thr Tyr
    1520                1525                1530

Asp Glu Met Met Glu Ala Ala Lys Asp Cys Val His Glu Glu Glu
    1535                1540                1545

Lys Asn Arg Lys Glu Ile Leu Glu Lys Leu Glu Lys His Ala Thr
    1550                1555                1560

Ala Tyr Arg Ala Lys Leu Lys Ser Gly Glu Ile Lys Ala Glu Asn
    1565                1570                1575

Gln Pro Lys Asp Asn Pro Leu Thr Arg Leu Ser Leu Lys Lys Arg
    1580                1585                1590

Glu Lys Lys Ala Val Leu Phe Asn Phe Lys Gly Val Lys Ser Leu
    1595                1600                1605

Asn Ala Glu Ser Leu Leu Ser Arg Val Glu Asp Leu Lys Tyr Leu
    1610                1615                1620

Lys Asn Leu Ile Asn Ser Asn Tyr Lys Asp Asp Pro Leu Lys Phe
    1625                1630                1635

Ser Leu Gly Asn Asn Thr Pro Lys Pro Val Gln Asn Trp Ser Ser
    1640                1645                1650

Asn Trp Thr Lys Glu Glu Asp Glu Lys Leu Leu Ile Gly Val Phe
```

```
               1655                1660                1665

Lys Tyr Gly Tyr Gly Ser Trp Thr Gln Ile Arg Asp Asp Pro Phe
        1670                1675                1680

Leu Gly Ile Thr Asp Lys Ile Phe Leu Asn Glu Val His Asn Pro
1685                1690                1695

Val Ala Lys Lys Ser Ala Ser Ser Ser Asp Thr Thr Pro Thr Pro
        1700                1705                1710

Ser Lys Lys Gly Lys Gly Ile Thr Gly Ser Ser Lys Lys Val Pro
        1715                1720                1725

Gly Ala Ile His Leu Gly Arg Arg Val Asp Tyr Leu Leu Ser Phe
        1730                1735                1740

Leu Arg Gly Gly Leu Asn Thr Lys Ser Pro Ser
        1745                1750

<210> SEQ ID NO 72
<211> LENGTH: 1331
<212> TYPE: PRT
<213> ORGANISM: Artificial Sequence
<220> FEATURE:
<223> OTHER INFORMATION: SYNTHESIZED

<400> SEQUENCE: 72

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Pro Lys Val
                20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
        50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Thr Asn Gly Lys Ile Leu Gly
            100                 105                 110

Leu Asp Ile Gly Ile Ala Ser Val Gly Val Gly Ile Ile Glu Ala Lys
        115                 120                 125

Thr Gly Lys Val Val His Ala Asn Ser Arg Leu Phe Ser Ala Ala Asn
    130                 135                 140

Ala Glu Asn Asn Ala Glu Arg Arg Gly Phe Arg Gly Ser Arg Arg Leu
145                 150                 155                 160

Asn Arg Arg Lys Lys His Arg Val Lys Arg Val Arg Asp Leu Phe Glu
                165                 170                 175

Lys Tyr Gly Ile Val Thr Asp Phe Arg Asn Leu Asn Leu Asn Pro Tyr
            180                 185                 190

Glu Leu Arg Val Lys Gly Leu Thr Glu Gln Leu Lys Asn Glu Glu Leu
        195                 200                 205

Phe Ala Ala Leu Arg Thr Ile Ser Lys Arg Arg Gly Ile Ser Tyr Leu
    210                 215                 220

Asp Asp Ala Glu Asp Ser Thr Gly Ser Thr Asp Tyr Ala Lys Ser
225                 230                 235                 240

Ile Asp Glu Asn Arg Arg Leu Leu Lys Asn Lys Thr Pro Gly Gln Ile
                245                 250                 255

Gln Leu Glu Arg Leu Glu Lys Tyr Gly Gln Leu Arg Gly Asn Phe Thr
```

```
              260                 265                 270
Val Tyr Asp Glu Asn Gly Glu Ala His Arg Leu Ile Asn Val Phe Ser
            275                 280                 285
Thr Ser Asp Tyr Glu Lys Glu Ala Arg Lys Ile Leu Glu Thr Gln Ala
            290                 295                 300
Asp Tyr Asn Lys Lys Ile Thr Ala Glu Phe Ile Asp Asp Tyr Val Glu
305                 310                 315                 320
Ile Leu Thr Gln Lys Arg Lys Tyr Tyr His Gly Pro Gly Asn Glu Lys
                325                 330                 335
Ser Arg Thr Asp Tyr Gly Arg Phe Arg Thr Asp Gly Thr Thr Leu Glu
                340                 345                 350
Asn Ile Phe Gly Ile Leu Ile Gly Lys Cys Asn Phe Tyr Pro Asp Glu
                355                 360                 365
Tyr Arg Ala Ser Lys Ala Ser Tyr Thr Ala Gln Glu Tyr Asn Phe Leu
            370                 375                 380
Asn Asp Leu Asn Asn Leu Lys Val Ser Thr Glu Thr Gly Lys Leu Ser
385                 390                 395                 400
Thr Glu Gln Lys Glu Ser Leu Val Glu Phe Ala Lys Asn Thr Ala Thr
                        405                 410                 415
Leu Gly Pro Ala Lys Leu Leu Lys Glu Ile Ala Lys Ile Leu Asp Cys
                420                 425                 430
Lys Val Asp Glu Ile Lys Gly Tyr Arg Glu Asp Asp Lys Gly Lys Pro
            435                 440                 445
Asp Leu His Thr Phe Glu Pro Tyr Arg Lys Leu Lys Phe Asn Leu Glu
            450                 455                 460
Ser Ile Asn Ile Asp Asp Leu Ser Arg Glu Val Ile Asp Lys Leu Ala
465                 470                 475                 480
Asp Ile Leu Thr Leu Asn Thr Glu Arg Glu Gly Ile Glu Asp Ala Ile
                        485                 490                 495
Lys Arg Asn Leu Pro Asn Gln Phe Thr Glu Glu Gln Ile Ser Glu Ile
                500                 505                 510
Ile Lys Val Arg Lys Ser Gln Ser Thr Ala Phe Asn Lys Gly Trp His
            515                 520                 525
Ser Phe Ser Ala Lys Leu Met Asn Glu Leu Ile Pro Glu Leu Tyr Ala
            530                 535                 540
Thr Ser Asp Glu Gln Met Thr Ile Leu Thr Arg Leu Glu Lys Phe Lys
545                 550                 555                 560
Val Asn Lys Lys Ser Ser Lys Asn Thr Lys Thr Ile Asp Glu Lys Glu
                565                 570                 575
Val Thr Asp Glu Ile Tyr Asn Pro Val Val Ala Lys Ser Val Arg Gln
                580                 585                 590
Thr Ile Lys Ile Ile Asn Ala Val Lys Lys Tyr Gly Asp Phe Asp
            595                 600                 605
Lys Ile Val Ile Glu Met Pro Arg Asp Lys Asn Ala Asp Asp Glu Lys
            610                 615                 620
Lys Phe Ile Asp Lys Arg Asn Lys Glu Asn Lys Glu Lys Asp Asp
625                 630                 635                 640
Ala Leu Lys Arg Ala Ala Tyr Leu Tyr Asn Ser Ser Asp Lys Leu Pro
                        645                 650                 655
Asp Glu Val Phe His Gly Asn Lys Gln Leu Glu Thr Lys Ile Arg Leu
                660                 665                 670
Trp Tyr Gln Gln Gly Glu Arg Cys Leu Tyr Ser Gly Lys Pro Ile Ser
            675                 680                 685
```

```
Ile Gln Glu Leu Val His Asn Ser Asn Asn Phe Glu Ile Asp His Ile
    690                 695                 700

Leu Pro Leu Ser Leu Ser Phe Asp Asp Ser Leu Ala Asn Lys Val Leu
705                 710                 715                 720

Val Tyr Ala Trp Thr Asn Gln Glu Lys Gly Gln Lys Thr Pro Tyr Gln
                725                 730                 735

Val Ile Asp Ser Met Asp Ala Ala Trp Ser Phe Arg Glu Met Lys Asp
            740                 745                 750

Tyr Val Leu Lys Gln Lys Gly Leu Gly Lys Lys Arg Asp Tyr Leu
        755                 760                 765

Leu Thr Thr Glu Asn Ile Asp Lys Ile Glu Val Lys Lys Phe Ile
770                 775                 780

Glu Arg Asn Leu Val Asp Thr Arg Tyr Ala Ser Arg Val Val Leu Asn
785                 790                 795                 800

Ser Leu Gln Ser Ala Leu Arg Glu Leu Gly Lys Asp Thr Lys Val Ser
                805                 810                 815

Val Val Arg Gly Gln Phe Thr Ser Gln Leu Arg Arg Lys Trp Lys Ile
            820                 825                 830

Asp Lys Ser Arg Glu Thr Tyr His His His Ala Val Asp Ala Leu Ile
        835                 840                 845

Ile Ala Ala Ser Ser Gln Leu Lys Leu Trp Glu Lys Gln Asp Asn Pro
850                 855                 860

Met Phe Val Asp Tyr Gly Lys Asn Gln Val Val Asp Lys Gln Thr Gly
865                 870                 875                 880

Glu Ile Leu Ser Val Ser Asp Asp Glu Tyr Lys Glu Leu Val Phe Gln
                885                 890                 895

Pro Pro Tyr Gln Gly Phe Val Asn Thr Ile Ser Ser Lys Gly Phe Glu
            900                 905                 910

Asp Glu Ile Leu Phe Ser Tyr Gln Val Asp Ser Lys Tyr Asn Arg Lys
        915                 920                 925

Val Ser Asp Ala Thr Ile Tyr Ser Thr Arg Lys Ala Lys Ile Gly Lys
930                 935                 940

Asp Lys Lys Glu Glu Thr Tyr Val Leu Gly Lys Ile Lys Asp Ile Tyr
945                 950                 955                 960

Ser Gln Asn Gly Phe Asp Thr Phe Ile Lys Lys Tyr Asn Lys Asp Lys
                965                 970                 975

Thr Gln Phe Leu Met Tyr Gln Lys Asp Ser Leu Thr Trp Glu Asn Val
            980                 985                 990

Ile Glu Val Ile Leu Arg Asp Tyr Pro Thr Thr Lys Lys Ser Glu Asp
        995                 1000                1005

Gly Lys Asn Asp Val Lys Cys Asn Pro Phe Glu Glu Tyr Arg Arg
    1010                1015                1020

Glu Asn Gly Leu Ile Cys Lys Tyr Ser Lys Lys Gly Lys Gly Thr
    1025                1030                1035

Pro Ile Lys Ser Leu Lys Tyr Tyr Asp Lys Lys Leu Gly Asn Cys
    1040                1045                1050

Ile Asp Ile Thr Pro Glu Glu Ser Arg Asn Lys Val Ile Leu Gln
    1055                1060                1065

Ser Ile Asn Pro Trp Arg Ala Asp Val Tyr Phe Asn Pro Glu Thr
    1070                1075                1080

Leu Lys Tyr Glu Leu Met Gly Leu Lys Tyr Ser Asp Leu Ser Phe
    1085                1090                1095
```

Glu Lys Gly Thr Gly Asn Tyr His Ile Ser Gln Glu Lys Tyr Asp
     1100                1105                1110

Ala Ile Lys Glu Lys Glu Gly Ile Gly Lys Lys Ser Glu Phe Lys
    1115                1120                1125

Phe Thr Leu Tyr Arg Asn Asp Leu Ile Leu Ile Lys Asp Ile Ala
    1130                1135                1140

Ser Gly Glu Gln Glu Ile Tyr Arg Phe Leu Ser Arg Thr Met Pro
    1145                1150                1155

Asn Val Asn His Tyr Val Glu Leu Lys Pro Tyr Asp Lys Glu Lys
    1160                1165                1170

Phe Asp Asn Val Gln Glu Leu Val Glu Ala Leu Gly Glu Ala Asp
    1175                1180                1185

Lys Val Gly Arg Cys Ile Lys Gly Leu Asn Lys Pro Asn Ile Ser
    1190                1195                1200

Ile Tyr Lys Val Arg Thr Asp Val Leu Gly Asn Lys Tyr Phe Val
    1205                1210                1215

Lys Lys Lys Gly Asp Lys Pro Lys Leu Asp Phe Lys Asn Asn Lys
    1220                1225                1230

Lys Pro Lys Lys Lys Arg Lys Val Leu Glu Gly Gly Gly Gly Ser
    1235                1240                1245

Gly Lys Gly Asp Pro Lys Lys Pro Arg Gly Lys Met Ser Ser Tyr
    1250                1255                1260

Ala Phe Phe Val Gln Thr Cys Arg Glu Glu His Lys Lys Lys His
    1265                1270                1275

Pro Asp Ala Ser Val Asn Phe Ser Glu Phe Ser Lys Lys Cys Ser
    1280                1285                1290

Glu Arg Trp Lys Thr Met Ser Ala Lys Glu Lys Gly Lys Phe Glu
    1295                1300                1305

Asp Met Ala Lys Ala Asp Lys Ala Arg Tyr Glu Arg Glu Met Lys
    1310                1315                1320

Thr Tyr Ile Pro Pro Lys Gly Glu
    1325                1330

<210> SEQ ID NO 73
<211> LENGTH: 1328
<212> TYPE: PRT
<213> ORGANISM: Artificial Sequence
<220> FEATURE:
<223> OTHER INFORMATION: SYNTHESIZED

<400> SEQUENCE: 73

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Lys Val
            20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
        50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Thr Asn Gly Lys Ile Leu Gly
            100                 105                 110

```
Leu Asp Ile Gly Ile Ala Ser Gly Val Gly Ile Glu Ala Lys
        115                 120                 125

Thr Gly Lys Val Val His Ala Asn Ser Arg Leu Phe Ser Ala Ala Asn
130                 135                 140

Ala Glu Asn Asn Ala Glu Arg Arg Gly Phe Arg Gly Ser Arg Arg Leu
145                 150                 155                 160

Asn Arg Arg Lys Lys His Arg Val Lys Arg Val Arg Asp Leu Phe Glu
                165                 170                 175

Lys Tyr Gly Ile Val Thr Asp Phe Arg Asn Leu Asn Leu Asn Pro Tyr
                180                 185                 190

Glu Leu Arg Val Lys Gly Leu Thr Glu Gln Leu Lys Asn Glu Glu Leu
                195                 200                 205

Phe Ala Ala Leu Arg Thr Ile Ser Lys Arg Arg Gly Ile Ser Tyr Leu
210                 215                 220

Asp Asp Ala Glu Asp Ser Thr Gly Ser Thr Asp Tyr Ala Lys Ser
225                 230                 235                 240

Ile Asp Glu Asn Arg Arg Leu Leu Lys Asn Lys Thr Pro Gly Gln Ile
                245                 250                 255

Gln Leu Glu Arg Leu Glu Lys Tyr Gly Gln Leu Arg Gly Asn Phe Thr
                260                 265                 270

Val Tyr Asp Glu Asn Gly Glu Ala His Arg Leu Ile Asn Val Phe Ser
                275                 280                 285

Thr Ser Asp Tyr Glu Lys Glu Ala Arg Lys Ile Leu Glu Thr Gln Ala
                290                 295                 300

Asp Tyr Asn Lys Lys Ile Thr Ala Glu Phe Ile Asp Asp Tyr Val Glu
305                 310                 315                 320

Ile Leu Thr Gln Lys Arg Lys Tyr Tyr His Gly Pro Gly Asn Glu Lys
                325                 330                 335

Ser Arg Thr Asp Tyr Gly Arg Phe Arg Thr Asp Gly Thr Thr Leu Glu
                340                 345                 350

Asn Ile Phe Gly Ile Leu Ile Gly Lys Cys Asn Phe Tyr Pro Asp Glu
                355                 360                 365

Tyr Arg Ala Ser Lys Ala Ser Tyr Thr Ala Gln Glu Tyr Asn Phe Leu
                370                 375                 380

Asn Asp Leu Asn Asn Leu Lys Val Ser Thr Glu Thr Gly Lys Leu Ser
385                 390                 395                 400

Thr Glu Gln Lys Glu Ser Leu Val Glu Phe Ala Lys Asn Thr Ala Thr
                405                 410                 415

Leu Gly Pro Ala Lys Leu Leu Lys Glu Ile Ala Lys Ile Leu Asp Cys
                420                 425                 430

Lys Val Asp Glu Ile Lys Gly Tyr Arg Glu Asp Asp Lys Gly Lys Pro
                435                 440                 445

Asp Leu His Thr Phe Glu Pro Tyr Arg Lys Leu Lys Phe Asn Leu Glu
                450                 455                 460

Ser Ile Asn Ile Asp Asp Leu Ser Arg Glu Val Ile Asp Lys Leu Ala
465                 470                 475                 480

Asp Ile Leu Thr Leu Asn Thr Glu Arg Glu Gly Ile Glu Asp Ala Ile
                485                 490                 495

Lys Arg Asn Leu Pro Asn Gln Phe Thr Glu Gln Ile Ser Glu Ile
                500                 505                 510

Ile Lys Val Arg Lys Ser Gln Ser Thr Ala Phe Asn Lys Gly Trp His
                515                 520                 525

Ser Phe Ser Ala Lys Leu Met Asn Glu Leu Ile Pro Glu Leu Tyr Ala
```

```
                530             535             540
Thr Ser Asp Glu Gln Met Thr Ile Leu Thr Arg Leu Glu Lys Phe Lys
545                 550             555                 560

Val Asn Lys Lys Ser Ser Lys Asn Thr Lys Thr Ile Asp Glu Lys Glu
                565             570             575

Val Thr Asp Glu Ile Tyr Asn Pro Val Val Ala Lys Ser Val Arg Gln
                580             585             590

Thr Ile Lys Ile Ile Asn Ala Ala Val Lys Lys Tyr Gly Asp Phe Asp
                595             600             605

Lys Ile Val Ile Glu Met Pro Arg Asp Lys Asn Ala Asp Asp Glu Lys
                610             615             620

Lys Phe Ile Asp Lys Arg Asn Lys Glu Asn Lys Lys Glu Lys Asp Asp
625                 630             635                 640

Ala Leu Lys Arg Ala Ala Tyr Leu Tyr Asn Ser Ser Asp Lys Leu Pro
                645             650             655

Asp Glu Val Phe His Gly Asn Lys Gln Leu Glu Thr Lys Ile Arg Leu
                660             665             670

Trp Tyr Gln Gln Gly Glu Arg Cys Leu Tyr Ser Gly Lys Pro Ile Ser
                675             680             685

Ile Gln Glu Leu Val His Asn Ser Asn Asn Phe Glu Ile Asp His Ile
                690             695             700

Leu Pro Leu Ser Leu Ser Phe Asp Asp Ser Leu Ala Asn Lys Val Leu
705                 710             715                 720

Val Tyr Ala Trp Thr Asn Gln Glu Lys Gly Gln Lys Thr Pro Tyr Gln
                725             730             735

Val Ile Asp Ser Met Asp Ala Ala Trp Ser Phe Arg Glu Met Lys Asp
                740             745             750

Tyr Val Leu Lys Gln Lys Gly Leu Gly Lys Lys Arg Asp Tyr Leu
                755             760             765

Leu Thr Thr Glu Asn Ile Asp Lys Ile Glu Val Lys Lys Lys Phe Ile
770                 775             780

Glu Arg Asn Leu Val Asp Thr Arg Tyr Ala Ser Arg Val Val Leu Asn
785                 790             795                 800

Ser Leu Gln Ser Ala Leu Arg Glu Leu Gly Lys Asp Thr Lys Val Ser
                805             810             815

Val Val Arg Gly Gln Phe Thr Ser Gln Leu Arg Arg Lys Trp Lys Ile
                820             825             830

Asp Lys Ser Arg Glu Thr Tyr His His Ala Val Asp Ala Leu Ile
                835             840             845

Ile Ala Ala Ser Ser Gln Leu Lys Leu Trp Glu Lys Gln Asp Asn Pro
850                 855             860

Met Phe Val Asp Tyr Gly Lys Asn Gln Val Asp Lys Gln Thr Gly
865                 870             875             880

Glu Ile Leu Ser Val Ser Asp Asp Glu Tyr Lys Glu Leu Val Phe Gln
                885             890             895

Pro Pro Tyr Gln Gly Phe Val Asn Thr Ile Ser Ser Lys Gly Phe Glu
                900             905             910

Asp Glu Ile Leu Phe Ser Tyr Gln Val Asp Ser Lys Tyr Asn Arg Lys
                915             920             925

Val Ser Asp Ala Thr Ile Tyr Ser Thr Arg Lys Ala Lys Ile Gly Lys
                930             935             940

Asp Lys Lys Glu Glu Thr Tyr Val Leu Gly Lys Ile Lys Asp Ile Tyr
945                 950             955                 960
```

-continued

```
Ser Gln Asn Gly Phe Asp Thr Phe Ile Lys Lys Tyr Asn Lys Asp Lys
            965                 970                 975

Thr Gln Phe Leu Met Tyr Gln Lys Asp Ser Leu Thr Trp Glu Asn Val
        980                 985                 990

Ile Glu Val Ile Leu Arg Asp Tyr Pro Thr Thr Lys Lys Ser Glu Asp
    995                 1000                1005

Gly Lys Asn Asp Val Lys Cys Asn Pro Phe Glu Tyr Arg Arg
    1010                1015            1020

Glu Asn Gly Leu Ile Cys Lys Tyr Ser Lys Lys Gly Lys Gly Thr
    1025                1030            1035

Pro Ile Lys Ser Leu Lys Tyr Tyr Asp Lys Lys Leu Gly Asn Cys
    1040                1045            1050

Ile Asp Ile Thr Pro Glu Glu Ser Arg Asn Lys Val Ile Leu Gln
    1055                1060            1065

Ser Ile Asn Pro Trp Arg Ala Asp Val Tyr Phe Asn Pro Glu Thr
    1070                1075            1080

Leu Lys Tyr Glu Leu Met Gly Leu Lys Tyr Ser Asp Leu Ser Phe
    1085                1090            1095

Glu Lys Gly Thr Gly Asn Tyr His Ile Ser Gln Glu Lys Tyr Asp
    1100                1105            1110

Ala Ile Lys Glu Lys Glu Gly Ile Gly Lys Lys Ser Glu Phe Lys
    1115                1120            1125

Phe Thr Leu Tyr Arg Asn Asp Leu Ile Leu Ile Lys Asp Ile Ala
    1130                1135            1140

Ser Gly Glu Gln Glu Ile Tyr Arg Phe Leu Ser Arg Thr Met Pro
    1145                1150            1155

Asn Val Asn His Tyr Val Glu Leu Lys Pro Tyr Asp Lys Glu Lys
    1160                1165            1170

Phe Asp Asn Val Gln Glu Leu Val Glu Ala Leu Gly Glu Ala Asp
    1175                1180            1185

Lys Val Gly Arg Cys Ile Lys Gly Leu Asn Lys Pro Asn Ile Ser
    1190                1195            1200

Ile Tyr Lys Val Arg Thr Asp Val Leu Gly Asn Lys Tyr Phe Val
    1205                1210            1215

Lys Lys Lys Gly Asp Lys Pro Lys Leu Asp Phe Lys Asn Asn Lys
    1220                1225            1230

Lys Pro Lys Lys Arg Lys Val Leu Glu Gly Gly Gly Gly Ser
    1235                1240            1245

Ser Thr Asp His Pro Lys Tyr Ser Asp Met Ile Val Ala Ala Ile
    1250                1255            1260

Gln Ala Glu Lys Asn Arg Ala Gly Ser Ser Arg Gln Ser Ile Gln
    1265                1270            1275

Lys Tyr Ile Lys Ser His Tyr Lys Val Gly Glu Asn Ala Asp Ser
    1280                1285            1290

Gln Ile Lys Leu Ser Ile Lys Arg Leu Val Thr Thr Gly Val Leu
    1295                1300            1305

Lys Gln Thr Lys Gly Val Gly Ala Ser Gly Ser Phe Arg Leu Ala
    1310                1315            1320

Lys Ser Asp Glu Pro
    1325

<210> SEQ ID NO 74
<211> LENGTH: 1517
```

<212> TYPE: PRT
<213> ORGANISM: Artificial Sequence
<220> FEATURE:
<223> OTHER INFORMATION: SYNTHESIZED

<400> SEQUENCE: 74

| | | | | | | | | | | | | | | |
|---|---|---|---|---|---|---|---|---|---|---|---|---|---|---|
| Met | Pro | Lys | Arg | Lys | Val | Ser | Ser | Ala | Glu | Gly | Ala | Ala | Lys | Glu |
| 1 | | | | 5 | | | | | 10 | | | | | 15 |
| Glu | Pro | Lys | Arg | Arg | Ser | Ala | Arg | Leu | Ser | Ala | Lys | Pro | Ala | Lys |
| | | | 20 | | | | | 25 | | | | | 30 | |
| Val | Glu | Ala | Lys | Pro | Lys | Lys | Ala | Ala | Ala | Lys | Asp | Lys | Ser | Ser |
| | | | 35 | | | | | 40 | | | | | 45 | |
| Asp | Lys | Lys | Val | Gln | Thr | Lys | Gly | Lys | Arg | Gly | Ala | Lys | Gly | Lys |
| | | | 50 | | | | | 55 | | | | | 60 | |
| Gln | Ala | Glu | Val | Ala | Asn | Gln | Glu | Thr | Lys | Glu | Asp | Leu | Pro | Ala |
| 65 | | | | | 70 | | | | | 75 | | | | | 80 |
| Glu | Asn | Gly | Glu | Thr | Lys | Thr | Glu | Glu | Ser | Pro | Ala | Ser | Asp | Glu |
| | | | | 85 | | | | | 90 | | | | | 95 |
| Ala | Gly | Glu | Lys | Glu | Ala | Lys | Ser | Asp | Thr | Gly | Ser | Gly | Met | Thr |
| | | | | 100 | | | | | 105 | | | | | 110 |
| Asn | Gly | Lys | Ile | Leu | Gly | Leu | Asp | Ile | Gly | Ile | Ala | Ser | Val | Gly |
| | | | | | | | 115 | | | | | 120 | | |
| Val | Gly | Ile | Ile | Glu | Ala | Lys | Thr | Gly | Lys | Val | Val | His | Ala | Asn |
| | | | | 125 | | | | | 130 | | | | | 135 |
| Ser | Arg | Leu | Phe | Ser | Ala | Ala | Asn | Ala | Glu | Asn | Asn | Ala | Glu | Arg |
| | | | 140 | | | | | 145 | | | | | 150 | |
| Arg | Gly | Phe | Arg | Gly | Ser | Arg | Arg | Leu | Asn | Arg | Arg | Lys | Lys | His |
| | | | 155 | | | | | 160 | | | | | 165 | |
| Arg | Val | Lys | Arg | Val | Arg | Asp | Leu | Phe | Glu | Lys | Tyr | Gly | Ile | Val |
| | | | 170 | | | | | 175 | | | | | 180 | |
| Thr | Asp | Phe | Arg | Asn | Leu | Asn | Leu | Asn | Pro | Tyr | Glu | Leu | Arg | Val |
| | | | 185 | | | | | 190 | | | | | 195 | |
| Lys | Gly | Leu | Thr | Glu | Gln | Leu | Lys | Asn | Glu | Glu | Leu | Phe | Ala | Ala |
| | | | 200 | | | | | 205 | | | | | 210 | |
| Leu | Arg | Thr | Ile | Ser | Lys | Arg | Arg | Gly | Ile | Ser | Tyr | Leu | Asp | Asp |
| | | | 215 | | | | | 220 | | | | | 225 | |
| Ala | Glu | Asp | Asp | Ser | Thr | Gly | Ser | Thr | Asp | Tyr | Ala | Lys | Ser | Ile |
| | | 230 | | | | | 235 | | | | | 240 | | |
| Asp | Glu | Asn | Arg | Arg | Leu | Leu | Lys | Asn | Lys | Thr | Pro | Gly | Gln | Ile |
| | | | 245 | | | | | 250 | | | | | 255 | |
| Gln | Leu | Glu | Arg | Leu | Glu | Lys | Tyr | Gly | Gln | Leu | Arg | Gly | Asn | Phe |
| | | | 260 | | | | | 265 | | | | | 270 | |
| Thr | Val | Tyr | Asp | Glu | Asn | Gly | Glu | Ala | His | Arg | Leu | Ile | Asn | Val |
| | | 275 | | | | | 280 | | | | | 285 | | |
| Phe | Ser | Thr | Ser | Asp | Tyr | Glu | Lys | Glu | Ala | Arg | Lys | Ile | Leu | Glu |
| | | | 290 | | | | | 295 | | | | | 300 | |
| Thr | Gln | Ala | Asp | Tyr | Asn | Lys | Lys | Ile | Thr | Ala | Glu | Phe | Ile | Asp |
| 305 | | | | | 310 | | | | | 315 | | | | |
| Tyr | Val | Glu | Ile | Leu | Thr | Gln | Lys | Arg | Lys | Tyr | Tyr | His | Gly | Pro |
| | | 320 | | | | | 325 | | | | | 330 | | |
| Gly | Asn | Glu | Lys | Ser | Arg | Thr | Asp | Tyr | Gly | Arg | Phe | Arg | Thr | Asp |
| | | | 335 | | | | | 340 | | | | | 345 | |
| Gly | Thr | Thr | Leu | Glu | Asn | Ile | Phe | Gly | Ile | Leu | Ile | Gly | Lys | Cys |
| | | 350 | | | | | 355 | | | | | 360 | | |
| Asn | Phe | Tyr | Pro | Asp | Glu | Tyr | Arg | Ala | Ser | Lys | Ala | Ser | Tyr | Thr |
| | | 365 | | | | | 370 | | | | | 375 | | |
| Ala | Gln | Glu | Tyr | Asn | Phe | Leu | | | | | | | | |
| | | 380 | | | | | | | | | | | | |

```
Asn Asp Leu Asn Asn Leu Lys Val Ser Thr Glu Thr Gly Lys Leu Ser
385                 390                 395                 400

Thr Glu Gln Lys Glu Ser Leu Val Glu Phe Ala Lys Asn Thr Ala Thr
                405                 410                 415

Leu Gly Pro Ala Lys Leu Leu Lys Glu Ile Ala Lys Ile Leu Asp Cys
            420                 425                 430

Lys Val Asp Glu Ile Lys Gly Tyr Arg Glu Asp Lys Gly Lys Pro
                435                 440                 445

Asp Leu His Thr Phe Glu Pro Tyr Arg Lys Leu Lys Phe Asn Leu Glu
        450                 455                 460

Ser Ile Asn Ile Asp Asp Leu Ser Arg Glu Val Ile Asp Lys Leu Ala
465                 470                 475                 480

Asp Ile Leu Thr Leu Asn Thr Glu Arg Glu Gly Ile Glu Asp Ala Ile
            485                 490                 495

Lys Arg Asn Leu Pro Asn Gln Phe Thr Glu Glu Gln Ile Ser Glu Ile
                500                 505                 510

Ile Lys Val Arg Lys Ser Gln Ser Thr Ala Phe Asn Lys Gly Trp His
            515                 520                 525

Ser Phe Ser Ala Lys Leu Met Asn Glu Leu Ile Pro Glu Leu Tyr Ala
530                 535                 540

Thr Ser Asp Glu Gln Met Thr Ile Leu Thr Arg Leu Glu Lys Phe Lys
545                 550                 555                 560

Val Asn Lys Lys Ser Ser Lys Asn Thr Lys Thr Ile Asp Glu Lys Glu
                565                 570                 575

Val Thr Asp Glu Ile Tyr Asn Pro Val Val Ala Lys Ser Val Arg Gln
                580                 585                 590

Thr Ile Lys Ile Ile Asn Ala Ala Val Lys Lys Tyr Gly Asp Phe Asp
            595                 600                 605

Lys Ile Val Ile Glu Met Pro Arg Asp Lys Asn Ala Asp Asp Glu Lys
            610                 615                 620

Lys Phe Ile Asp Lys Arg Asn Lys Glu Asn Lys Lys Glu Lys Asp Asp
625                 630                 635                 640

Ala Leu Lys Arg Ala Ala Tyr Leu Tyr Asn Ser Ser Asp Lys Leu Pro
                645                 650                 655

Asp Glu Val Phe His Gly Asn Lys Gln Leu Glu Thr Lys Ile Arg Leu
                660                 665                 670

Trp Tyr Gln Gln Gly Glu Arg Cys Leu Tyr Ser Gly Lys Pro Ile Ser
        675                 680                 685

Ile Gln Glu Leu Val His Asn Ser Asn Phe Glu Ile Asp His Ile Ile
        690                 695                 700

Leu Pro Leu Ser Leu Ser Phe Asp Asp Ser Leu Ala Asn Lys Val Leu
705                 710                 715                 720

Val Tyr Ala Trp Thr Asn Gln Glu Lys Gly Gln Lys Thr Pro Tyr Gln
                725                 730                 735

Val Ile Asp Ser Met Asp Ala Ala Trp Ser Phe Arg Glu Met Lys Asp
            740                 745                 750

Tyr Val Leu Lys Gln Lys Gly Leu Gly Lys Lys Arg Asp Tyr Leu
                755                 760                 765

Leu Thr Thr Glu Asn Ile Asp Lys Ile Glu Val Lys Lys Lys Phe Ile
        770                 775                 780

Glu Arg Asn Leu Val Asp Thr Arg Tyr Ala Ser Arg Val Val Leu Asn
785                 790                 795                 800

Ser Leu Gln Ser Ala Leu Arg Glu Leu Gly Lys Asp Thr Lys Val Ser
```

```
            805                 810                 815
Val Val Arg Gly Gln Phe Thr Ser Gln Leu Arg Arg Lys Trp Lys Ile
            820                 825                 830

Asp Lys Ser Arg Glu Thr Tyr His His His Ala Val Asp Ala Leu Ile
            835                 840                 845

Ile Ala Ala Ser Ser Gln Leu Lys Leu Trp Glu Lys Gln Asp Asn Pro
850                 855                 860

Met Phe Val Asp Tyr Gly Lys Asn Gln Val Val Asp Lys Gln Thr Gly
865                 870                 875                 880

Glu Ile Leu Ser Val Ser Asp Asp Glu Tyr Lys Glu Leu Val Phe Gln
                    885                 890                 895

Pro Pro Tyr Gln Gly Phe Val Asn Thr Ile Ser Ser Lys Gly Phe Glu
                    900                 905                 910

Asp Glu Ile Leu Phe Ser Tyr Gln Val Asp Ser Lys Tyr Asn Arg Lys
                    915                 920                 925

Val Ser Asp Ala Thr Ile Tyr Ser Thr Arg Lys Ala Lys Ile Gly Lys
930                 935                 940

Asp Lys Lys Glu Glu Thr Tyr Val Leu Gly Lys Ile Lys Asp Ile Tyr
945                 950                 955                 960

Ser Gln Asn Gly Phe Asp Thr Phe Ile Lys Lys Tyr Asn Lys Asp Lys
                    965                 970                 975

Thr Gln Phe Leu Met Tyr Gln Lys Asp Ser Leu Thr Trp Glu Asn Val
                    980                 985                 990

Ile Glu Val Ile Leu Arg Asp Tyr Pro Thr Thr Lys Lys Ser Glu Asp
                    995                 1000                1005

Gly Lys Asn Asp Val Lys Cys Asn Pro Phe Glu Glu Tyr Arg Arg
        1010                1015                1020

Glu Asn Gly Leu Ile Cys Lys Tyr Ser Lys Lys Gly Lys Gly Thr
        1025                1030                1035

Pro Ile Lys Ser Leu Lys Tyr Tyr Asp Lys Lys Leu Gly Asn Cys
        1040                1045                1050

Ile Asp Ile Thr Pro Glu Glu Ser Arg Asn Lys Val Ile Leu Gln
        1055                1060                1065

Ser Ile Asn Pro Trp Arg Ala Asp Val Tyr Phe Asn Pro Glu Thr
        1070                1075                1080

Leu Lys Tyr Glu Leu Met Gly Leu Lys Tyr Ser Asp Leu Ser Phe
        1085                1090                1095

Glu Lys Gly Thr Gly Asn Tyr His Ile Ser Gln Glu Lys Tyr Asp
        1100                1105                1110

Ala Ile Lys Glu Lys Glu Gly Ile Gly Lys Lys Ser Glu Phe Lys
        1115                1120                1125

Phe Thr Leu Tyr Arg Asn Asp Leu Ile Leu Ile Lys Asp Ile Ala
        1130                1135                1140

Ser Gly Glu Gln Glu Ile Tyr Arg Phe Leu Ser Arg Thr Met Pro
        1145                1150                1155

Asn Val Asn His Tyr Val Glu Leu Lys Pro Tyr Asp Lys Glu Lys
        1160                1165                1170

Phe Asp Asn Val Gln Glu Leu Val Glu Ala Leu Gly Glu Ala Asp
        1175                1180                1185

Lys Val Gly Arg Cys Ile Lys Gly Leu Asn Lys Pro Asn Ile Ser
        1190                1195                1200

Ile Tyr Lys Val Arg Thr Asp Val Leu Gly Asn Lys Tyr Phe Val
        1205                1210                1215
```

Lys Lys Lys Gly Asp Lys Pro Lys Leu Asp Phe Lys Asn Asn Lys
1220            1225                1230

Lys Pro Lys Lys Arg Lys Val Leu Glu Gly Gly Gly Ser
    1235            1240            1245

Asp Met Asp Ser Ile Gly Glu Ser Glu Val Arg Ala Leu Tyr Lys
    1250            1255                1260

Ala Ile Leu Lys Phe Gly Asn Leu Lys Glu Ile Leu Asp Glu Leu
    1265            1270                1275

Ile Ala Asp Gly Thr Leu Pro Val Lys Ser Phe Glu Lys Tyr Gly
    1280            1285                1290

Glu Thr Tyr Asp Glu Met Met Glu Ala Ala Lys Asp Cys Val His
    1295            1300                1305

Glu Glu Glu Lys Asn Arg Lys Glu Ile Leu Glu Lys Leu Glu Lys
    1310            1315                1320

His Ala Thr Ala Tyr Arg Ala Lys Leu Lys Ser Gly Glu Ile Lys
    1325            1330                1335

Ala Glu Asn Gln Pro Lys Asp Asn Pro Leu Thr Arg Leu Ser Leu
    1340            1345                1350

Lys Lys Arg Glu Lys Lys Ala Val Leu Phe Asn Phe Lys Gly Val
    1355            1360                1365

Lys Ser Leu Asn Ala Glu Ser Leu Leu Ser Arg Val Glu Asp Leu
    1370            1375                1380

Lys Tyr Leu Lys Asn Leu Ile Asn Ser Asn Tyr Lys Asp Asp Pro
    1385            1390                1395

Leu Lys Phe Ser Leu Gly Asn Asn Thr Pro Lys Pro Val Gln Asn
    1400            1405                1410

Trp Ser Ser Asn Trp Thr Lys Glu Glu Asp Glu Lys Leu Leu Ile
    1415            1420                1425

Gly Val Phe Lys Tyr Gly Tyr Gly Ser Trp Thr Gln Ile Arg Asp
    1430            1435                1440

Asp Pro Phe Leu Gly Ile Thr Asp Lys Ile Phe Leu Asn Glu Val
    1445            1450                1455

His Asn Pro Val Ala Lys Lys Ser Ala Ser Ser Ser Asp Thr Thr
    1460            1465                1470

Pro Thr Pro Ser Lys Lys Gly Lys Gly Ile Thr Gly Ser Ser Lys
    1475            1480                1485

Lys Val Pro Gly Ala Ile His Leu Gly Arg Arg Val Asp Tyr Leu
    1490            1495                1500

Leu Ser Phe Leu Arg Gly Gly Leu Asn Thr Lys Ser Pro Ser
    1505            1510                1515

<210> SEQ ID NO 75
<211> LENGTH: 1501
<212> TYPE: PRT
<213> ORGANISM: Artificial Sequence
<220> FEATURE:
<223> OTHER INFORMATION: SYNTHESIZED

<400> SEQUENCE: 75

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Lys Val
            20                  25                  30

Glu Ala Lys Pro Lys Lys Ala Ala Ala Lys Asp Lys Ser Ser Asp Lys
        35                  40                  45

```
Lys Val Gln Thr Lys Gly Lys Arg Gly Ala Lys Gly Lys Gln Ala Glu
            50                  55                  60

Val Ala Asn Gln Glu Thr Lys Glu Asp Leu Pro Ala Glu Asn Gly Glu
 65                  70                  75                  80

Thr Lys Thr Glu Glu Ser Pro Ala Ser Asp Glu Ala Gly Glu Lys Glu
                    85                  90                  95

Ala Lys Ser Asp Thr Gly Ser Gly Met Ser Ile Tyr Gln Glu Phe Val
                100                 105                 110

Asn Lys Tyr Ser Leu Ser Lys Thr Leu Arg Phe Glu Leu Ile Pro Gln
                115                 120                 125

Gly Lys Thr Leu Glu Asn Ile Lys Ala Arg Gly Leu Ile Leu Asp Asp
            130                 135                 140

Glu Lys Arg Ala Lys Asp Tyr Lys Lys Ala Lys Gln Ile Ile Asp Lys
145                 150                 155                 160

Tyr His Gln Phe Phe Ile Glu Glu Ile Leu Ser Ser Val Cys Ile Ser
                    165                 170                 175

Glu Asp Leu Leu Gln Asn Tyr Ser Asp Val Tyr Phe Lys Leu Lys Lys
                180                 185                 190

Ser Asp Asp Asn Leu Gln Lys Asp Phe Lys Ser Ala Lys Asp Thr
                195                 200                 205

Ile Lys Lys Gln Ile Ser Glu Tyr Ile Lys Asp Ser Glu Lys Phe Lys
    210                 215                 220

Asn Leu Phe Asn Gln Asn Leu Ile Asp Ala Lys Lys Gly Gln Glu Ser
225                 230                 235                 240

Asp Leu Ile Leu Trp Leu Lys Gln Ser Lys Asp Asn Gly Ile Glu Leu
                245                 250                 255

Phe Lys Ala Asn Ser Asp Ile Thr Asp Ile Asp Glu Ala Leu Glu Ile
                260                 265                 270

Ile Lys Ser Phe Lys Gly Trp Thr Thr Tyr Phe Lys Gly Phe His Glu
                275                 280                 285

Asn Arg Lys Asn Val Tyr Ser Ser Asn Asp Ile Pro Thr Ser Ile Ile
            290                 295                 300

Tyr Arg Ile Val Asp Asp Asn Leu Pro Lys Phe Leu Glu Asn Lys Ala
305                 310                 315                 320

Lys Tyr Glu Ser Leu Lys Asp Lys Ala Pro Glu Ala Ile Asn Tyr Glu
                325                 330                 335

Gln Ile Lys Lys Asp Leu Ala Glu Glu Leu Thr Phe Asp Ile Asp Tyr
                340                 345                 350

Lys Thr Ser Glu Val Asn Gln Arg Val Phe Ser Leu Asp Glu Val Phe
            355                 360                 365

Glu Ile Ala Asn Phe Asn Asn Tyr Leu Asn Gln Ser Gly Ile Thr Lys
    370                 375                 380

Phe Asn Thr Ile Ile Gly Gly Lys Phe Val Asn Gly Glu Asn Thr Lys
385                 390                 395                 400

Arg Lys Gly Ile Asn Glu Tyr Ile Asn Leu Tyr Ser Gln Gln Ile Asn
                405                 410                 415

Asp Lys Thr Leu Lys Lys Tyr Lys Met Ser Val Leu Phe Lys Gln Ile
                420                 425                 430

Leu Ser Asp Thr Glu Ser Lys Ser Phe Val Ile Asp Lys Leu Glu Asp
            435                 440                 445

Asp Ser Asp Val Val Thr Thr Met Gln Ser Phe Tyr Glu Gln Ile Ala
    450                 455                 460
```

```
Ala Phe Lys Thr Val Glu Glu Lys Ser Ile Lys Glu Thr Leu Ser Leu
465                 470                 475                 480

Leu Phe Asp Asp Leu Lys Ala Gln Lys Leu Asp Leu Ser Lys Ile Tyr
            485                 490                 495

Phe Lys Asn Asp Lys Ser Leu Thr Asp Leu Ser Gln Gln Val Phe Asp
        500                 505                 510

Asp Tyr Ser Val Ile Gly Thr Ala Val Leu Glu Tyr Ile Thr Gln Gln
        515                 520                 525

Ile Ala Pro Lys Asn Leu Asp Asn Pro Ser Lys Lys Glu Gln Glu Leu
        530                 535                 540

Ile Ala Lys Lys Thr Glu Lys Ala Lys Tyr Leu Ser Leu Glu Thr Ile
545                 550                 555                 560

Lys Leu Ala Leu Glu Glu Phe Asn Lys His Arg Asp Ile Asp Lys Gln
            565                 570                 575

Cys Arg Phe Glu Glu Ile Leu Ala Asn Phe Ala Ala Ile Pro Met Ile
            580                 585                 590

Phe Asp Glu Ile Ala Gln Asn Lys Asp Asn Leu Ala Gln Ile Ser Ile
        595                 600                 605

Lys Tyr Gln Asn Gln Gly Lys Lys Asp Leu Leu Gln Ala Ser Ala Glu
        610                 615                 620

Asp Asp Val Lys Ala Ile Lys Asp Leu Leu Asp Gln Thr Asn Asn Leu
625                 630                 635                 640

Leu His Lys Leu Lys Ile Phe His Ile Ser Gln Ser Glu Asp Lys Ala
            645                 650                 655

Asn Ile Leu Asp Lys Asp Glu His Phe Tyr Leu Val Phe Glu Glu Cys
            660                 665                 670

Tyr Phe Glu Leu Ala Asn Ile Val Pro Leu Tyr Asn Lys Ile Arg Asn
        675                 680                 685

Tyr Ile Thr Gln Lys Pro Tyr Ser Asp Glu Lys Phe Lys Leu Asn Phe
        690                 695                 700

Glu Asn Ser Thr Leu Ala Asn Gly Trp Asp Lys Asn Lys Glu Pro Asp
705                 710                 715                 720

Asn Thr Ala Ile Leu Phe Ile Lys Asp Asp Lys Tyr Tyr Leu Gly Val
            725                 730                 735

Met Asn Lys Lys Asn Asn Lys Ile Phe Asp Asp Lys Ala Ile Lys Glu
            740                 745                 750

Asn Lys Gly Glu Gly Tyr Lys Lys Ile Val Tyr Lys Leu Leu Pro Gly
        755                 760                 765

Ala Asn Lys Met Leu Pro Lys Val Phe Ser Ala Lys Ser Ile Lys
        770                 775                 780

Phe Tyr Asn Pro Ser Glu Asp Ile Leu Arg Ile Arg Asn His Ser Thr
785                 790                 795                 800

His Thr Lys Asn Gly Ser Pro Gln Lys Gly Tyr Glu Lys Phe Glu Phe
            805                 810                 815

Asn Ile Glu Asp Cys Arg Lys Phe Ile Asp Phe Tyr Lys Gln Ser Ile
            820                 825                 830

Ser Lys His Pro Glu Trp Lys Asp Phe Gly Phe Arg Phe Ser Asp Thr
        835                 840                 845

Gln Arg Tyr Asn Ser Ile Asp Glu Phe Tyr Arg Glu Val Glu Asn Gln
        850                 855                 860

Gly Tyr Lys Leu Thr Phe Glu Asn Ile Ser Glu Ser Tyr Ile Asp Ser
865                 870                 875                 880

Val Val Asn Gln Gly Lys Leu Tyr Leu Phe Gln Ile Tyr Asn Lys Asp
```

```
                    885                 890                 895
Phe Ser Ala Tyr Ser Lys Gly Arg Pro Asn Leu His Thr Leu Tyr Trp
                900                 905                 910
Lys Ala Leu Phe Asp Glu Arg Asn Leu Gln Asp Val Val Tyr Lys Leu
                915                 920                 925
Asn Gly Glu Ala Glu Leu Phe Tyr Arg Lys Gln Ser Ile Pro Lys Lys
                930                 935                 940
Ile Thr His Pro Ala Lys Glu Ala Ile Ala Asn Lys Asn Lys Asp Asn
945                 950                 955                 960
Pro Lys Lys Glu Ser Val Phe Glu Tyr Asp Leu Ile Lys Asp Lys Arg
                965                 970                 975
Phe Thr Glu Asp Lys Phe Phe Phe His Cys Pro Ile Thr Ile Asn Phe
                980                 985                 990
Lys Ser Ser Gly Ala Asn Lys Phe Asn Asp Glu Ile Asn Leu Leu Leu
                995                 1000                1005
Lys Glu Lys Ala Asn Asp Val His Ile Leu Ser Ile Asp Arg Gly
        1010                1015                1020
Glu Arg His Leu Ala Tyr Tyr Thr Leu Val Asp Gly Lys Gly Asn
        1025                1030                1035
Ile Ile Lys Gln Asp Thr Phe Asn Ile Ile Gly Asn Asp Arg Met
        1040                1045                1050
Lys Thr Asn Tyr His Asp Lys Leu Ala Ala Ile Glu Lys Asp Arg
        1055                1060                1065
Asp Ser Ala Arg Lys Asp Trp Lys Lys Ile Asn Asn Ile Lys Glu
        1070                1075                1080
Met Lys Glu Gly Tyr Leu Ser Gln Val Val His Glu Ile Ala Lys
        1085                1090                1095
Leu Val Ile Glu Tyr Asn Ala Ile Val Val Phe Glu Asp Leu Asn
        1100                1105                1110
Phe Gly Phe Lys Arg Gly Arg Phe Lys Val Glu Lys Gln Val Tyr
        1115                1120                1125
Gln Lys Leu Glu Lys Met Leu Ile Glu Lys Leu Asn Tyr Leu Val
        1130                1135                1140
Phe Lys Asp Asn Glu Phe Asp Lys Thr Gly Gly Val Leu Arg Ala
        1145                1150                1155
Tyr Gln Leu Thr Ala Pro Phe Glu Thr Phe Lys Lys Met Gly Lys
        1160                1165                1170
Gln Thr Gly Ile Ile Tyr Tyr Val Pro Ala Gly Phe Thr Ser Lys
        1175                1180                1185
Ile Cys Pro Val Thr Gly Phe Val Asn Gln Leu Tyr Pro Lys Tyr
        1190                1195                1200
Glu Ser Val Ser Lys Ser Gln Glu Phe Phe Ser Lys Phe Asp Lys
        1205                1210                1215
Ile Cys Tyr Asn Leu Asp Lys Gly Tyr Phe Glu Phe Ser Phe Asp
        1220                1225                1230
Tyr Lys Asn Phe Gly Asp Lys Ala Ala Lys Gly Lys Trp Thr Ile
        1235                1240                1245
Ala Ser Phe Gly Ser Arg Leu Ile Asn Phe Arg Asn Ser Asp Lys
        1250                1255                1260
Asn His Asn Trp Asp Thr Arg Glu Val Tyr Pro Thr Lys Glu Leu
        1265                1270                1275
Glu Lys Leu Leu Lys Asp Tyr Ser Ile Glu Tyr Gly His Gly Glu
        1280                1285                1290
```

```
Cys Ile Lys Ala Ala Ile Cys Gly Glu Ser Asp Lys Lys Phe Phe
    1295                1300                1305

Ala Lys Leu Thr Ser Val Leu Asn Thr Ile Leu Gln Met Arg Asn
    1310                1315                1320

Ser Lys Thr Gly Thr Glu Leu Asp Tyr Leu Ile Ser Pro Val Ala
    1325                1330                1335

Asp Val Asn Gly Asn Phe Phe Asp Ser Arg Gln Ala Pro Lys Asn
    1340                1345                1350

Met Pro Gln Asp Ala Asp Ala Asn Gly Ala Tyr His Ile Gly Leu
    1355                1360                1365

Lys Gly Leu Met Leu Leu Gly Arg Ile Lys Asn Asn Gln Glu Gly
    1370                1375                1380

Lys Lys Leu Asn Leu Val Ile Lys Asn Glu Glu Tyr Phe Glu Phe
    1385                1390                1395

Val Gln Asn Arg Asn Asn Pro Lys Lys Lys Arg Lys Val Leu Glu
    1400                1405                1410

Gly Gly Gly Gly Ser Gly Lys Gly Asp Pro Lys Lys Pro Arg Gly
    1415                1420                1425

Lys Met Ser Ser Tyr Ala Phe Phe Val Gln Thr Cys Arg Glu Glu
    1430                1435                1440

His Lys Lys Lys His Pro Asp Ala Ser Val Asn Phe Ser Glu Phe
    1445                1450                1455

Ser Lys Lys Cys Ser Glu Arg Trp Lys Thr Met Ser Ala Lys Glu
    1460                1465                1470

Lys Gly Lys Phe Glu Asp Met Ala Lys Ala Asp Lys Ala Arg Tyr
    1475                1480                1485

Glu Arg Glu Met Lys Thr Tyr Ile Pro Pro Lys Gly Glu
    1490                1495                1500

<210> SEQ ID NO 76
<211> LENGTH: 1498
<212> TYPE: PRT
<213> ORGANISM: Artificial Sequence
<220> FEATURE:
<223> OTHER INFORMATION: SYNTHESIZED

<400> SEQUENCE: 76

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Lys Val
            20                  25                  30

Glu Ala Lys Pro Lys Lys Ala Ala Ala Lys Asp Lys Ser Ser Asp Lys
        35                  40                  45

Lys Val Gln Thr Lys Gly Lys Arg Gly Ala Lys Gly Lys Gln Ala Glu
    50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Lys Glu
                85                  90                  95

Ala Lys Ser Asp Thr Gly Ser Gly Met Ser Ile Tyr Gln Glu Phe Val
            100                 105                 110

Asn Lys Tyr Ser Leu Ser Lys Thr Leu Arg Phe Glu Leu Ile Pro Gln
        115                 120                 125

Gly Lys Thr Leu Glu Asn Ile Lys Ala Arg Gly Leu Ile Leu Asp Asp
    130                 135                 140
```

```
Glu Lys Arg Ala Lys Asp Tyr Lys Ala Lys Gln Ile Ile Asp Lys
145                 150                 155                 160

Tyr His Gln Phe Phe Ile Glu Glu Ile Leu Ser Ser Val Cys Ile Ser
                165                 170                 175

Glu Asp Leu Leu Gln Asn Tyr Ser Asp Val Tyr Phe Lys Leu Lys Lys
            180                 185                 190

Ser Asp Asp Asn Leu Gln Lys Asp Phe Lys Ser Ala Lys Asp Thr
        195                 200                 205

Ile Lys Lys Gln Ile Ser Glu Tyr Ile Lys Asp Ser Glu Lys Phe Lys
210                 215                 220

Asn Leu Phe Asn Gln Asn Leu Ile Asp Ala Lys Lys Gly Gln Glu Ser
225                 230                 235                 240

Asp Leu Ile Leu Trp Leu Lys Gln Ser Lys Asp Asn Gly Ile Glu Leu
            245                 250                 255

Phe Lys Ala Asn Ser Asp Ile Thr Asp Ile Asp Glu Ala Leu Glu Ile
                260                 265                 270

Ile Lys Ser Phe Lys Gly Trp Thr Thr Tyr Phe Lys Gly Phe His Glu
        275                 280                 285

Asn Arg Lys Asn Val Tyr Ser Ser Asn Asp Ile Pro Thr Ser Ile Ile
290                 295                 300

Tyr Arg Ile Val Asp Asp Asn Leu Pro Lys Phe Leu Glu Asn Lys Ala
305                 310                 315                 320

Lys Tyr Glu Ser Leu Lys Asp Lys Ala Pro Glu Ala Ile Asn Tyr Glu
            325                 330                 335

Gln Ile Lys Lys Asp Leu Ala Glu Glu Leu Thr Phe Asp Ile Asp Tyr
                340                 345                 350

Lys Thr Ser Glu Val Asn Gln Arg Val Phe Ser Leu Asp Glu Val Phe
        355                 360                 365

Glu Ile Ala Asn Phe Asn Asn Tyr Leu Asn Gln Ser Gly Ile Thr Lys
        370                 375                 380

Phe Asn Thr Ile Ile Gly Gly Lys Phe Val Asn Gly Glu Asn Thr Lys
385                 390                 395                 400

Arg Lys Gly Ile Asn Glu Tyr Ile Asn Leu Tyr Ser Gln Gln Ile Asn
            405                 410                 415

Asp Lys Thr Leu Lys Lys Tyr Lys Met Ser Val Leu Phe Lys Gln Ile
        420                 425                 430

Leu Ser Asp Thr Glu Ser Lys Ser Phe Val Ile Asp Lys Leu Glu Asp
    435                 440                 445

Asp Ser Asp Val Val Thr Thr Met Gln Ser Phe Tyr Glu Gln Ile Ala
    450                 455                 460

Ala Phe Lys Thr Val Glu Glu Lys Ser Ile Lys Glu Thr Leu Ser Leu
465                 470                 475                 480

Leu Phe Asp Asp Leu Lys Ala Gln Lys Leu Asp Leu Ser Lys Ile Tyr
            485                 490                 495

Phe Lys Asn Asp Lys Ser Leu Thr Asp Leu Ser Gln Val Phe Asp
            500                 505                 510

Asp Tyr Ser Val Ile Gly Thr Ala Val Leu Glu Tyr Ile Thr Gln Gln
        515                 520                 525

Ile Ala Pro Lys Asn Leu Asp Asn Pro Ser Lys Lys Glu Gln Glu Leu
        530                 535                 540

Ile Ala Lys Lys Thr Glu Lys Ala Lys Tyr Leu Ser Leu Glu Thr Ile
545                 550                 555                 560
```

```
Lys Leu Ala Leu Glu Glu Phe Asn Lys His Arg Asp Ile Asp Lys Gln
                565                 570                 575

Cys Arg Phe Glu Glu Ile Leu Ala Asn Phe Ala Ala Ile Pro Met Ile
            580                 585                 590

Phe Asp Glu Ile Ala Gln Asn Lys Asp Asn Leu Ala Gln Ile Ser Ile
        595                 600                 605

Lys Tyr Gln Asn Gln Gly Lys Lys Asp Leu Leu Gln Ala Ser Ala Glu
    610                 615                 620

Asp Asp Val Lys Ala Ile Lys Asp Leu Leu Asp Gln Thr Asn Asn Leu
625                 630                 635                 640

Leu His Lys Leu Lys Ile Phe His Ile Ser Gln Ser Glu Asp Lys Ala
                645                 650                 655

Asn Ile Leu Asp Lys Asp Glu His Phe Tyr Leu Val Phe Glu Glu Cys
            660                 665                 670

Tyr Phe Glu Leu Ala Asn Ile Val Pro Leu Tyr Asn Lys Ile Arg Asn
        675                 680                 685

Tyr Ile Thr Gln Lys Pro Tyr Ser Asp Glu Lys Phe Lys Leu Asn Phe
    690                 695                 700

Glu Asn Ser Thr Leu Ala Asn Gly Trp Asp Lys Asn Lys Glu Pro Asp
705                 710                 715                 720

Asn Thr Ala Ile Leu Phe Ile Lys Asp Lys Tyr Tyr Leu Gly Val
                725                 730                 735

Met Asn Lys Lys Asn Asn Lys Ile Phe Asp Asp Lys Ala Ile Lys Glu
            740                 745                 750

Asn Lys Gly Glu Gly Tyr Lys Lys Ile Val Tyr Lys Leu Leu Pro Gly
        755                 760                 765

Ala Asn Lys Met Leu Pro Lys Val Phe Phe Ser Ala Lys Ser Ile Lys
    770                 775                 780

Phe Tyr Asn Pro Ser Glu Asp Ile Leu Arg Ile Arg Asn His Ser Thr
785                 790                 795                 800

His Thr Lys Asn Gly Ser Pro Gln Lys Gly Tyr Glu Lys Phe Glu Phe
                805                 810                 815

Asn Ile Glu Asp Cys Arg Lys Phe Ile Asp Phe Tyr Lys Gln Ser Ile
            820                 825                 830

Ser Lys His Pro Glu Trp Lys Asp Phe Gly Phe Arg Phe Ser Asp Thr
        835                 840                 845

Gln Arg Tyr Asn Ser Ile Asp Glu Phe Tyr Arg Glu Val Glu Asn Gln
    850                 855                 860

Gly Tyr Lys Leu Thr Phe Glu Asn Ile Ser Glu Ser Tyr Ile Asp Ser
865                 870                 875                 880

Val Val Asn Gln Gly Lys Leu Tyr Leu Phe Gln Ile Tyr Asn Lys Asp
                885                 890                 895

Phe Ser Ala Tyr Ser Lys Gly Arg Pro Asn Leu His Thr Leu Tyr Trp
            900                 905                 910

Lys Ala Leu Phe Asp Glu Arg Asn Leu Gln Asp Val Val Tyr Lys Leu
        915                 920                 925

Asn Gly Glu Ala Glu Leu Phe Tyr Arg Lys Gln Ser Ile Pro Lys Lys
    930                 935                 940

Ile Thr His Pro Ala Lys Glu Ala Ile Ala Asn Lys Asn Lys Asp Asn
945                 950                 955                 960

Pro Lys Lys Glu Ser Val Phe Glu Tyr Asp Leu Ile Lys Asp Lys Arg
                965                 970                 975

Phe Thr Glu Asp Lys Phe Phe His Cys Pro Ile Thr Ile Asn Phe
```

-continued

```
                980             985             990
Lys Ser Ser Gly Ala Asn Lys Phe Asn Asp Glu Ile Asn Leu Leu Leu
            995             1000            1005

Lys Glu Lys Ala Asn Asp Val His Ile Leu Ser Ile Asp Arg Gly
    1010            1015            1020

Glu Arg His Leu Ala Tyr Tyr Thr Leu Val Asp Gly Lys Gly Asn
    1025            1030            1035

Ile Ile Lys Gln Asp Thr Phe Asn Ile Ile Gly Asn Asp Arg Met
    1040            1045            1050

Lys Thr Asn Tyr His Asp Lys Leu Ala Ala Ile Glu Lys Asp Arg
    1055            1060            1065

Asp Ser Ala Arg Lys Asp Trp Lys Lys Ile Asn Asn Ile Lys Glu
    1070            1075            1080

Met Lys Glu Gly Tyr Leu Ser Gln Val Val His Glu Ile Ala Lys
    1085            1090            1095

Leu Val Ile Glu Tyr Asn Ala Ile Val Val Phe Glu Asp Leu Asn
    1100            1105            1110

Phe Gly Phe Lys Arg Gly Arg Phe Lys Val Glu Lys Gln Val Tyr
    1115            1120            1125

Gln Lys Leu Glu Lys Met Leu Ile Glu Lys Leu Asn Tyr Leu Val
    1130            1135            1140

Phe Lys Asp Asn Glu Phe Asp Lys Thr Gly Gly Val Leu Arg Ala
    1145            1150            1155

Tyr Gln Leu Thr Ala Pro Phe Glu Thr Phe Lys Lys Met Gly Lys
    1160            1165            1170

Gln Thr Gly Ile Ile Tyr Tyr Val Pro Ala Gly Phe Thr Ser Lys
    1175            1180            1185

Ile Cys Pro Val Thr Gly Phe Val Asn Gln Leu Tyr Pro Lys Tyr
    1190            1195            1200

Glu Ser Val Ser Lys Ser Gln Glu Phe Phe Ser Lys Phe Asp Lys
    1205            1210            1215

Ile Cys Tyr Asn Leu Asp Lys Gly Tyr Phe Glu Phe Ser Phe Asp
    1220            1225            1230

Tyr Lys Asn Phe Gly Asp Lys Ala Ala Lys Gly Lys Trp Thr Ile
    1235            1240            1245

Ala Ser Phe Gly Ser Arg Leu Ile Asn Phe Arg Asn Ser Asp Lys
    1250            1255            1260

Asn His Asn Trp Asp Thr Arg Glu Val Tyr Pro Thr Lys Glu Leu
    1265            1270            1275

Glu Lys Leu Leu Lys Asp Tyr Ser Ile Glu Tyr Gly His Gly Glu
    1280            1285            1290

Cys Ile Lys Ala Ala Ile Cys Gly Glu Ser Asp Lys Lys Phe Phe
    1295            1300            1305

Ala Lys Leu Thr Ser Val Leu Asn Thr Ile Leu Gln Met Arg Asn
    1310            1315            1320

Ser Lys Thr Gly Thr Glu Leu Asp Tyr Leu Ile Ser Pro Val Ala
    1325            1330            1335

Asp Val Asn Gly Asn Phe Phe Asp Ser Arg Gln Ala Pro Lys Asn
    1340            1345            1350

Met Pro Gln Asp Ala Asp Ala Asn Gly Ala Tyr His Ile Gly Leu
    1355            1360            1365

Lys Gly Leu Met Leu Leu Gly Arg Ile Lys Asn Asn Gln Glu Gly
    1370            1375            1380
```

```
Lys Lys Leu Asn Leu Val Ile Lys Asn Glu Glu Tyr Phe Glu Phe
    1385                1390                1395

Val Gln Asn Arg Asn Asn Pro Lys Lys Lys Arg Lys Val Leu Glu
    1400                1405                1410

Gly Gly Gly Gly Ser Ser Thr Asp His Pro Lys Tyr Ser Asp Met
    1415                1420                1425

Ile Val Ala Ala Ile Gln Ala Glu Lys Asn Arg Ala Gly Ser Ser
    1430                1435                1440

Arg Gln Ser Ile Gln Lys Tyr Ile Lys Ser His Tyr Lys Val Gly
    1445                1450                1455

Glu Asn Ala Asp Ser Gln Ile Lys Leu Ser Ile Lys Arg Leu Val
    1460                1465                1470

Thr Thr Gly Val Leu Lys Gln Thr Lys Gly Val Gly Ala Ser Gly
    1475                1480                1485

Ser Phe Arg Leu Ala Lys Ser Asp Glu Pro
    1490                1495

<210> SEQ ID NO 77
<211> LENGTH: 1687
<212> TYPE: PRT
<213> ORGANISM: Artificial Sequence
<220> FEATURE:
<223> OTHER INFORMATION: SYNTHESIZED

<400> SEQUENCE: 77

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Pro Ala Lys Val
                20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
    50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Ser Ile Tyr Gln Glu Phe Val
            100                 105                 110

Asn Lys Tyr Ser Leu Ser Lys Thr Leu Arg Phe Glu Leu Ile Pro Gln
        115                 120                 125

Gly Lys Thr Leu Glu Asn Ile Lys Ala Arg Gly Leu Ile Leu Asp Asp
    130                 135                 140

Glu Lys Arg Ala Lys Asp Tyr Lys Lys Ala Lys Gln Ile Ile Asp Lys
145                 150                 155                 160

Tyr His Gln Phe Phe Ile Glu Glu Ile Leu Ser Ser Val Cys Ile Ser
                165                 170                 175

Glu Asp Leu Leu Gln Asn Tyr Ser Asp Val Tyr Phe Lys Leu Lys Lys
            180                 185                 190

Ser Asp Asp Asp Asn Leu Gln Lys Asp Phe Lys Ser Ala Lys Asp Thr
        195                 200                 205

Ile Lys Lys Gln Ile Ser Glu Tyr Ile Lys Asp Ser Glu Lys Phe Lys
    210                 215                 220

Asn Leu Phe Asn Gln Asn Leu Ile Asp Ala Lys Lys Gly Gln Glu Ser
225                 230                 235                 240
```

-continued

```
Asp Leu Ile Leu Trp Leu Lys Gln Ser Lys Asp Asn Gly Ile Glu Leu
                245                 250                 255
Phe Lys Ala Asn Ser Asp Ile Thr Asp Ile Asp Glu Ala Leu Glu Ile
            260                 265                 270
Ile Lys Ser Phe Lys Gly Trp Thr Thr Tyr Phe Lys Gly Phe His Glu
        275                 280                 285
Asn Arg Lys Asn Val Tyr Ser Ser Asn Asp Ile Pro Thr Ser Ile Ile
    290                 295                 300
Tyr Arg Ile Val Asp Asp Asn Leu Pro Lys Phe Leu Glu Asn Lys Ala
305                 310                 315                 320
Lys Tyr Glu Ser Leu Lys Asp Lys Ala Pro Glu Ala Ile Asn Tyr Glu
            325                 330                 335
Gln Ile Lys Lys Asp Leu Ala Glu Glu Leu Thr Phe Asp Ile Asp Tyr
        340                 345                 350
Lys Thr Ser Glu Val Asn Gln Arg Val Phe Ser Leu Asp Glu Val Phe
    355                 360                 365
Glu Ile Ala Asn Phe Asn Asn Tyr Leu Asn Gln Ser Gly Ile Thr Lys
370                 375                 380
Phe Asn Thr Ile Ile Gly Gly Lys Phe Val Asn Gly Glu Asn Thr Lys
385                 390                 395                 400
Arg Lys Gly Ile Asn Glu Tyr Ile Asn Leu Tyr Ser Gln Gln Ile Asn
            405                 410                 415
Asp Lys Thr Leu Lys Lys Tyr Lys Met Ser Val Leu Phe Lys Gln Ile
        420                 425                 430
Leu Ser Asp Thr Glu Ser Lys Ser Phe Val Ile Asp Lys Leu Glu Asp
    435                 440                 445
Asp Ser Asp Val Val Thr Thr Met Gln Ser Phe Tyr Glu Gln Ile Ala
450                 455                 460
Ala Phe Lys Thr Val Glu Glu Lys Ser Ile Lys Glu Thr Leu Ser Leu
465                 470                 475                 480
Leu Phe Asp Asp Leu Lys Ala Gln Lys Leu Asp Leu Ser Lys Ile Tyr
            485                 490                 495
Phe Lys Asn Asp Lys Ser Leu Thr Asp Leu Ser Gln Gln Val Phe Asp
        500                 505                 510
Asp Tyr Ser Val Ile Gly Thr Ala Val Leu Glu Tyr Ile Thr Gln Gln
    515                 520                 525
Ile Ala Pro Lys Asn Leu Asp Asn Pro Ser Lys Lys Glu Gln Glu Leu
530                 535                 540
Ile Ala Lys Lys Thr Glu Lys Ala Lys Tyr Leu Ser Leu Glu Thr Ile
545                 550                 555                 560
Lys Leu Ala Leu Glu Glu Phe Asn Lys His Arg Asp Ile Asp Lys Gln
            565                 570                 575
Cys Arg Phe Glu Glu Ile Leu Ala Asn Phe Ala Ala Ile Pro Met Ile
        580                 585                 590
Phe Asp Glu Ile Ala Gln Asn Lys Asp Asn Leu Ala Gln Ile Ser Ile
    595                 600                 605
Lys Tyr Gln Asn Gln Gly Lys Lys Asp Leu Leu Gln Ala Ser Ala Glu
610                 615                 620
Asp Asp Val Lys Ala Ile Lys Asp Leu Leu Asp Gln Thr Asn Asn Leu
625                 630                 635                 640
Leu His Lys Leu Lys Ile Phe His Ile Ser Gln Ser Glu Asp Lys Ala
            645                 650                 655
```

```
Asn Ile Leu Asp Lys Asp Glu His Phe Tyr Leu Val Phe Glu Cys
            660             665             670

Tyr Phe Glu Leu Ala Asn Ile Val Pro Leu Tyr Asn Lys Ile Arg Asn
        675             680             685

Tyr Ile Thr Gln Lys Pro Tyr Ser Asp Glu Lys Phe Lys Leu Asn Phe
        690             695             700

Glu Asn Ser Thr Leu Ala Asn Gly Trp Asp Lys Asn Lys Glu Pro Asp
705             710             715             720

Asn Thr Ala Ile Leu Phe Ile Lys Asp Asp Lys Tyr Tyr Leu Gly Val
            725             730             735

Met Asn Lys Lys Asn Asn Lys Ile Phe Asp Asp Lys Ala Ile Lys Glu
            740             745             750

Asn Lys Gly Glu Gly Tyr Lys Lys Ile Val Tyr Lys Leu Leu Pro Gly
            755             760             765

Ala Asn Lys Met Leu Pro Lys Val Phe Phe Ser Ala Lys Ser Ile Lys
            770             775             780

Phe Tyr Asn Pro Ser Glu Asp Ile Leu Arg Ile Arg Asn His Ser Thr
785             790             795             800

His Thr Lys Asn Gly Ser Pro Gln Lys Gly Tyr Glu Lys Phe Glu Phe
            805             810             815

Asn Ile Glu Asp Cys Arg Lys Phe Ile Asp Phe Tyr Lys Gln Ser Ile
            820             825             830

Ser Lys His Pro Glu Trp Lys Asp Phe Gly Phe Arg Phe Ser Asp Thr
            835             840             845

Gln Arg Tyr Asn Ser Ile Asp Glu Phe Tyr Arg Glu Val Glu Asn Gln
850             855             860

Gly Tyr Lys Leu Thr Phe Glu Asn Ile Ser Glu Ser Tyr Ile Asp Ser
865             870             875             880

Val Val Asn Gln Gly Lys Leu Tyr Leu Phe Gln Ile Tyr Asn Lys Asp
            885             890             895

Phe Ser Ala Tyr Ser Lys Gly Arg Pro Asn Leu His Thr Leu Tyr Trp
            900             905             910

Lys Ala Leu Phe Asp Glu Arg Asn Leu Gln Asp Val Val Tyr Lys Leu
            915             920             925

Asn Gly Glu Ala Glu Leu Phe Tyr Arg Lys Gln Ser Ile Pro Lys Lys
930             935             940

Ile Thr His Pro Ala Lys Glu Ala Ile Ala Asn Lys Asn Lys Asp Asn
945             950             955             960

Pro Lys Lys Glu Ser Val Phe Glu Tyr Asp Leu Ile Lys Asp Lys Arg
            965             970             975

Phe Thr Glu Asp Lys Phe Phe Phe His Cys Pro Ile Thr Ile Asn Phe
            980             985             990

Lys Ser Ser Gly Ala Asn Lys Phe Asn Asp Glu Ile Asn Leu Leu Leu
        995             1000            1005

Lys Glu Lys Ala Asn Asp Val His Ile Leu Ser Ile Asp Arg Gly
    1010            1015            1020

Glu Arg His Leu Ala Tyr Tyr Thr Leu Val Asp Gly Lys Gly Asn
    1025            1030            1035

Ile Ile Lys Gln Asp Thr Phe Asn Ile Ile Gly Asn Asp Arg Met
    1040            1045            1050

Lys Thr Asn Tyr His Asp Lys Leu Ala Ala Ile Glu Lys Asp Arg
    1055            1060            1065

Asp Ser Ala Arg Lys Asp Trp Lys Lys Ile Asn Asn Ile Lys Glu
```

-continued

```
            1070                1075                1080
Met Lys Glu Gly Tyr Leu Ser Gln Val Val His Glu Ile Ala Lys
        1085                1090                1095
Leu Val Ile Glu Tyr Asn Ala Ile Val Val Phe Glu Asp Leu Asn
        1100                1105                1110
Phe Gly Phe Lys Arg Gly Arg Phe Lys Val Glu Lys Gln Val Tyr
        1115                1120                1125
Gln Lys Leu Glu Lys Met Leu Ile Glu Lys Leu Asn Tyr Leu Val
        1130                1135                1140
Phe Lys Asp Asn Glu Phe Asp Lys Thr Gly Gly Val Leu Arg Ala
        1145                1150                1155
Tyr Gln Leu Thr Ala Pro Phe Glu Thr Phe Lys Lys Met Gly Lys
        1160                1165                1170
Gln Thr Gly Ile Ile Tyr Tyr Val Pro Ala Gly Phe Thr Ser Lys
        1175                1180                1185
Ile Cys Pro Val Thr Gly Phe Val Asn Gln Leu Tyr Pro Lys Tyr
        1190                1195                1200
Glu Ser Val Ser Lys Ser Gln Glu Phe Ser Lys Phe Asp Lys
        1205                1210                1215
Ile Cys Tyr Asn Leu Asp Lys Gly Tyr Phe Glu Phe Ser Phe Asp
        1220                1225                1230
Tyr Lys Asn Phe Gly Asp Lys Ala Ala Lys Gly Lys Trp Thr Ile
        1235                1240                1245
Ala Ser Phe Gly Ser Arg Leu Ile Asn Phe Arg Asn Ser Asp Lys
        1250                1255                1260
Asn His Asn Trp Asp Thr Arg Glu Val Tyr Pro Thr Lys Glu Leu
        1265                1270                1275
Glu Lys Leu Leu Lys Asp Tyr Ser Ile Glu Tyr Gly His Gly Glu
        1280                1285                1290
Cys Ile Lys Ala Ala Ile Cys Gly Glu Ser Asp Lys Lys Phe Phe
        1295                1300                1305
Ala Lys Leu Thr Ser Val Leu Asn Thr Ile Leu Gln Met Arg Asn
        1310                1315                1320
Ser Lys Thr Gly Thr Glu Leu Asp Tyr Leu Ile Ser Pro Val Ala
        1325                1330                1335
Asp Val Asn Gly Asn Phe Phe Asp Ser Arg Gln Ala Pro Lys Asn
        1340                1345                1350
Met Pro Gln Asp Ala Asp Ala Asn Gly Ala Tyr His Ile Gly Leu
        1355                1360                1365
Lys Gly Leu Met Leu Leu Gly Arg Ile Lys Asn Asn Gln Glu Gly
        1370                1375                1380
Lys Lys Leu Asn Leu Val Ile Lys Asn Glu Glu Tyr Phe Glu Phe
        1385                1390                1395
Val Gln Asn Arg Asn Asn Pro Lys Lys Lys Arg Lys Val Leu Glu
        1400                1405                1410
Gly Gly Gly Gly Ser Asp Met Asp Ser Ile Gly Glu Ser Glu Val
        1415                1420                1425
Arg Ala Leu Tyr Lys Ala Ile Leu Lys Phe Gly Asn Leu Lys Glu
        1430                1435                1440
Ile Leu Asp Glu Leu Ile Ala Asp Gly Thr Leu Pro Val Lys Ser
        1445                1450                1455
Phe Glu Lys Tyr Gly Glu Thr Tyr Asp Glu Met Met Glu Ala Ala
        1460                1465                1470
```

Lys Asp Cys Val His Glu Glu Lys Asn Arg Lys Glu Ile Leu
        1475                1480                1485

Glu Lys Leu Glu Lys His Ala Thr Ala Tyr Arg Ala Lys Leu Lys
        1490                1495                1500

Ser Gly Glu Ile Lys Ala Glu Asn Gln Pro Lys Asp Asn Pro Leu
        1505                1510                1515

Thr Arg Leu Ser Leu Lys Lys Arg Glu Lys Lys Ala Val Leu Phe
        1520                1525                1530

Asn Phe Lys Gly Val Lys Ser Leu Asn Ala Glu Ser Leu Leu Ser
        1535                1540                1545

Arg Val Glu Asp Leu Lys Tyr Leu Lys Asn Leu Ile Asn Ser Asn
        1550                1555                1560

Tyr Lys Asp Asp Pro Leu Lys Phe Ser Leu Gly Asn Asn Thr Pro
        1565                1570                1575

Lys Pro Val Gln Asn Trp Ser Ser Asn Trp Thr Lys Glu Glu Asp
        1580                1585                1590

Glu Lys Leu Leu Ile Gly Val Phe Lys Tyr Gly Tyr Gly Ser Trp
        1595                1600                1605

Thr Gln Ile Arg Asp Asp Pro Phe Leu Gly Ile Thr Asp Lys Ile
        1610                1615                1620

Phe Leu Asn Glu Val His Asn Pro Val Ala Lys Lys Ser Ala Ser
        1625                1630                1635

Ser Ser Asp Thr Thr Pro Thr Pro Ser Lys Lys Gly Lys Gly Ile
        1640                1645                1650

Thr Gly Ser Ser Lys Lys Val Pro Gly Ala Ile His Leu Gly Arg
        1655                1660                1665

Arg Val Asp Tyr Leu Leu Ser Phe Leu Arg Gly Gly Leu Asn Thr
        1670                1675                1680

Lys Ser Pro Ser
        1685

<210> SEQ ID NO 78
<211> LENGTH: 1185
<212> TYPE: PRT
<213> ORGANISM: Artificial Sequence
<220> FEATURE:
<223> OTHER INFORMATION: SYNTHESIZED

<400> SEQUENCE: 78

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Pro Ala Lys Val
            20                  25                  30

Glu Ala Lys Pro Lys Lys Ala Ala Ala Lys Asp Lys Ser Ser Asp Lys
        35                  40                  45

Lys Val Gln Thr Lys Gly Lys Arg Gly Ala Lys Gly Lys Gln Ala Glu
    50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Ala Arg Ile Leu Ala Phe Asp
            100                 105                 110

Ile Gly Ile Ser Ser Ile Gly Trp Ala Phe Ser Glu Asn Asp Glu Leu
        115                 120                 125

Lys Asp Cys Gly Val Arg Ile Phe Thr Lys Val Glu Asn Pro Lys Thr
130                 135                 140

Gly Glu Ser Leu Ala Leu Pro Arg Arg Leu Ala Arg Ser Ala Arg Lys
145                 150                 155                 160

Arg Leu Ala Arg Arg Lys Ala Arg Leu Asn His Leu Lys His Leu Ile
            165                 170                 175

Ala Asn Glu Phe Lys Leu Asn Tyr Glu Asp Tyr Gln Ser Phe Asp Glu
            180                 185                 190

Ser Leu Ala Lys Ala Tyr Lys Gly Ser Leu Ile Ser Pro Tyr Glu Leu
        195                 200                 205

Arg Phe Arg Ala Leu Asn Glu Leu Leu Ser Lys Gln Asp Phe Ala Arg
210                 215                 220

Val Ile Leu His Ile Ala Lys Arg Gly Tyr Asp Asp Ile Lys Asn
225                 230                 235                 240

Ser Asp Asp Lys Glu Lys Gly Ala Ile Leu Lys Ala Ile Lys Gln Asn
            245                 250                 255

Glu Glu Lys Leu Ala Asn Tyr Gln Ser Val Gly Glu Tyr Leu Tyr Lys
            260                 265                 270

Glu Tyr Phe Gln Lys Phe Lys Glu Asn Ser Lys Glu Phe Thr Asn Val
        275                 280                 285

Arg Asn Lys Lys Glu Ser Tyr Glu Arg Cys Ile Ala Gln Ser Phe Leu
290                 295                 300

Lys Asp Glu Leu Lys Leu Ile Phe Lys Lys Gln Arg Glu Phe Gly Phe
305                 310                 315                 320

Ser Phe Ser Lys Lys Phe Glu Glu Val Leu Ser Val Ala Phe Tyr
            325                 330                 335

Lys Arg Ala Leu Lys Asp Phe Ser His Leu Val Gly Asn Cys Ser Phe
        340                 345                 350

Phe Thr Asp Glu Lys Arg Ala Pro Lys Asn Ser Pro Leu Ala Phe Met
        355                 360                 365

Phe Val Ala Leu Thr Arg Ile Ile Asn Leu Leu Asn Asn Leu Lys Asn
370                 375                 380

Thr Glu Gly Ile Leu Tyr Thr Lys Asp Asp Leu Asn Ala Leu Leu Asn
385                 390                 395                 400

Glu Val Leu Lys Asn Gly Thr Leu Thr Tyr Lys Gln Thr Lys Lys Leu
            405                 410                 415

Leu Gly Leu Ser Asp Asp Tyr Glu Phe Lys Gly Glu Lys Gly Thr Tyr
            420                 425                 430

Phe Ile Glu Phe Lys Lys Tyr Lys Glu Phe Ile Lys Ala Leu Gly Glu
        435                 440                 445

His Asn Leu Ser Gln Asp Leu Asn Glu Ile Ala Lys Asp Ile Thr
450                 455                 460

Leu Ile Lys Asp Glu Ile Lys Leu Lys Ala Leu Ala Lys Tyr Asp
465                 470                 475                 480

Leu Asn Gln Asn Gln Ile Asp Ser Leu Ser Lys Leu Glu Phe Lys Asp
            485                 490                 495

His Leu Asn Ile Ser Phe Lys Ala Leu Lys Leu Val Thr Pro Leu Met
            500                 505                 510

Leu Glu Gly Lys Lys Tyr Asp Glu Ala Cys Asn Glu Leu Asn Leu Lys
        515                 520                 525

Val Ala Ile Asn Glu Asp Lys Lys Asp Phe Leu Pro Ala Phe Asn Glu
530                 535                 540

```
Thr Tyr Tyr Lys Asp Glu Val Thr Asn Pro Val Leu Arg Ala Ile
545                 550                 555                 560

Lys Glu Tyr Arg Lys Val Leu Asn Ala Leu Leu Lys Lys Tyr Gly Lys
                565                 570                 575

Val His Lys Ile Asn Ile Glu Leu Ala Arg Glu Val Gly Lys Asn His
                580                 585                 590

Ser Gln Arg Ala Lys Ile Glu Lys Glu Gln Asn Glu Asn Tyr Lys Ala
                595                 600                 605

Lys Lys Asp Ala Glu Leu Glu Cys Glu Lys Leu Gly Leu Lys Ile Asn
                610                 615                 620

Ser Lys Asn Ile Leu Lys Leu Arg Leu Phe Lys Glu Gln Lys Glu Phe
625                 630                 635                 640

Cys Ala Tyr Ser Gly Glu Lys Ile Lys Ile Ser Asp Leu Gln Asp Glu
                645                 650                 655

Lys Met Leu Glu Ile Asp His Ile Tyr Pro Tyr Ser Arg Ser Phe Asp
                660                 665                 670

Asp Ser Tyr Met Asn Lys Val Leu Val Phe Thr Lys Gln Asn Gln Glu
                675                 680                 685

Lys Leu Asn Gln Thr Pro Phe Glu Ala Phe Gly Asn Asp Ser Ala Lys
                690                 695                 700

Trp Gln Lys Ile Glu Val Leu Ala Lys Asn Leu Pro Thr Lys Lys Gln
705                 710                 715                 720

Lys Arg Ile Leu Asp Lys Asn Tyr Lys Asp Lys Glu Gln Lys Asn Phe
                725                 730                 735

Lys Asp Arg Asn Leu Asn Asp Thr Arg Tyr Ile Ala Arg Leu Val Leu
                740                 745                 750

Asn Tyr Thr Lys Asp Tyr Leu Asp Phe Leu Pro Leu Ser Asp Asp Glu
                755                 760                 765

Asn Thr Lys Leu Asn Asp Thr Gln Lys Gly Ser Lys Val His Val Glu
                770                 775                 780

Ala Lys Ser Gly Met Leu Thr Ser Ala Leu Arg His Thr Trp Gly Phe
785                 790                 795                 800

Ser Ala Lys Asp Arg Asn Asn His Leu His His Ala Ile Asp Ala Val
                805                 810                 815

Ile Ile Ala Tyr Ala Asn Asn Ser Ile Val Lys Ala Phe Ser Asp Phe
                820                 825                 830

Lys Lys Glu Gln Glu Ser Asn Ser Ala Glu Leu Tyr Ala Lys Lys Ile
                835                 840                 845

Ser Glu Leu Asp Tyr Lys Asn Lys Arg Lys Phe Phe Glu Pro Phe Ser
850                 855                 860

Gly Phe Arg Gln Lys Val Leu Asp Lys Ile Asp Glu Ile Phe Val Ser
865                 870                 875                 880

Lys Pro Glu Arg Lys Lys Pro Ser Gly Ala Leu His Glu Glu Thr Phe
                885                 890                 895

Arg Lys Glu Glu Glu Phe Tyr Gln Ser Tyr Gly Gly Lys Glu Gly Val
                900                 905                 910

Leu Lys Ala Leu Glu Leu Gly Lys Ile Arg Lys Val Asn Gly Lys Ile
                915                 920                 925

Val Lys Asn Gly Asp Met Phe Arg Val Asp Ile Phe Lys His Lys Lys
                930                 935                 940

Thr Asn Lys Phe Tyr Ala Val Pro Ile Tyr Thr Met Asp Phe Ala Leu
945                 950                 955                 960

Lys Val Leu Pro Asn Lys Ala Val Ala Arg Ser Lys Lys Gly Glu Ile
```

```
                965                 970                 975
Lys Asp Trp Ile Leu Met Asp Glu Asn Tyr Glu Phe Cys Phe Ser Leu
                    980                 985                 990

Tyr Lys Asp Ser Leu Ile Leu Ile Gln Thr Lys Asp Met Gln Glu Pro
        995                 1000                1005

Glu Phe Val Tyr Tyr Asn Ala Phe Thr Ser Ser Thr Val Ser Leu
    1010                1015                1020

Ile Val Ser Lys His Asp Asn Lys Phe Glu Thr Leu Ser Lys Asn
    1025                1030                1035

Gln Lys Ile Leu Phe Lys Asn Ala Asn Glu Lys Glu Val Ile Ala
    1040                1045                1050

Lys Ser Ile Gly Ile Gln Asn Leu Lys Val Phe Glu Lys Tyr Ile
    1055                1060                1065

Val Ser Ala Leu Gly Glu Val Thr Lys Ala Glu Phe Arg Gln Arg
    1070                1075                1080

Glu Asp Phe Lys Lys Pro Lys Lys Arg Lys Val Leu Glu Gly
    1085                1090                1095

Gly Gly Gly Ser Gly Lys Gly Asp Pro Lys Lys Pro Arg Gly Lys
    1100                1105                1110

Met Ser Ser Tyr Ala Phe Phe Val Gln Thr Cys Arg Glu Glu His
    1115                1120                1125

Lys Lys Lys His Pro Asp Ala Ser Val Asn Phe Ser Glu Phe Ser
    1130                1135                1140

Lys Lys Cys Ser Glu Arg Trp Lys Thr Met Ser Ala Lys Glu Lys
    1145                1150                1155

Gly Lys Phe Glu Asp Met Ala Lys Ala Asp Lys Ala Arg Tyr Glu
    1160                1165                1170

Arg Glu Met Lys Thr Tyr Ile Pro Pro Lys Gly Glu
    1175                1180                1185

<210> SEQ ID NO 79
<211> LENGTH: 1182
<212> TYPE: PRT
<213> ORGANISM: Artificial Sequence
<220> FEATURE:
<223> OTHER INFORMATION: SYNTHESIZED

<400> SEQUENCE: 79

Met Pro Lys Arg Lys Val Ser Ser Ala Glu Gly Ala Ala Lys Glu Glu
1               5                   10                  15

Pro Lys Arg Arg Ser Ala Arg Leu Ser Ala Lys Pro Ala Lys Val
                20                  25                  30

Glu Ala Lys Pro Lys Lys Ala Ala Ala Lys Asp Lys Ser Ser Asp Lys
            35                  40                  45

Lys Val Gln Thr Lys Gly Lys Arg Gly Ala Lys Gly Lys Gln Ala Glu
        50                  55                  60

Val Ala Asn Gln Glu Thr Lys Glu Asp Leu Pro Ala Glu Asn Gly Glu
65                  70                  75                  80

Thr Lys Thr Glu Glu Ser Pro Ala Ser Asp Glu Ala Gly Glu Lys Glu
                85                  90                  95

Ala Lys Ser Asp Thr Gly Ser Gly Met Ala Arg Ile Leu Ala Phe Asp
            100                 105                 110

Ile Gly Ile Ser Ser Ile Gly Trp Ala Phe Ser Glu Asn Asp Glu Leu
        115                 120                 125

Lys Asp Cys Gly Val Arg Ile Phe Thr Lys Val Glu Asn Pro Lys Thr
```

```
                130               135                140
Gly Glu Ser Leu Ala Leu Pro Arg Arg Leu Ala Arg Ser Ala Arg Lys
145                 150                 155                 160

Arg Leu Ala Arg Arg Lys Ala Arg Leu Asn His Leu Lys His Leu Ile
                165                 170                 175

Ala Asn Glu Phe Lys Leu Asn Tyr Glu Asp Tyr Gln Ser Phe Asp Glu
                180                 185                 190

Ser Leu Ala Lys Ala Tyr Lys Gly Ser Leu Ile Ser Pro Tyr Glu Leu
                195                 200                 205

Arg Phe Arg Ala Leu Asn Glu Leu Leu Ser Lys Gln Asp Phe Ala Arg
210                 215                 220

Val Ile Leu His Ile Ala Lys Arg Arg Gly Tyr Asp Asp Ile Lys Asn
225                 230                 235                 240

Ser Asp Asp Lys Glu Lys Gly Ala Ile Leu Lys Ala Ile Lys Gln Asn
                245                 250                 255

Glu Glu Lys Leu Ala Asn Tyr Gln Ser Val Gly Glu Tyr Leu Tyr Lys
                260                 265                 270

Glu Tyr Phe Gln Lys Phe Lys Glu Asn Ser Lys Glu Phe Thr Asn Val
                275                 280                 285

Arg Asn Lys Lys Glu Ser Tyr Glu Arg Cys Ile Ala Gln Ser Phe Leu
290                 295                 300

Lys Asp Glu Leu Lys Leu Ile Phe Lys Lys Gln Arg Glu Phe Gly Phe
305                 310                 315                 320

Ser Phe Ser Lys Lys Phe Glu Glu Val Leu Ser Val Ala Phe Tyr
                325                 330                 335

Lys Arg Ala Leu Lys Asp Phe Ser His Leu Val Gly Asn Cys Ser Phe
                340                 345                 350

Phe Thr Asp Glu Lys Arg Ala Pro Lys Asn Ser Pro Leu Ala Phe Met
                355                 360                 365

Phe Val Ala Leu Thr Arg Ile Ile Asn Leu Leu Asn Asn Leu Lys Asn
                370                 375                 380

Thr Glu Gly Ile Leu Tyr Thr Lys Asp Asp Leu Asn Ala Leu Leu Asn
385                 390                 395                 400

Glu Val Leu Lys Asn Gly Thr Leu Thr Tyr Lys Gln Thr Lys Lys Leu
                405                 410                 415

Leu Gly Leu Ser Asp Asp Tyr Glu Phe Lys Gly Glu Lys Gly Thr Tyr
                420                 425                 430

Phe Ile Glu Phe Lys Lys Tyr Lys Glu Phe Ile Lys Ala Leu Gly Glu
                435                 440                 445

His Asn Leu Ser Gln Asp Asp Leu Asn Glu Ile Ala Lys Asp Ile Thr
450                 455                 460

Leu Ile Lys Asp Glu Ile Lys Leu Lys Lys Ala Leu Ala Lys Tyr Asp
465                 470                 475                 480

Leu Asn Gln Asn Gln Ile Asp Ser Leu Ser Lys Leu Glu Phe Lys Asp
                485                 490                 495

His Leu Asn Ile Ser Phe Lys Ala Leu Lys Leu Val Thr Pro Leu Met
                500                 505                 510

Leu Glu Gly Lys Lys Tyr Asp Glu Ala Cys Asn Glu Leu Asn Leu Lys
                515                 520                 525

Val Ala Ile Asn Glu Asp Lys Lys Asp Phe Leu Pro Ala Phe Asn Glu
530                 535                 540

Thr Tyr Tyr Lys Asp Glu Val Thr Asn Pro Val Val Leu Arg Ala Ile
545                 550                 555                 560
```

Lys Glu Tyr Arg Lys Val Leu Asn Ala Leu Leu Lys Tyr Gly Lys
                565                 570                 575

Val His Lys Ile Asn Ile Glu Leu Ala Arg Glu Val Gly Lys Asn His
                580                 585                 590

Ser Gln Arg Ala Lys Ile Glu Lys Glu Gln Asn Glu Asn Tyr Lys Ala
                595                 600                 605

Lys Lys Asp Ala Glu Leu Glu Cys Glu Lys Leu Gly Leu Lys Ile Asn
                610                 615                 620

Ser Lys Asn Ile Leu Lys Leu Arg Leu Phe Lys Glu Gln Lys Glu Phe
625                 630                 635                 640

Cys Ala Tyr Ser Gly Glu Lys Ile Lys Ile Ser Asp Leu Gln Asp Glu
                645                 650                 655

Lys Met Leu Glu Ile Asp His Ile Tyr Pro Tyr Ser Arg Ser Phe Asp
                660                 665                 670

Asp Ser Tyr Met Asn Lys Val Leu Val Phe Thr Lys Gln Asn Gln Glu
                675                 680                 685

Lys Leu Asn Gln Thr Pro Phe Glu Ala Phe Gly Asn Asp Ser Ala Lys
                690                 695                 700

Trp Gln Lys Ile Glu Val Leu Ala Lys Asn Leu Pro Thr Lys Lys Gln
705                 710                 715                 720

Lys Arg Ile Leu Asp Lys Asn Tyr Lys Asp Lys Glu Gln Lys Asn Phe
                725                 730                 735

Lys Asp Arg Asn Leu Asn Asp Thr Arg Tyr Ile Ala Arg Leu Val Leu
                740                 745                 750

Asn Tyr Thr Lys Asp Tyr Leu Asp Phe Leu Pro Leu Ser Asp Asp Glu
                755                 760                 765

Asn Thr Lys Leu Asn Asp Thr Gln Lys Gly Ser Lys Val His Val Glu
                770                 775                 780

Ala Lys Ser Gly Met Leu Thr Ser Ala Leu Arg His Thr Trp Gly Phe
785                 790                 795                 800

Ser Ala Lys Asp Arg Asn Asn His Leu His His Ala Ile Asp Ala Val
                805                 810                 815

Ile Ile Ala Tyr Ala Asn Asn Ser Ile Val Lys Ala Phe Ser Asp Phe
                820                 825                 830

Lys Lys Glu Gln Glu Ser Asn Ser Ala Glu Leu Tyr Ala Lys Lys Ile
                835                 840                 845

Ser Glu Leu Asp Tyr Lys Asn Lys Arg Lys Phe Phe Glu Pro Phe Ser
850                 855                 860

Gly Phe Arg Gln Lys Val Leu Asp Lys Ile Asp Glu Ile Phe Val Ser
865                 870                 875                 880

Lys Pro Glu Arg Lys Lys Pro Ser Gly Ala Leu His Glu Glu Thr Phe
                885                 890                 895

Arg Lys Glu Glu Glu Phe Tyr Gln Ser Tyr Gly Gly Lys Glu Gly Val
                900                 905                 910

Leu Lys Ala Leu Glu Leu Gly Lys Ile Arg Lys Val Asn Gly Lys Ile
                915                 920                 925

Val Lys Asn Gly Asp Met Phe Arg Val Asp Ile Phe Lys His Lys Lys
                930                 935                 940

Thr Asn Lys Phe Tyr Ala Val Pro Ile Tyr Thr Met Asp Phe Ala Leu
945                 950                 955                 960

Lys Val Leu Pro Asn Lys Ala Val Ala Arg Ser Lys Lys Gly Glu Ile
                965                 970                 975

-continued

```
Lys Asp Trp Ile Leu Met Asp Glu Asn Tyr Glu Phe Cys Phe Ser Leu
            980                 985                 990

Tyr Lys Asp Ser Leu Ile Leu Ile Gln Thr Lys Asp Met Gln Glu Pro
        995                1000                1005

Glu Phe Val Tyr Tyr Asn Ala Phe Thr Ser Ser Thr Val Ser Leu
    1010                1015                1020

Ile Val Ser Lys His Asp Asn Lys Phe Glu Thr Leu Ser Lys Asn
    1025                1030                1035

Gln Lys Ile Leu Phe Lys Asn Ala Asn Glu Lys Glu Val Ile Ala
    1040                1045                1050

Lys Ser Ile Gly Ile Gln Asn Leu Lys Val Phe Glu Lys Tyr Ile
    1055                1060                1065

Val Ser Ala Leu Gly Glu Val Thr Lys Ala Glu Phe Arg Gln Arg
    1070                1075                1080

Glu Asp Phe Lys Lys Pro Lys Lys Lys Arg Lys Val Leu Glu Gly
    1085                1090                1095

Gly Gly Gly Ser Ser Thr Asp His Pro Lys Tyr Ser Asp Met Ile
    1100                1105                1110

Val Ala Ala Ile Gln Ala Glu Lys Asn Arg Ala Gly Ser Ser Arg
    1115                1120                1125

Gln Ser Ile Gln Lys Tyr Ile Lys Ser His Tyr Lys Val Gly Glu
    1130                1135                1140

Asn Ala Asp Ser Gln Ile Lys Leu Ser Ile Lys Arg Leu Val Thr
    1145                1150                1155

Thr Gly Val Leu Lys Gln Thr Lys Gly Val Gly Ala Ser Gly Ser
    1160                1165                1170

Phe Arg Leu Ala Lys Ser Asp Glu Pro
    1175                1180
```